United States Patent
Refaeli et al.

(10) Patent No.: US 8,986,702 B2
(45) Date of Patent: *Mar. 24, 2015

(54) ANTIBODIES AND PROCESSES FOR PREPARING THE SAME

(75) Inventors: Yosef Refaeli, Denver, CO (US); Brian Curtis Turner, Denver, CO (US)

(73) Assignee: Taiga Biotechnologies, Inc., Aurora, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/467,957

(22) Filed: May 18, 2009

(65) Prior Publication Data

US 2009/0291094 A1 Nov. 26, 2009

Related U.S. Application Data

(60) Provisional application No. 61/054,047, filed on May 16, 2008.

(51) Int. Cl.
| | |
|---|---|
| *C12N 5/24* | (2006.01) |
| *C12N 5/16* | (2006.01) |
| *C12N 5/0781* | (2010.01) |
| *C12N 15/13* | (2006.01) |
| *C07K 14/005* | (2006.01) |
| *C07K 14/82* | (2006.01) |
| *C07K 16/00* | (2006.01) |
| *C12N 15/62* | (2006.01) |
| *C07K 16/10* | (2006.01) |
| *C07K 16/40* | (2006.01) |
| *C12N 15/113* | (2010.01) |
| *A61K 39/00* | (2006.01) |

(52) U.S. Cl.
CPC ............ *C07K 16/00* (2013.01); *C07K 16/1018* (2013.01); *C07K 16/40* (2013.01); *C12N 15/113* (2013.01); *A61K 2039/505* (2013.01); *A61K 2039/53* (2013.01); *A61K 2039/55516* (2013.01); *C07K 2319/10* (2013.01); *C12N 2310/14* (2013.01)
USPC .................. 424/185.1; 424/192.1; 424/198.1; 435/69.3; 435/7.24; 435/372.1

(58) Field of Classification Search
None
See application file for complete search history.

(56) References Cited

U.S. PATENT DOCUMENTS

| | | | |
|---|---|---|---|
| 4,963,489 A | 10/1990 | Naughton et al. | |
| 5,476,996 A | 12/1995 | Wilson et al. | |
| 5,698,767 A | 12/1997 | Wilson et al. | |
| 5,811,301 A | 9/1998 | Cameron | |
| 5,824,837 A | 10/1998 | Chen et al. | |
| 5,849,288 A | 12/1998 | Reisner | |
| 6,451,558 B1 | 9/2002 | Cooke et al. | |
| 7,135,287 B1 | 11/2006 | Lonberg et al. | |
| 7,311,920 B1 | 12/2007 | Devico et al. | |
| 7,582,745 B2 * | 9/2009 | Sah et al. ..................... 536/24.5 |
| 7,767,453 B2 | 8/2010 | Zhang | |
| 8,784,825 B2 * | 7/2014 | Refaeli et al. .............. 424/184.1 |
| 8,828,723 B2 * | 9/2014 | Refaeli et al. ................. 435/372 |
| 2001/0049393 A1 | 12/2001 | Coller et al. | |
| 2002/0098166 A1 | 7/2002 | Havemann et al. | |
| 2003/0072794 A1 | 4/2003 | Boulikas | |
| 2003/0138859 A1 | 7/2003 | Barbera-Guillem et al. | |
| 2005/0220705 A1 | 10/2005 | Brooks et al. | |
| 2005/0281816 A1 | 12/2005 | Lamping et al. | |
| 2006/0115898 A1 | 6/2006 | Zhang et al. | |
| 2006/0154331 A1 | 7/2006 | Avidan et al. | |
| 2006/0156422 A1 | 7/2006 | Dalrymple et al. | |
| 2007/0011753 A1 | 1/2007 | Ito et al. | |
| 2007/0067854 A1 | 3/2007 | Habu et al. | |
| 2007/0093420 A1 * | 4/2007 | Yeomans et al. ................ 514/12 |
| 2007/0116691 A1 | 5/2007 | Cambier et al. | |
| 2007/0130628 A1 * | 6/2007 | Brown .............................. 800/6 |
| 2007/0248618 A1 | 10/2007 | Cohen | |
| 2009/0291094 A1 | 11/2009 | Refaeli et al. | |
| 2010/0047217 A1 | 2/2010 | Refaeli et al. | |
| 2010/0055129 A1 | 3/2010 | Refaeli et al. | |
| 2010/0279351 A1 | 11/2010 | Refaeli et al. | |
| 2010/0297763 A1 | 11/2010 | Cambier et al. | |

FOREIGN PATENT DOCUMENTS

| | | |
|---|---|---|
| EP | 1 103 615 | 5/2001 |
| EP | 1103615 | 5/2001 |
| EP | 1357184 A2 | 10/2003 |
| EP | 1792627 A1 | 6/2007 |
| GB | 2387599 A | 10/2003 |
| JP | 2000-189157 | 7/2000 |
| JP | 2001-518300 | 10/2001 |
| JP | 2003-514565 | 4/2003 |

(Continued)

OTHER PUBLICATIONS

Podsypanina, K. et al., "Oncogene cooperation in tumor maintenance and tumor recurrence in mouse mammary tumors induced by MYC and mutant Kras," PNAS 105(13):5242-5247 (2008).

Refaeli, Y. et al., "The protooncogene MYC can break B cell tolerance," PNAS 102(11):4097-4102(2005.

Roh, M. et al., "Transgenic Mice for Cre-Inducible Overexpression of the Oncogenes c-MYC and Pim-1 in Multiple Tissues," Genesis 44:447-453 (2006).

Schmidt E.V. et al., "Transgenic mice bearing the human *c-myc* gene activated by an immunoglobulin enhancer: A pre-B-cell lymphomia model," PNAS USA 85:6047-6051 (1988).

Habib, T., "Myc stimulates B lymphocyte differentiation and amplifies calcium signaling," J.Cell Biol. 179(4):717-731 (2007).

(Continued)

*Primary Examiner* — Phuong Huynh
(74) *Attorney, Agent, or Firm* — Foley & Lardner LLP

(57) ABSTRACT

Provided herein are various processes for the improved production of antibody producing organisms, antibody producing tissues, antibody producing cells and antibodies. In certain embodiments, provided herein are methods for rapidly producing antibody producing organisms, tissues, cells and antibodies derived from humans, organisms, plants or cells that are genetically altered to over-express certain proteins.

23 Claims, 13 Drawing Sheets

(56) References Cited

FOREIGN PATENT DOCUMENTS

| | | |
|---|---|---|
| JP | 2005-523012 A | 8/2005 |
| JP | 2005-525085 | 8/2005 |
| JP | 2005-527211 A | 9/2005 |
| JP | 2009-511081 A | 3/2009 |
| WO | 94/04686 A1 | 3/1994 |
| WO | 94/19465 A2 | 9/1994 |
| WO | WO-98-10058 | 3/1998 |
| WO | WO-98/10058 | 3/1998 |
| WO | WO-99/16884 | 4/1999 |
| WO | 99/45962 A1 | 9/1999 |
| WO | WO-99/53023 | 10/1999 |
| WO | WO-99-53028 | 10/1999 |
| WO | WO-00-09669 | 2/2000 |
| WO | WO-00/09669 | 2/2000 |
| WO | 00/62067 A1 | 10/2000 |
| WO | 01/38548 A2 | 5/2001 |
| WO | WO-03/038057 | 5/2003 |
| WO | 03/089580 A2 | 10/2003 |
| WO | 03/089630 A1 | 10/2003 |
| WO | WO 03/008630 * | 10/2003 |
| WO | WO-03/089580 | 10/2003 |
| WO | WO-03/097675 | 11/2003 |
| WO | 2005/014785 A2 | 2/2005 |
| WO | 2005/084158 A2 | 9/2005 |
| WO | WO-2006-032876 | 3/2006 |
| WO | 2006/116512 A1 | 11/2006 |
| WO | 2007/047583 A2 | 4/2007 |
| WO | 2007/067183 A1 | 6/2007 |
| WO | WO-2008/112922 | 9/2008 |
| WO | WO-2009/059304 | 5/2009 |
| WO | 2009/139930 A2 | 11/2009 |
| WO | WO-2010/011644 | 1/2010 |
| WO | WO-2010/025421 | 3/2010 |

OTHER PUBLICATIONS

Hiramatsu, H., "Complete reconstitution of human lymphocytes from cord blood CD34+ cells using the NOD/SCID/gammacnull mice model," Blood 102(3):873-880 (2003).

Huang, C.Y., "Dynamic regulation of c-Myc proto-oncogene expression during lymphocyte development revealed by a GFP-c-Myc knock-in mouse," Eur. J. Immunol. 38(2):342-349 (2008).

Littlewood, T.D., "A modified oestrogen receptor ligand-binding domain as an improved switch for the regulation of heterologous proteins," Nucleic Acids Res. 23(10:1686-1690 (1995).

Refaeli, Y., "The B cell antigen receptor and overexpression of MYC can cooperate in the genesis of B cell lymphomas," PLOS Biol. 6(6),e152:1208-1225 (2008).

Young, et al., "B-cell receptor signaling in the genesis and maintenance of B-cell lymphoma," Future Oncology 4(5):591-594 (2008).

Australian Search Report and Written Opinion received for Singapore Patent Application No. 201101367-9, mailed on Mar. 23, 2012, 17 pages.

Office Action received for Canadian Patent Application No. 2731767, mailed on Jul. 25, 2012, 3 pages.

Office Action received for Australian Patent Application No. 2009285547, mailed on Jul. 25, 2011, 2 pages.

Office Action received for European Patent Application No. 08743862.8, mailed on Sep. 23, 2010, 6 pages.

Extended European Search Report received for European Patent Application No. 09800871.7, mailed on Jun. 24, 2011, 5 pages.

Extended European Search Report received for European Patent Application No. 09810692.5, mailed on Jul. 11, 2011, 5 pages.

Office Action received for Israel Patent Application No. 208810, mailed on Nov. 2, 2011, 3 pages of English Translation only.

Office Action received for Israel Patent Application No. 209968, mailed on Nov. 2, 2011, 3 pages of English Translation only.

Office Action received for Israel Patent Application No. 209343, mailed on Nov. 2, 2011, 3 pages of English Translation only.

Office Action received for Korean Patent Application No. 10-2009-7021320, mailed on Jul. 29, 2011, 7 pages (3 pages of English Translation and 4 pages of Office Action).

International Preliminary Report on Patentability received for PCT Patent Application No. PCT/US2006/040379, mailed on Apr. 23, 2008, 5 pages.

International Search Report and Written Opinion received for PCT Patent Application No. PCT/US2008/082263, mailed on Jun. 25, 2009, 8 pages.

International Search Report and written Opinion Received for PCT Patent Application No. PCT/US2009/051242, mailed on Feb. 19, 2010, 9 pages.

International Preliminary Report on Patentability received for PCT Patent Application No. PCT/US2008/082263, issued on May 4, 2010, 6 pages.

International Search Report and Written Opinion received for PCT Patent Application No. PCT/US2009/055443, mailed on Jun. 30, 2010, 11 pages.

International Preliminary Report on Patentability Received for Application No. PCT/US2009/003105, mailed on Nov. 17, 2010, 6 pages.

International Preliminary Report on Patentability received for PCT Patent Application No. PCT/US2009/051242, mailed on Feb. 3, 2011, 7 pages.

International Preliminary Report on Patentability received for PCT Patent Application No. PCT/US2009/055443, issued on Mar. 10, 2011, 7 pages.

Non Final Office Action received for U.S. Appl. No. 12/962,197, mailed on Aug. 26, 2011, 20 pages.

Non Final Office Action received for U.S. Appl. No. 12/048,148, mailed on Oct. 13, 2011, 20 pages.

Non-Final Office Action received for U.S. Appl. No. 12/550,166, mailed on Jan. 11, 2012, 24 pages.

Berkson et al., "Pilot Screening Programme for Small Molecule Activators of p53", International Journal of Cancer, vol. 115, 2005, pp. 701-710.

Caron et al., "Endosome disruption enhances the functional nuclear delivery of Tat-fusion proteins", Biochemical and Biophysical Research Communications, vol. 319, 2004, pp. 12-20.

Carotta et al., "Directed Differentiation and Mass Cultivation of Pure Erythorid Progenitors from Mouse Embryonic Stem Cells", Blood, vol. 104, No. 6, Sep. 15, 2004, pp. 1873-1880.

Chen et al., "Small-Molecule Anthracene-Induced Cytotoxicity and Induction of Apoptosis through Generation of Reactive Oxygen Species", Biological & Pharmaceutical Bulletin, vol. 27, No. 6, Jun. 2004, pp. 838-845.

Coller et al., "Expression Analysis with Oligonucleotide Microarrays Reveals that MYC Regulates Genes Involved in Growth, Cell Cycle, Signaling, and Adhesion", Proc. Natl. Acad. Sci. USA, vol. 97, No. 7, Mar. 28, 2000, pp. 3260-3265.

Dang et al., "Identification of the Human c-myc Protein Nuclear Translocation Signal", Molecular and Cellular Biology, vol. 8, No. 10, Oct. 1988, pp. 4048-4054.

Kelso et al., "Survival of the Myeloid Progenitor Cell Line FDC-P1 is Prolonged by Interferon-γ or Interleukin-4", Growth Factors, vol. 6, No. 3, 1992, pp. 233-242.

Qin et al., "Nuclear Factor κB Nuclear Translocation Upregulates c-Myc and p53 Expression during NMDA Receptor-Mediated Apoptosis in Rat Striatum", The Journal of Neuroscience, vol. 19, No. 10, May 15, 1999, pp. 4023-4033.

Radhakrishnan et al., "A Novel Transcriptional Inhibitor Induces Apoptosis in Tumor Cells and Exhibits Antiangiogenic Activity", Cancer Research, vol. 66, No. 6, Mar. 15, 2006, pp. 3264-3270.

Office Action received for Israel Patent Application No. 200919, mailed on Dec. 5, 2011, 2 pages of English Translation only.

Office Action received for Chinese Patent Application No. 200980126312.4, mailed on Jan. 30, 2012, 14 pages ( 7 pages of English translation and 7 pages of Office Action).

Extended European Search Report received for European Patent Application No. 09747016.5, mailed on May 30, 2012, 8 pages.

Office Action received for Japanese Patent Application No. 2009-553785, mailed on Jun. 19, 2012, 6 pages (2 pages of English Translation and 4 pages of Office Action).

Ju et al., "Anti-Apoptotic Therapy with a Tat Fusion Protein Protects Against Excitotoxic Insults in Vitro and in Vivo", Experimental Neurology, vol. 210, 2008, pp. 602-607.

(56) References Cited

OTHER PUBLICATIONS

Office Action received for Chinese Patent Application No. 200980126312.4, issued on Aug. 28, 2012, 12 pages (6 pages of English Translation and 6 pages of Office Action).
Office Action received for Korean Patent Application No. 10-2009-7021320, mailed on Sep. 18, 2012, 11 pages (7 pages of English Translation and 4 pages of Office Action).
Office Action received for Israel Patent Application No. 209343, mailed on Aug. 14, 2012, 4 pages.
Office Action received for Israel Patent Application No. 209968, mailed on Aug. 21, 2012, 4 pages (2 pages of English Translation and 2 pages of Office Action).
Office Action received for Chinese Patent Application No. 200880015602.7, issued on Oct. 31, 2012, 10 pages (6 pages of English Translation and 4 pages of Chinese Office Action).
Office Action received for Canadian Patent Application No. 2,735,522, mailed on Sep. 10, 2012, 3 pages.
Office Action received for Chinese Patent Application No. 200980127166.7, issued on Dec. 5, 2012, 3 pages.
Restriction Requirement received for U.S. Appl. No. 11/583,970, mailed on Nov. 13, 2007, 14 pages.
Non-Final Office Action Response filed for U.S. Appl. No. 11/583,970 on Aug. 12, 2008, 12 pages.
Final Office Action Response filed for U.S. Appl. No. 11/583,970 on Jan. 28, 2009, 15 pages.
Non-Final Office Action Response filed for U.S. Appl. No. 11/583,970 on Jun. 24, 2009, 11 pages.
Final Office Action Response filed for U.S. Appl. No. 11/583,970 on Feb. 4, 2010, 10 pages.
Restriction Requirement received for U.S. Appl. No. 12/701,383, mailed on Jan. 25, 2011, 10 pages.
Non Final Office Action received for U.S. Appl. No. 12/701,383, mailed on Apr. 28, 2011, 10 pages.
Non Final Office Action received for U.S. Appl. No. 11/583,970, mailed on May 9, 2011, 11 pages.
Non-Final Office Action Response filed for U.S. Appl. No. 11/583,970 on Aug. 25, 2011, 22 pages.
Non Final Office Action Response filed for U.S. Appl. No. 12/701,383 Aug. 25, 2011, 20 pages.
Final Office Action received for U.S. Appl. No. 12/701,383, mailed on Nov. 16, 2011, 14 pages.
Final Office Action received for U.S. Appl. No. 11/583,970, mailed on Nov. 17, 2011, 16 pages.
Final Office Action Response filed for U.S. Appl. No. 12/701,383 on Feb. 15, 2012, 13 pages.
Final Office Action Response filed for U.S. Appl. No. 11/583,970 on Feb. 16, 2012, 14 pages.
Final Office Action received for U.S. Appl. No. 12/048,148, mailed on Feb. 15, 2013, 17 pages.
Office Action received for Australian Patent Application No. 2006304392, mailed on Jul. 16, 2012, 3 pages.
Office Action received for Chinese Patent Application No. 200680045545.8, mailed on Dec. 31, 2010, 14 pages (8 pages English Translation and 6 pages of Chinese Office Action).
Response to First Office Action filed in Chinese Patent Application No. 200680045545.8 on Jul. 15, 2011, 22 pages (8 pages of English Machine Translation and 14 pages of Chinese-Language Response).
Office Action received in Chinese Patent Application No. 200680045545.8, issued on Sep. 15, 2011, 16 pages (8 pages of English Machine Translation and 8 pages of Chinese Office Action).
Response to Second Office Action filed in Chinese Patent Application No. 200680045545.8 on Jan. 30, 2012, 23 pages (8 pages of English Machine Translation and 15 pages of Chinese-Language Response).
Office Action received for Chinese Patent Application No. 200580031540.5, mailed on Jul. 3, 2012, 19 pages (11 pages English Translation, 8 pages Office Action).
Request for ReExamination filed in Chinese Patent Application No. 200680045545.8 on Oct. 12, 2012, 17 pages (6 pages of English Machine Translation and 11 pages of Chinese-Language Document as filed).

Office Action received for European Patent Application No. 06826025.6, mailed on Sep. 1, 2009, 3 pages.
Office Action received for European Patent Application No. 06826025.6, mailed on Sep. 22, 2009, 1 page.
Response for European Patent Application No. 09800871.7, filed on Jan. 20, 2012, 5 pages.
Response for European Patent Application No. 09810692.5, filed on Jan. 31, 2012, 7 pages.
Response for European Patent Application No. 09800871.7, filed on Jul. 10, 2012, 5 pages.
Response for European Patent Application No. 09810692.5, filed on Jul. 30, 2012, 5 pages.
Response for European Patent Application No. 09800871.7, filed on Feb. 6, 2013, 9 pages.
Extended European Search Report received for European Patent Application No. 12187077.8, mailed on Mar. 25, 2013, 7 pages.
Extended European Search Report and Search Opinion received for Patent Application No. 12187097.6, mailed on Mar. 27, 2013, 8 pages.
Office Action received for European Patent Application No. 09747016.5, mailed on Apr. 9, 2013, 6 pages.
Office Action received for Japanese Patent Application No. 2008-536713, mailed on Jul. 3, 2012, 2 pages (No English Translation Provided).
Response to Office Action filed in Japanese Patent Application No. 2008-536713 on Oct. 3, 2012, 21 pages (11 pages of English Machine Translation and 10 pages of Japanese-Language Response).
Office Action received for Israeli Patent Application No. 190946, mailed on Jul. 3, 2012, 1 page (English Translation only).
Office Action received for Israel Patent Application No. 200919, mailed on Jan. 17, 2013, 4 pages (2 pages of English Translation and 2 pages of Official Copy).
Office Action received for Israeli Patent Application No. 208810, mailed on Jan. 2, 2013, 8 pages (4 pages of English Translation and 4 pages of Official Copy).
Aubry et al., "N-Myc Shares Cellular Functions with c-Myc", DNA and Cell Biology, vol. 19, No. 6, 2000, pp. 353-364.
Baum, Christopher, "Insertional Mutagenesis in Gene Therapy and Stem Cell Biology", Current Opinion in Hematology, vol. 14, 2007, pp. 337-342.
Beerens et al., "Protein Transduction Domains and their Utility in Gene Therapy", Current Gene Therapy, vol. 3, No. 5, 2003, pp. 486-494.
Buske et al., "Deregulated Expression of HOXB4 Enhances the Primitive Growth Activity of Human Hematopoietic Cells", Blood, vol. 100, No. 3, Aug. 1, 2002, pp. 862-868.
Capecchi, Mario R., "Altering the Genome by Homologous Recombination", Science, vol. 244, Jun. 16, 1989, pp. 1288-1292.
Chin et al., "Essential Role for Oncogenic Ras in Tumour Maintenance", Nature, vol. 400, Jul. 29, 1999, pp. 468-472.
Choi et al., "Myc Protein is Stabilized by Suppression of a Novel E3 Ligase Complex in Cancer Cells", Genes & Development, vol. 24, 2010, pp. 1236-1241.
Dang, Chi V., "c-Myc Target Genes Involved in Cell Growth, Apoptosis, and Metabolism", Molecular and Cellular Biology, vol. 19, No. 1, Jan. 1999, pp. 1-11.
Hann et al., "Proteins Encoded by the Human C-Myc Oncogene: Differential Expression in Neoplastic Cells", Molecular and Cellular Biology, vol. 4, No. 11, Nov. 1984, pp. 2486-2497.
Huettner et al., "Reversibility of Acute B-Cell Leukaemia Induced by BCR-ABL 1", Nature Genetics, vol. 24, Jan. 2000, pp. 57-60.
Li et al., "Reconstitution of Functional Human B Lymphocytes in NOD/SCID Mice Engrafted with ex vivo Expanded CD34+ Cord Blood Cells", Experimental Hematology, vol. 30, 2002, pp. 1036-1043.
Merino et al., "Developmental Regulation of the Bcl-2 Protein and Susceptibility to Cell Death in B Lymphocytes", The EMBO Journal, vol. 13, No. 3, 1994, pp. 683-691.
Muchmore et al., "X Ray and NMR Structure of Human Bcl-xL, an Inhibitor of Programmed Cell Death", Nature, vol. 381, May 23, 1996, pp. 335-341.
Schiedlmeier et al., "High-Level Ectopic HOXB4 Expression Confers a Profound in Vivo Competitive Growth Advantage on Human

(56) References Cited

OTHER PUBLICATIONS

Cord Blood CD34+ Cells, but Impairs Lymphomyeloid Differentiation", Blood, vol. 101, No. 5, Mar. 1, 2003, pp. 1759-1768.
Zhang et al., "Cytokines Regulating Hematopoietic Stem Cell Function", Current Opinion Hematology, vol. 15, No. 4, Jul. 2008, pp. 1-8.
Office Action received for Chinese Patent Application No. 200880015602.7, mailed on Jan. 31, 2012, 16 pages (10 pages of English translation and 6 pages of Office Action).
Office Action received for European Patent Application No. 09810692.5, mailed on Mar. 28, 2012, 3 pages.
Non Final Office Action Received for U.S. Appl. No. 12/506,894, mailed on Apr. 27, 2012, 34 pages.
Final Office Action Received for U.S. Appl. No. 12/550,166, mailed on May 11, 2012, 12 pages.
Non Final Office Action Received for U.S. Appl. No. 12/048,148, mailed on May 11, 2012, 22 pages.
Oral Proceeding received for European Patent Application No. 08743862.8, mailed on May 14, 2012, 6 pages.
Bunting et al., "Restoration of lymphocyte function in Janus kinase 3-deficient mice by retroviral-mediated gene transfer," Nature Medicine 4:58-64 (1998).
Chadwick et al., "Notch Signaling Induces Apoptosis in Primary Human CD34+ Hematopoietic Progenitor Cells," Stem Cells 25:203-210 (2007).
Cheng et al., "BCL-2, BCL-$X_L$ Sequester BH3 Domain-Only Molecules Preventing BAX- and BAK-Mediated Mitochondrial Apoptosis," Mol Cell 8:705-711 (2001).
Conti, L. et al., "Gene therapy using neural stem cells," Methods Mol. Biol. 198:233-244 (2002).
DeoCampo et al., "Cooperation of bcl-2 and myc in the neoplastic transformation of normal rat liver epithelial cells is related to the down-regulation of gap junction-mediated intercellular communication," Carcinogenesis 21(8):1501-1506 (2000).
Eilers, M. et al., "Chimeras of MYC Oncoprotein and Steroid Receptors Cause Hormone-Dependent Transformation of Cells," Nature 340(6228):66-68 (1989).
Eischen et al., "Apoptosis Triggered by Myc-Induced Suppession of Bcl-$X_L$ or Bcl-2 is Bypassed during Lymphomagenesis," Mol Cell Biol 21:5063-5070 (2001).
Esdar, C. et al., "Differentiation-associated apoptosis of neural stem cells is effected by Bcl-2 overexpression: impact on cell lineage determination," Eur. J. Cell Biol. 80(8):539-553 (2001).
Felsher and Bishop, "Reversible Tumorigenesis by *MYC* in Hematopoietic Lineages," Mol Cell 4:199-207 (1999).
Gauss, "DEAE-dextran enhances electroportation of mammalian cells," Nucl Acids Res 20(24):6739-6740 (1992).
Guzman et al., "Preferential induction of apoptosis for primary human leukemic stem cells," PNAS 99(25):16220-16225 (2002).
Hoffman, "Progress in the development of systems in vitro expansion of human hematopoietic stem cells," Curr Op Hematology 6(3):14 pages (1999).
Horton, S.J. et al., "Continuous MLL-ENL expression is necessary to establish a "Hox Code" and maintain immortalization of hematopoietic progenitor cells," Cancer Res. 65(20):9245-9252 (2005).
Hoshimaru, M. et al., "Differentiation of the immortalized adult neuronal progenitor cell line HC2S2 into neurones by regulatable suppression of the V-MYC oncogene," Proceedings of the National Acadamy of Sciences of USA 93(4):1518-1523 (1996).
Howard, M.J. et al., "Transplantation of apoptosis-resistant embryonic stem cells into the injured rat spinal cord," Somatosensory & Motor Research 22(1-2):37-44 (2005).
Korbling et al., "Allogeneic Blood Stem Cell Transplantation: Peripheralization and Yield of Donor-Derived Primitive Hematopoietic Progenitor Cells (CD34+ Thy-1$^{dim}$) and Lymphoid Subsets, and Possible Predictors of Engraftment and Graft-Versus-Host Disease," Blood 86:2842-2848 (1995).
Krosl et al., "In vitro expansion of hematopoietic stem cells by recombinant TAT-HOXB4 protein," Nature Med 9(11):1428-1432 (2003).

McCarthy, "Underground movement," Nature Reviews Cancer 7:1 page (2007).
MacPherson, P. et al., "Activity-dependent gene regulation in conditionally-immortalized muscle precursor cell lines," J. Cell. Biol. 91(4):821-839 (2004).
Melkonyan et al., "Electroporation efficiency in mammalian cells is increased by dimethyl sulfoxide (DMSO)," Nucl. Acids Res. 24:4356-4357 (1996).
Miller et al., "Expansion in vitro of adult murine hemapoietic stem cells with transplantable lympho-myeloid reconstituting ability," PNAS USA 94:13648-13653 (1997).
Mooslehner et al., "Retroviral Integration Sites in Transgenic Mov Mice Frequently Map in the Vicinity of Transcribed DNA Regions," J Virol 64:3056-3058 (1990).
Moore et al., "In Vitro Maintenance of Highly Purified, Transplantable hematopoietic Stem Cells," Blood 89(12):4337-4347 (1997).
Pierelli et al., "Modulation of bcl-2 and p27 in human primitive proliferating hematopoietic progenitors by autocrine TGF-β1 is a cell cycle-independent effect and influences their hematopoietic potential," Blood 95:3001-3010 (2000).
Pinto et al., "Hematopoietic progenitor/stem cells immortalized by Lhx2 generate functional hematopoietic cells in vivo," Blood 99(11):3939-3946 (2002).
Pollock, K. et al., "A conditionally immortal clonal stem cell line from human cortical neuroepithelium for the treatment of ischemic stroke," Exp. Neurology 199(1):143-155 (2006).
Raymon, H.K. et al., "Immortalized human dorsal root ganglion cells differentiate into neurons with nociceptive properties," J. Neuroscience 19(13):5420-5428 (1999).
Richter et al., "Lhx2 expression in hematopoietic progenitor/stem cells in vivo causes a chronic myeloproliferative disorder andaltered globin expression," J Hematology 88(12):1336-1347 (2003).
Rosenwald et al., "Increased expression of eukaryotic translation initiation facots e1F-4E and e1F-2alpha in response to growth induction by c-myc," PNAS USA 90:6175-6178 (1993).
Sauer, "Inducible Gene Targeting in Mice Using the Cre/*lox* System," Methods: A Comparison to Methods in Enzymology 14:381-392 (1998).
Schroy and Todd, "A Simple Method for Freezing and Thawing Cultured Cells," Methods in Cell Science 2:309-310 (1976).
Schwarze et al., "Protein transduction: unrestricted delivery into all cells?" Trends in Cell Biology 10:290-295 (2000).
Sipone, S. et al., "Modeling brain pathologies using neural stem cells," Methods Mol. Biol. 198:245-262 (2002).
Takahashi et al., "Induction of Pluripotent Stem Cells from Mouse Embryonic and Adult Fibroblast Cultures by Defined Factors," Cell 126:663-676 (2006).
Tsai et al., "Lymhohematopoietic progenitors immortalized by a retroviral vector harboring a dominant-negative retinoic acid receptor can recapitulate lymphoid, myeloid, and erythroid development," Genes & Dev. 8:2831-2841 (1994).
Varnum-Finney et al., "Pluripotent, cytokine-dependent, hematopoietic stem cells are immortalized by constitutive Notch 1 signaling," Nature Medicine 6(11):1278-1281 (2000).
Vaux et al., "Bcl-2 gene promotes heamopoietic cell survival and cooperates with c-myc to immortalize pre-B cells," Nature 335:440-442 (1988).
Wang et al., "Primitive Human Hematopoietic Cells Are Enriched in Cord Blood Compared With Adult Bone Marrow or Mobilized Peripheral Blood as Measured by the Quantitative In Vivo SCID-Repopulating Cell Assay," Blood 89:3919-3924 (1997).
Wikipedia [online], 2008, [retrieved on Nov. 13, 2008], Retrieved from Internet: URL:http://en.wikipedia.org/wiki/Stem_cell, pp. 1-11.
Wilson et al., "c-Myc controls the balance between hematopoietic stem cell self-renewal and differentiation," Genes and Development 18:2474-2763 (2007).
Wurm and Bernard, "Large-scale transient expression in mammalian cells for recombinant protein production," Curr Op Biotech 10:156-159 (1999).
Yanai et al., "A novel stromal cell-dependent hematopoietic cell line established from temperature-sensitive SV40 T-antigen transgenic mice," Exp Hematology 27:1087-1096 (1999).

(56) References Cited

OTHER PUBLICATIONS

PCT/US06/40379 Search Report dated Apr. 23, 2008.
PCT/US06/40379 Search Report and Written Opinion mailed Sep. 24, 2007.
EP 08743862 Supplementary Search Report dated Feb. 9, 2010.
EP08743862 Office Action dated May 14, 2010.
EP 06826025 Supplementary Search Report dated Jul. 28, 2009.
PCT/US08/56896 Written Opinion dated Jul. 18, 2008.
PCT/US08/56896 Internationl Preliminary Report on Patentability dated Sep. 15, 2009.
U.S. Appl. No. 12/048,148 Office Action mailed Jan. 19, 2011.
U.S. Appl. No. 11/583,970 Office Action mailed Nov. 4, 2009.
U.S. Appl. No. 11/583,970 Office Action mailed Mar. 23, 2009.
U.S. Appl. No. 11/583,970 Office Action mailed Nov. 26, 2008.
U.S. Appl. No. 11/583,970 Office Action mailed Mar. 12, 2008.
English Translation of Fourth Office Action received for Chinese Patent Application No. 200880015602.7 dated Nov. 11, 2013, 6 pages.
English Translation of Office Action received for Eurasian Patent Application No. 201001762/28, posted Oct. 16, 2013, 1 page.
English translation of Office Action received for Israeli Patent Application No. 190946, dated Apr. 22, 2013, 1 page.
English Translation of Office Action received for Israeli Patent Application No. 209968 dated Jan. 2, 2014, 2 pages.
English translation of Office Action received for Japanese Application No. 2008-536713 dated Aug. 5, 2013, 2 pages.
English Translation of Office Action received for Korean Patent Application No. 10-2008-7011791 dated Jan. 15, 2014, 3 pages.
English Translation of Office Action received for Korean Patent Application No. 10-2013-7028338, dated Jan. 15, 2014, 3 pages.
English Translation of Second Office Action received for Chinese Patent Application No. 200980127166.7, dated Jun. 10, 2013, 1 page.
Extended European Search Report received for European Patent Application No. 06826025.6, mailed on Aug. 13, 2009, 8 pages.
Non-Final Office Action on U.S. Appl. No. 11/583,970 dated Sep. 20, 2013, 19 pages.
Notice of Allowance received for U.S. Appl. No. 12/550,166, mailed on Nov. 26, 2012, 9 pages.
Office Action received for Canadian Patent Application No. 2626525, dated Apr. 17, 2013, 4 pages.
Office Action received for Indian Application No. 3332/DELNP/2008 dated Aug. 23, 2013, 3 pages.
Office Action received for Japanese Application No. 2011-520133, dated Feb. 5, 2014, 4 pages (in Japanese).
Office Action received for Korean Patent Application No. 10-2008-7011791, dated May 28, 2013, English translation, 3 pages.
Soane,L., et al., "TAT-mediated endocytotic delivery of the loop deletion Bcl-2 protein protects neurons against cell death", Journal of Neurochemistry, (2005), vol. 95, pp. 230-243.
Thomas, et. al., "Progress and Problems with the Use of Viral Vectors for Gene Therapy", Nature, (May 2003), vol. 4, pp. 346-358.
Yagihashi, et al., "Detection of Anti-Survivin Antibody in Gastrointestinal Cancer Patients", Clinical Chemistry, (2001), vol. 47, No. 9, pp. 1729-1731.
Final Office Action received for Korean Patent Application No. 10-2009-7021320, mailed on May 29, 2013, 6 pages (3 pages of English Translation and 3 pages of Office Action).
Office Action received for Chinese Patent Application No. 200880015602.7, mailed on May 9, 2013, 13 pages (8 pages of English Translation and 5 pages of Official copy).
Dvorak et al., "Cytochemical Localization of Peroxidase Activity in the Developing Erythrocyte," Am. J. Pathol. 1972, 67(2), pp. 303-326.
Examination Report on Australian application 2009274172, mailed Jul. 24, 2014.
International Search Report and Written Opinion for International Application No. PCT/US2014/022971 dated Aug. 13, 2014, 12 pages.
International Search Report and Written Opinion on PCT/US2014/022977, mailed Aug. 28, 2014.
Notice of Allowance on U.S. Appl. No. 11/583,970, mailed Aug. 29, 2014.
Xi et al., "In Vitro Large Scale Production of Human Mature Red Blood Cells From Hematopoietic Stem Cells by Cuculturing with Human Fetal Liver Stromal Cells," Biomed. Res. Int. Epub Jan. 30, 2013, 2013:807863.
Choi, et al., "Status Epilepticus-Induced Somatostatinergic Hilar Interneuron Degeneration is Regulated by Striatal Enriched Protein Tyrosine Phosphatase", Journal of Neuroscience, (2007), vol. 27, No. 11, pp. 2999-3009.
English Translation of Office Action received for Chinese Patent Application No. 200980126312.4 dated Jan. 22, 2014, 3 pages.
English Translation of Office Action received for Japanese Patent Application No. 2011-525258 dated Feb. 17, 2014, 4 pages.
Ho, et al., "Synthetic Protein Transduction Domains: Enhanced Transduction Potential in Vitro and in Vivo", Cancer Research, (2001), vol. 61, pp. 474-477.
Iritani, et al., "c-Myc enhances protein synthesis and cell size during B lymphocyte development", PNAS, (1999), vol. 96, No. 23, pp. 13180-13185.
Jadlowsky, et al., "Dominant negative mutant Cyclin T1 proteins inhibit HIV transcription by specifically degrading Tat", Retrovirology, (2008), vol. 5, Article 63, 12 pages.
Kashio, et al., "A Protein Derived From the Fusion of TAT Peptide and FNK, a Bcl-xL Derivative, Prevents Cochlear Hair Cell Death From Aminoglycoside Ototoxicity In Vivo", Journal of Neuroscience Research, (2007), vol. 85, No. 7, pp. 1403-1412.
Kitada, et al., "Reversal of Chemoresistance of Lymphoma Cells by Antisense-Mediated Reduction of bcl-2 Gene Expression", Antisense Research and Development, (1994), vol. 4, pp. 71-79.
Non-final Office Action on U.S. Appl. No. 13/795,659 dated Mar. 10, 2014, 11 pages.
Non-final Office Action on U.S. Appl. No. 13/797,648 dated Apr. 3, 2014, 13 pages.
Office Action received for Australian Patent Application No. 2009246876 dated Jan. 17, 2014, 6 pages.
Office Action received for European Application No. 09810692.5 dated Feb. 25, 2014, 3 pages.
Rabbitts, et al., "Metabolism of c-myc gene products: c-myc mRNA and protein expression in the cell cycle", EMBO Journal, (1985), vol. 4, No. 8, pp. 2009-2015.
Snyder, et al., "Regulation of NMDA receptor trafficking by amyloid-3B2", Nature Neuroscience, (2005), vol. 8, No. 8, pp. 1051-1058.
Theis, et al., "Expression of the myc/His-Tagged Human Peptide Transporter hPEPT1 in Yeast for Protein Purification and Functional Analysis", Protein Expression and Purification, (2001), vol. 22, pp. 436-442.
Vaux, et al., "Immunologic competence of B cells subjected to constitutive c-myc oncogene expression in immunoglobulin heavy chain enhancer myc transgenic mice", J. Immunol., (1987), vol. 139, No. 11, pp. 3854-3860.
Benassayag et al., "Human c-Myc Isoforms Differentially Regulate Cell Growth and Apoptosis in *Drosophila melanogaster*," Molecular and Cellular Biology 25(22): 9897-9909 (2005).
Dang et al., "Nuclear and Nucleolar Targeting Sequences of c-erb-A, c-myb, N-myc, p53, HSP70 and HIV tat Proteins". Journal of Biological Chemistry, vol. 264, No. 30, pp. 18019-18023 (1989).
English Translation of European Search Report in European Patent Application No. 13188850.0 dated May 27, 2014, 8 pages.
English Translation of Office Action in Israeli Patent Application No. 200919 dated May 19, 2014, 3 pages.
Final Office Action in U.S. Appl. No. 13/795,659 dated Jul. 11, 2014, 16 pages.
Notice of Allowance in U.S. Appl. No. 13/777,967 dated Jul. 14, 2014, 11 pages.
Sunyer, "Evolutionary and Functional Relationships of B Cells from Fish and Mammals: Insights into their Novel Roles in Phagocytosis and Presentation of Particulate Antigen," Infect Disord Drug Targets 12(3):200-212 (2012).
Trumpp et al., "c-Myc Regulates Mammalian Body Size by Controlling Cell Number But Not Cell Size," Nature 414: 768-773 (2001).

(56) References Cited

OTHER PUBLICATIONS

Deocampo, et al., "Cooperation of BCL-2 and MYC in the Neoplastic Transformation of Normal Rat Lever Epithelial Cells is Related to the Down-Regulation of Gap Junction-Mediated Intercellular Communication", Carcinogenesis, vol. 21, No. 8, pp. 1501-1506,(2000).
English Translation of Notification of Reasons of Refusal for Japanese Patent Application No. 2012-221023 dated Jun. 24, 2014, 2 pages.
English Translation of Office Action on Chinese Application. No. 200980127166.7 dated Apr. 11, 2014, 3 pages.
English Translation of Office Action on Japanese Patent Application. No. 2012-221023 dated Apr. 22, 2014, 3 pages.
English Translation of Third Office Action on Japanese Patent Application No. 2009-553785 dated Apr. 22, 2014, 3 pages.
Examination Report for Indian Patent Application No. 3332/DELNP/2008 dated Aug. 23, 2013, 6 pages.
Examination Report on Australian Patent Application No. 2012216462 dated Mar. 6, 2014, 3 pages.
Final Office Action on U.S. Appl. No. 11/583,970 dated Apr. 9, 2014, 20 pages.
Gauss et al., "DEAE-Dextran Enhances Electroportation of Mammalian Cells", Nucleic Acids Research, vol. 20, No. 4, pp. 6739-6740 (1992).
Jayapal et al., "Down-regulation of Myc is Essential for Terminal Erythroid Maturation" The Journal of Biological Chemistry, vol. 285, No. 51, pp. 40252-40265, Dec. 17, 2010.
Non-Final Office Action on U.S. Appl. No. 12/701,383 dated Jun. 13, 2014, 26 pages.
Notice of Allowance on U.S. Appl. No. 12/550,166 dated Apr. 28, 2014, 4 pages.
Notification prior to Allowance of Israeli Patent Application No. 209343 dated Apr. 7, 2014, 2 pages.
Office Action on Canadian Application No. 2,626,525 dated Apr. 8, 2014, 4 pages.
Office Action on Canadian Patent Application No. 2,680,613 dated Nov. 21, 2013, 3 pages.
Rosenwald, et al., "Increased Expression of Eukaryotic Translation Inhibition Factors eIF-4E and eIF-2alpha in Response to Growth Induction by C-MYC", Proc. Natl. Acad. Sci. USA, vol. 90, pp. 6175-6178, (1993).
Wilson, et al. "c-MYC Controls the Balance Between Hematopoietic Stem Cell Self-Renewal and Differentiation" Genes and Development, vol. 18, pp. 2747-2763 (2007).

* cited by examiner

ANTIBODIES AND PROCESSES FOR PREPARING THE SAME

CROSS-REFERENCE

This application claims the benefit of U.S. Provisional Application No. 61/054,047, filed May 16, 2008, which application is incorporated herein by reference.

STATEMENT AS TO FEDERALLY SPONSORED RESEARCH

This invention was made with the support of the United States government under Contract number R01 CA117802 by the National Cancer Institute (NCI) of the National Institute of Health (NIH).

BACKGROUND OF THE INVENTION

Traditional approaches to generate antigen specific monoclonal antibodies are limited. Typically only a small representation of the highly diverse antigen-specific B-cell population is obtained. In some cases antigen specific B-cells fail to proliferate due to self-tolerance. In other cases, antigen specific B-cells fail to proliferate after cell fusion with a myeloma fusion partner.

SUMMARY OF THE INVENTION

Disclosed herein, in certain embodiments, are methods for generating, raising, obtaining and/or producing (for simplicity, the word "producing" as used herein is meant to equally refer to "generating," "raising," and "obtaining,"), a desired antibody are. In addition, systems, cell lines and organisms are described for use in producing a desired antibody. Further described are antibodies and compositions comprising such antibodies.

Provided herein are various methods for producing (a) antibody producing cells and (b) antibodies that overcome many of the problems associated with conventional antibody production. In certain embodiments, provided herein are methods for producing (a) antibody producing cells and (b) antibodies derived from cells (e.g., mammalian cells) that are that over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, provided herein is a method for (a) producing antibody producing cells and (b) antibodies derived from cells wherein MYC is over-expressed. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof. In certain embodiments, provided herein is a method for producing an antibody from an immuno-deficient organism (e.g., a mammal) wherein the organism's immune system is reconstituted with a plurality of hematopoietic stem cells that comprise an exogenous MYC gene (i.e., a MYC nucleic acid sequence (e.g., a transgenic sequence) that encodes a Myc peptide; i.e., transgenic MYC). Also provided herein is a method of producing a human or humanized antibody by introducing (or otherwise providing to) a human gene that encodes the human antibody into a cell (e.g., a mammalian cell) that comprises transgenic MYC. Certain embodiments, herein provide an isolated B-cell for producing a human or humanized antibody, wherein the B-cell over-expresses a MYC gene. In addition, provided herein is an isolated antibody prepared according to the any of the methods disclosed herein. Provided herein is also a cell that has been engineered to produce an antibody prepared according any of the methods disclosed herein.

In certain embodiments, provided herein are methods for producing antibodies (e.g., monoclonal antibodies) without the need for cell fusion. In some embodiments, the methods disclosed herein produce monoclonal antibody without the need to fuse antibody producing B cells with a fusion partner, thereby decreasing the time required to produce the antibody. Certain embodiments, described herein, provide for the production of antibodies specific for antigens that are normally subject to immunological constraints (e.g., self tolerance). For example, in some embodiments, the methods are used to produce monoclonal antibodies (i.e., mAB) to self antigens.

Provided herein is a method for producing an antibody specific for an antigen, comprising contacting a cell comprising transgenic MYC with a selected antigen. In some embodiments, the cell (e.g., a mammalian cell) expresses CD79 on its cell surface. In some embodiments, the cell (e.g., a mammalian cell) is a mammalian cell. In some embodiments, the cell (e.g., a mammalian cell) is a B-cell. In some embodiments, the transgenic MYC gene comprises an inducible promoter or a B-cell-selective promoter operably linked to an open reading frame (i.e., ORF) of the gene. In some embodiments, the B-cell selective promoter is the Eμ promoter. In some embodiments, the inducible promoter comprises one or more TREs. In some embodiments, the cell (e.g., a mammalian cell) is present in an organism (e.g., a mammal). In some embodiments, contacting the cell (e.g., a mammalian cell) with the selected antigen comprises administering (i.e., inoculating or introducing) the selected antigen to the organism (e.g., mammal). In some embodiments, the genome of the organism (e.g., a mammal) further comprises a nucleic acid sequence encoding a tetracycline reverse transcriptional activator (i.e., rtTA), a tetracycline transcriptional activator (i.e., tTA), or both. In some embodiments, a nucleic acid sequence encoding an rtTA comprises a B-cell-selective promoter operably linked to an open reading frame of the sequence. In some embodiments, a nucleic acid sequence encoding an rtTA comprises an MMTV promoter operably linked to an open reading frame of the sequence. In some embodiments, a nucleic acid sequence encoding a tTA comprises a B-cell-selective promoter operably linked to an open reading frame of the sequence. In some embodiments, a nucleic acid sequence encoding a tTA comprises an MMTV promoter operably linked to an open reading frame of the sequence.

In some embodiments, a method disclosed herein further comprises providing doxycycline, tetracycline, or an analog thereof to the organism (e.g., a mammal) for a period to sufficient to suppress tTA-dependent expression or rtTA-dependent expression of the transgenic MYC gene. In some embodiments, a method disclosed herein further comprises (a) providing doxycycline, tetracycline, or an analog thereof to the organism (e.g., a mammal) for a period to sufficient to suppress tTA-dependent expression or rtTA-dependent expression of the transgenic MYC gene, and (b) withdrawing the doxycycline, tetracycline, or analog thereof after the period a time sufficient induce tTA-dependent expression or rtTA-dependent expression of the transgenic MYC gene. In some embodiments, the organism further comprises an exogenous nucleic acid sequence encoding the selected antigen. In some embodiments, the method further comprises recovering from the organism one or more B-cells that express an antibody specific for the selected antigen. In some embodiments, the transgenic MYC gene encodes a Myc-ER polypeptide. In some embodiments, the transgenic MYC gene encodes a Myc-GR polypeptide. As used herein, "GR" means glucocorticoid receptor. In some embodiments, a Myc-ER polypeptide is translocated to the nucleus of a cell by contacting the cell (e.g., a mammalian cell) with an ER ligand. In some embodiments, the selected antigen is a self-antigen. In some embodiments, method comprises introducing (or otherwise providing to) an expression vector encoding the selected antigen.

Provided herein is a method for producing an antibody specific for an antigen, comprising administering (i.e., introducing or inoculating) a selected antigen to an organism (e.g., a mammal), wherein the organism (e.g., a mammal) comprises a transgenic MYC gene and an inducible promoter or a B-cell-selective promoter operably linked to an ORF of the MYC gene.

Provided herein is a method for producing an antibody specific for an antigen, comprising (a) providing a B-cell expressing an antibody that specifically binds to an antigen, wherein the B-cell comprises an transgenic MYC gene and/or an exogenous Myc peptide (e.g., a recombinant Myc peptide (e.g., a Myc fusion peptide as described herein)); and (b) inducing the expression of the MYC gene and/or the activity of the Myc peptide (e.g., a recombinant Myc peptide (e.g., a Myc fusion peptide as described herein)) in the B-cell. In some embodiments, the B-cell is prepared by contacting a B-cell comprising transgenic MYC gene and/or an exogenous Myc peptide (e.g., a recombinant Myc peptide (e.g., a Myc fusion peptide as described herein)) with the selected antigen. In some embodiments, a method disclosed herein further comprises expanding the B-cell to generate a monoclonal population of B-cells. In some embodiments, the method further comprises recovering the antibody from the population of monoclonal B-cells. In some embodiments, the B-cell is present in an organism (e.g., a mammal) and the induction of Myc activity occurs in vivo. In some embodiments, a method disclosed herein further comprises introducing (or otherwise providing to) a transgenic MYC gene or an exogenous Myc peptide (e.g., a recombinant Myc peptide (e.g., a Myc fusion peptide as described herein)) into the B-cell ex vivo prior to the inducing step. In some embodiments, a method disclosed herein further comprises introducing (or otherwise providing to) an exogenous Myc peptide (e.g., a recombinant Myc peptide (e.g., a Myc fusion peptide as described herein)) into the B-cell ex vivo. In some embodiments, the exogenous Myc peptide (e.g., a recombinant Myc peptide (e.g., a Myc fusion peptide as described herein)) comprises a protein transduction domain (e.g., a TAT domain). In some embodiments, the B-cell is an anergic B-cell. In some embodiments, the selected antigen is a self-antigen. In some embodiments, the transgenic MYC gene comprises a B-cell-selective promoter operably linked to an open reading frame of the gene. In some embodiments, the nucleic acid sequence (e.g., a transgenic sequence) comprises an inducible promoter operably linked to the open reading frame of the gene. In some embodiments, the inducible promoter comprises one or more TREs and the cell (e.g., a mammalian cell) further expresses a tTA peptide or an rtTA peptide. In some embodiments, the recombinant cell expresses the tTA peptide. In some embodiments, the exogenous Myc peptide (e.g., a recombinant Myc peptide (e.g., a Myc fusion peptide as described herein)) is a Myc-ER fusion peptide. In some embodiments, the inducing comprises contacting the B-cell with an ER ligand. In some embodiments, the exogenous Myc peptide (e.g., a recombinant Myc peptide (e.g., a Myc fusion peptide as described herein)) is a Myc-GR polypeptide. In some embodiments, the inducing comprises contacting the B-cell with a GR ligand. In some embodiments, the B-cell is a mouse B-cell. In some embodiments, the B-cell is from an organism (e.g., a mammal) that was administered (i.e., inoculated with or immunized with) the selected antigen. In some embodiments, the immunized organism comprises a transgenic MYC gene. In some embodiments, the transgenic MYC gene is inducible. In some embodiments, the transgenic MYC gene comprises a promoter, and wherein the promoter comprises one or more TREs. In some embodiments, the organism further carries and expresses a tTA nucleic acid sequence (e.g., a transgenic sequence) or an rtTA nucleic acid sequence (e.g., a transgenic sequence). In some embodiments, the organism further carries and expresses a gene (e.g., an exogenous gene) encoding the selected antigen.

Provided herein is a method for producing an antibody that specifically binds to an antigen, comprising administering to an immuno-deficient mammal a plurality of hematopoietic stem cells that comprise an transgenic MYC gene; and (c) administering (i.e., introducing, or inoculating) a selected antigen to the immuno-deficient mammal. In some embodiments, the hematopoietic stem cells further comprise an exogenous BCL-2 gene. In some embodiments, a method disclosed herein further comprises inducing a plurality of the hematopoietic stem cells to differentiate into B-cells. In some embodiments, a method disclosed herein further comprises recovering a plurality of B-cells that express the antibody from the immuno-deficient mammal. In some embodiments, a method disclosed herein further comprises recovering the antibody from the plurality of B-cells that express the antibody. In some embodiments, the transgenic MYC gene comprises an inducible promoter or a B-cell-selective promoter. In some embodiments, the transgenic MYC gene comprises an inducible promoter comprising one or more TREs. In some embodiments, the hematopoietic stem cells express tTA or rtTA. In some embodiments, a method disclosed herein further comprises (a) providing doxycycline, tetracycline, or an analog thereof to the immuno-deficient mammal for a period of time sufficient to suppress the tTA-dependent transactivation, and (b) withdrawing the doxycycline, tetracycline, or analog thereof after the period time in order to allow tTA-dependent transactivation. In some embodiments, the B-cell selective promoter is the Eµ promoter. In some embodiments, the transgenic MYC gene encodes a Myc-ER polypeptide. In some embodiments, a method disclosed herein further comprises (a) recovering at least one B-cell that express the antibody specific antigen from the immuno-deficient mammal; and (b) contacting the B-cell with an ER ligand. In some embodiments, the exogenous Myc peptide (e.g., a recombinant Myc peptide (e.g., a Myc fusion peptide as described herein)) is a Myc-GR polypeptide. In some embodiments, a method disclosed herein further comprises (a) recovering at least one B-cell that express the antibody specific antigen from the immuno-deficient mammal; and (b) contacting the B-cell with a GR ligand.

In some embodiments, the selected antigen is a self-antigen. In some embodiments, immuno-deficient organism is obtained by irradiating the organism (e.g., mammal). In some embodiments, the immuno-deficient organism (e.g., mammal) is a Rag-1ko, Rag-2, SCID, DNA-PK, Ku70, Ku80, XRCC4, or μMT mouse. In some embodiments, the immuno-deficient organism (e.g., mammal) expresses the selected antigen. In some embodiments, the immuno-deficient organism (e.g., mammal) comprises an exogenous DNA sequence that encodes the selected antigen. In some embodiments, the selected antigen is introduced into the organism's genome by transfection with a nucleic acid expression vector or infection with a viral expression vector. In some embodiments, the expression vector is a lentivirus.

Provided herein is a method for producing a human or humanized antibody comprising: providing a cell (e.g., a mammalian cell) that expresses human antibodies and comprises an exogenous DNA sequence that encodes a Myc peptide (e.g., a recombinant Myc peptide (e.g., a Myc fusion peptide as described herein)); and (b) contacting the cell (e.g., a mammalian cell) with a selected antigen. In some embodiments, the cell (e.g., a mammalian cell) is a B-cell. In some embodiments, the cell (e.g., a mammalian cell) inducibly over-expresses Myc. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof. In some embodiments, the cell (e.g., a mammalian cell) is present in an organism (e.g., mammal). In some embodiments, the method further comprises recovering the cell (e.g., a mammalian cell) from the organism (e.g., mammal). In some embodiments, the organism (e.g., mammal) is a mouse. In some embodiments, the organism (e.g., mammal) is an MMTV-tTA/TRE-MYC mouse. In some embodiments, the organism (e.g., mammal) is obtained by: (a) presenting an immuno-deficient organism (e.g., mammal); and (b) administering to the organism (e.g., mammal) a plurality of hematopoietic stem cells that over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof. In some embodiments, the immuno-deficient organism (e.g., mammal) is obtained by irradiating the organism (e.g., mammal). In some embodiments, the immuno-deficient organism (e.g., mammal) is a Rag-1ko, Rag-2, SCID, DNA-PK, Ku70, Ku80, XRCC4, or μMT mouse. In some embodiments, the organism (e.g., mammal) expresses the selected antigen. In some embodiments, a method disclosed herein further comprises recovering an antibody. In some embodiments, a method disclosed herein further comprises subjecting the cell (e.g., a mammalian cell) to conditions that induce over-expression of MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof. In some embodiments, the MYC DNA sequence comprises an inducible promoter or a B-cell-selective promoter. In some embodiments, prior to isolating the cell (e.g., a mammalian cell) from the organism (e.g., mammal) the cell (e.g., a mammalian cell) is subjected to conditions that induce over-expression of MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof.

In some embodiments, subsequent to isolating the antibody producing cell from the mammal the antibody producing cell is subjected to conditions that induce over-expression of MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof. In some embodiments, the mammal is an MMTV-rtTA/TRE-MYC; MMTV-rtTA/TRE-MYC/Rag-1−/−; MMTV-tTA/TRE-MYC; or MMTV-tTA/TRE-MYC/Rag-1−/− mouse and the conditions that induce over-expression of MYC are exposure to doxycycline, tetracycline, or an analog thereof. In some embodiments, the Myc peptide is a Myc-ER fusion peptide. In some embodiments, a method disclosed herein further comprises contacting the mammalian cell with an estrogen receptor ligand. In some embodiments, the mammalian cell is contacted with the selected antigen in the absence of an estrogen receptor ligand. In some embodiments, the Myc peptide is a Myc-GR fusion peptide. In some embodiments, a method disclosed herein further comprises contacting the mammalian cell with a glucocorticoid receptor ligand. In some embodiments, the mammalian cell is contacted with the selected antigen in the absence of an glucocorticoid receptor ligand.

Provided herein is a method for producing a human or humanized antibody comprising: (a) providing an human cell; (b) isolating a human gene that encodes the antibody from the human cell; and (c) introducing (or otherwise providing to) the gene into an cell that comprises an transgenic MYC gene or a exogenous Myc peptide (e.g., a recombinant Myc peptide (e.g., a Myc fusion peptide as described herein)). In some embodiments, the human gene encodes human IgH (immunoglobulin heavy chain) and IgL (immunoglobulin light chain), wherein the IgH and IgL together form an antibody that specifically binds the selected antigen. In some embodiments, the cell (e.g., a mammalian cell) is a B-cell. In some embodiments, a method disclosed herein further comprises transplanting the cell (e.g., a mammalian cell) into an organism (e.g., a mouse). In some embodiments, the human gene isolated encodes a first antibody and a second antibody. In some embodiments, a method disclosed herein further comprises recovering the antibody from the cell (e.g., a mammalian cell). In some embodiments, the transgenic MYC DNA sequence comprises an inducible promoter or a B-cell-selective promoter. In some embodiments, the exogenous Myc peptide (e.g., a recombinant Myc peptide (e.g., a Myc fusion peptide as described herein)) is a Myc-ER fusion peptide. In some embodiments, the Myc peptide is a Myc-GR fusion peptide.

Provided herein is a method for producing a human or humanized antibody comprising: (a) introducing (or otherwise providing to) a gene encoding a human immunoglobulin into a cell that over-expresses Myc; and (b) isolating the encoded human immunoglobulin. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof.

Provided herein are isolated B-cells for producing a human or humanized antibody, wherein the B-cells over-expresses Myc. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof. Also provided herein are isolated antibodies prepared according to the process of any of the methods disclosed herein. And further provided herein are mammalian cells that have been engineered to produce a recombinant form of any antibody prepared according the process of the methods disclosed herein.

Figure 1:
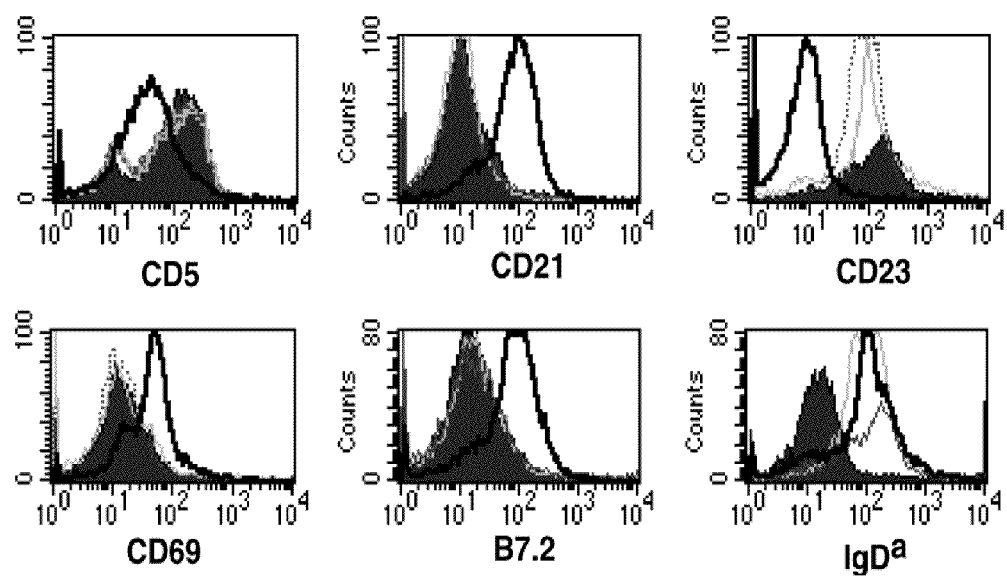
FIG. 1. An illustrative example of surface phenotype of tumors and cell lines that arise in Eµ-MYC/BCR$^{HEL}$/sHEL transgenic mice. The black filled histograms correspond to the profiles of cells obtained from wild type mice, the grey trace corresponds to the BCR$^{HEL}$ transgenic mice, the thin line or dotted trace correspond to BCR$^{HEL}$/sHEL mice, and the black trace correspond to the cells obtained from triply transgenic mice. The data represent the expression of the indicated markers on B220+ splenocytes.
Figure 2:
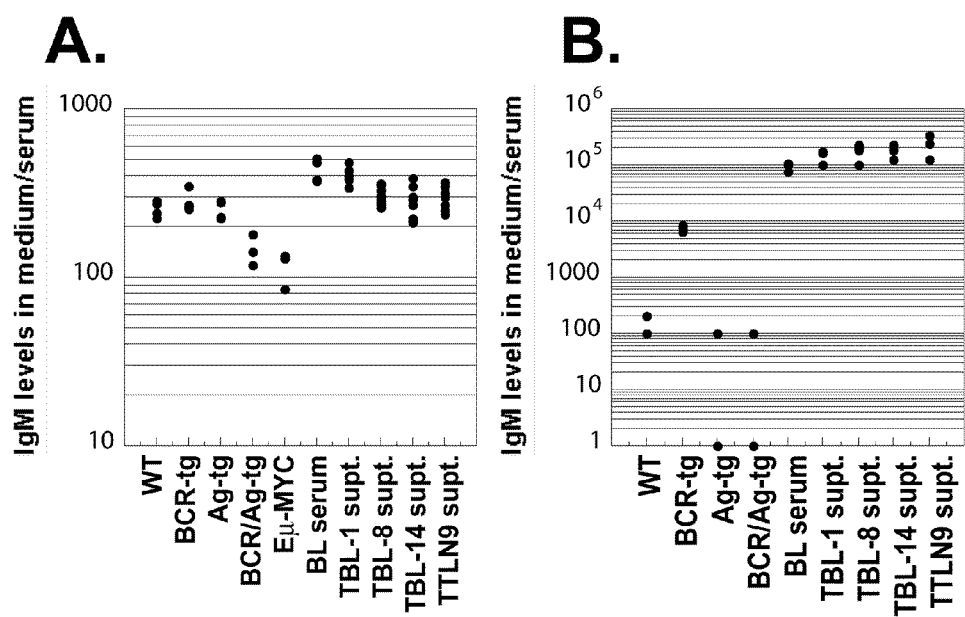
FIG. 2. An illustrative example of immunoglobulin production and HEL specific titers in tumors and cell lines that arise in Eµ-MYC/BCRHEL/sHEL mice. A defined number of cells ($10^5$) derived from each cell line (TBL-1, TBL-8, TBL-14 and TTLN9, all derived from the tumors that arose in Eµ-MYC/BCR$^{HEL}$/sHEL mice) were seeded in a 24 well plate, in 1 ml of growth medium, without any added cytokines. Samples of the supernatant were collected 4 days later and assayed for the concentration of total IgM (panel A), as well as for the titer of HEL specific IgM (panel B). Sera from various mice were used to compare antibody production to the cell lines. These mice included wild type C57/BL6 mice (WT), BCR$^{HEL}$ transgenic mice (BCR-tg), sHEL transgenic mice (Ag-tg), BCR$^{HEL}$/sHEL doubly transgenic mice (BCR/Ag-tg), Eµ-MYC mice and tumor-bearing Eµ-MYC/BCR$^{HEL}$/sHEL triply transgenic mice (BL). The results presented here are from one experiment, representative of three independent assays.
Figure 3:
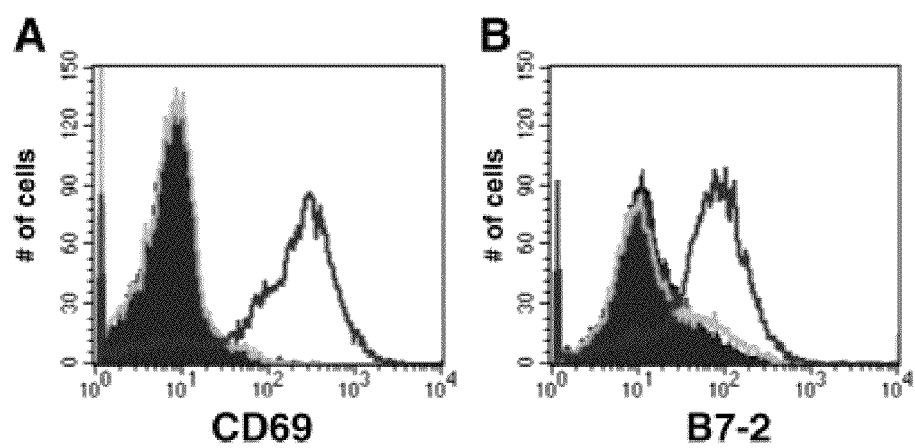
FIG. 3. Appearance of activated B-cells following acute overexpression of MYC. Flow cytometric detection of activated B-cells. Analyses were performed on lymph node cells obtained from a wild type mouse (black filled histogram), a MMTV-tTA/TRE-MYC/BCRHEL/sHEL mouse that had been kept on doxycycline throughout (grey trace), and an MMTV-tTA/TRE-MYC/BCRHEL/sHEL mouse that had been taken off doxycycline a week prior to euthanasia (black trace). Cells were stained with antibodies to two molecules that are upregulated following the selected antigen-dependent activation of B-cells, CD69 (A), and B7-2 (CD86) (B). The traces represent the levels of CD69 and B7-2 present on the B220+ fraction of the cells, ascertained by gating on the Cychrome-C staining cells by flow cytometry.
Figure 4:
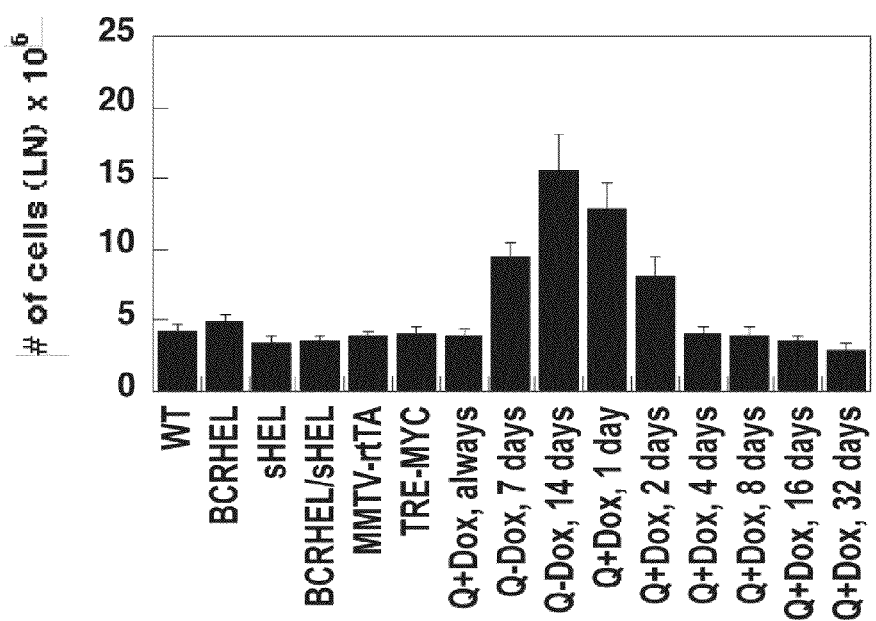
FIG. 4. Accumulation of activated B-cells requires the continuous overexpression of MYC. Activation of B-cells in response to MYC. The number of activated B-cells in lymph nodes was determined as described previously (34). Each data point in these graphs represents the number of activated B-cells detected in the lymph nodes of an individual mouse. Cohorts of four mice were used for each time point. This figure shows the requirement for MYC in the initiation and maintenance of the accumulation of activated B-cells in induced MMTV-tTA/TRE-MYC/BCRHEL/sHEL mice.
Figure 5:
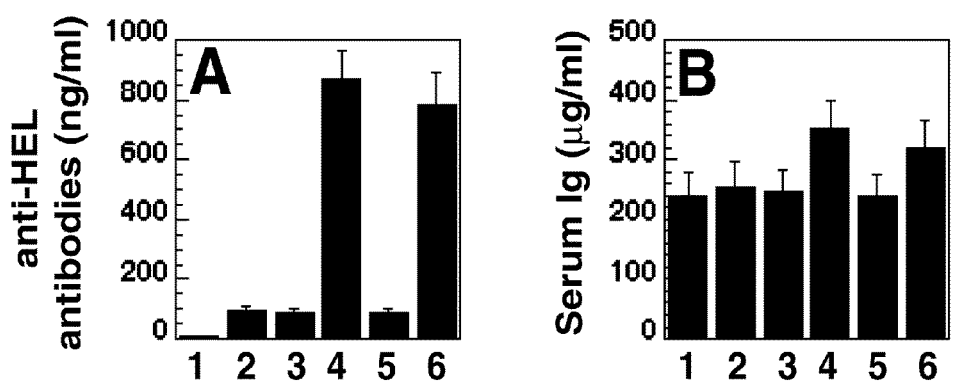
FIG. 5. Accumulation of autoantibodies in serum following the overexpression of MYC. Serological evidence of broken tolerance. Sera were obtained from groups of four mice of each of the specified genotypes, and assayed in triplicate by ELISA against HEL (A), or for total serum immunoglobulin (B). The numbered categories represent sera obtained from wild type mice (1), BCRHEL mice (2), BCRHEL/sHEL mice (3), Eµ-MYC/BCRHEL/sHEL mice prior to the development of overt tumors (4), MMTV-tTA/TRE-MYC/BCRHEL/sHEL mice that had been maintained on doxycycline throughout (5), and MMTV-tTA/TRE-MYC/BCRHEL/sHEL mice that had been taken off doxycycline 28 days prior to collection of sera (6).
Figure 6:
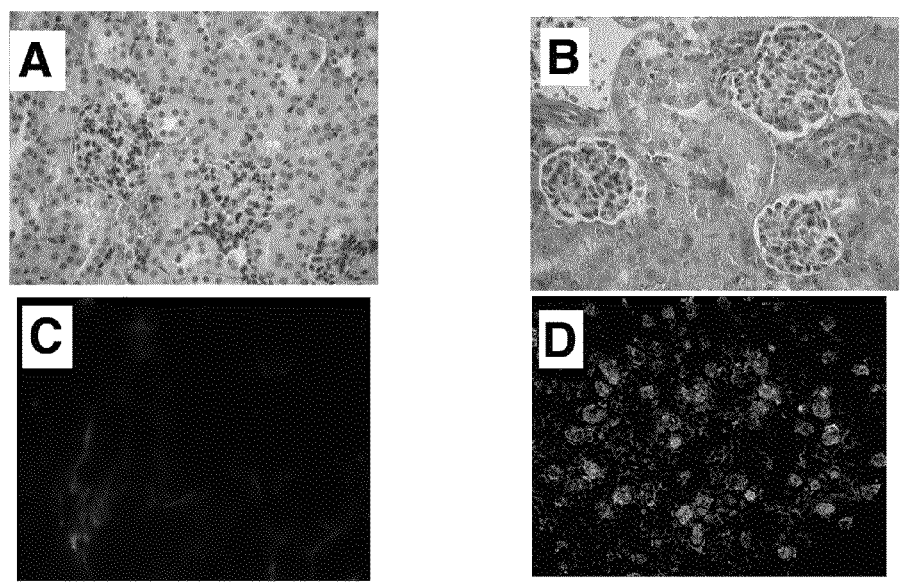
FIG. 6. Accumulation of autoantibodies and immune complexes in the kidneys following the overexpression of MYC. Kidneys were obtained from a wild type mouse (A) or an Eµ-MYC/BCRHEL/sHEL mouse (B) for histological examination. The tissues were sectioned and stained with hematoxylin and eosin, and microscopic images were obtained. Magnification was 100×. For immununofluorescence, kidneys were obtained from a wild type mouse (C) or an Eµ-MYC/BCRHEL/sHEL mouse (D). Frozen tissues were sectioned and stained with Rhodamine conjugated antibodies to IgM, as described in Materials and Methods. Magnification was 5×.

The term "lymphocyte" encompasses, by way of non-limiting example, B-cells, T-cells, NKT cells, and NK cells. In some embodiments, lymphocytes refers to all immature, mature, undifferentiated and differentiated white lymphocyte populations including tissue specific and specialized varieties. In some embodiments, lymphocytes include all B-cell lineages including pre-B-cells, Progenitor B cells, Early Pro-B cells, Late Pro-B cells, Large Pre-B cells, Small Pre-B cells, Immature B cells, Mature B cells, plasma B-cells, memory B-cells, B-1 cells, B-2 cells and anergic AN1/T3 cell populations.

The term B-cell, refers to, by way of non-limiting example, a pre-B-cell, Progenitor B cell, Early Pro-B cell, Late Pro-B cell, Large Pre-B cell, Small Pre-B cell, Immature B cell, Mature B cell, plasma B-cell, memory B-cell, B-1 cell, B-2 cells and anergic AN1/T3 cell populations. In some embodiments, the term B-cell includes a B-cell that expresses an immunoglobulin heavy chain and/or light chain on its cells surface. In some embodiments, the term B-cell includes a B-cell that expresses and secretes an immunoglobulin heavy chain and/or light chain. In some embodiments, the term B-cell includes a cell that binds an antigen on its cell-surface. In some embodiments, disclosed herein, B-cells or AN1/T3 cells are utilized in the processes described. In certain embodiments, such cells are optionally substituted with any animal cell suitable for expressing, capable of expressing (e.g., inducible expression), or capable of being differentiated into a cell suitable for expressing an antibody including, e.g., a hematopoietic stem cell, a B-cell, a pre-B-cell, a Progenitor B cell, a Early Pro-B cell, a Late Pro-B cell, a Large Pre-B cell, a Small Pre-B cell, an Immature B cell, a Mature B cell, a plasma B-cell, a memory B-cell, a B-1 cell, a B-2 cell, an anergic B-cell, or an anergic AN1/T3 cell.

The term "immunize" refers to the introduction of an antigen into an organism by any suitable method. Non-limiting examples of various routes are by way of intradermal injection, intravenous injection, intraocular administration, subcutaneous injection, intraperitoneal injection, oral administration, or topical administration.

The term "antigen" refers to a substance that is capable of inducing the production of an antibody. In some embodiments, an antigen is a substance that binds to an antibody variable region. In some embodiments, the selected antigen is a substance that is not native to the antibody-producing organism. In some embodiments, the selected antigen is a substance that is native to the antibody-producing organism (e.g., a self antigen).

The term "AN1/T3 cell populations" refers to an anergic population of B-cells; embodiments that describe AN1/T3 cell populations also include embodiments, in which the term AN1/T3 cell populations is replaced with the term "anergic population of B-cells."

The term "anergic" refers to a CD79 expressing cell that is not activated upon antigen binding. In some embodiments, activation is defined by the up-regulation of cell-surface CD79. In some embodiments, activation is defined by phosphorylation of CD79a and/or phosphorylation of Syk. In some embodiments, activation is defined by calcium mobilization.

The term "CD79" refers to the cell surface protein comprising either CD79a (Ig alpha) or CD79b (Ig beta).

The term "fusion protein" and "fusion peptide" are used interchangeably and refer to a contiguous polypeptide chain comprising at least two different proteins, parts of proteins or domains of proteins that are not normally found together in nature.

The terms "Myc", "cMyc", "Myc protein" and "Myc polypeptide" are used interchangeably and refer in certain instances to the NCBI Accession Number NP002458.2, functional homologs, analogs or fragments thereof. Synonyms of Myc include, but are not limited to c-Myc, v-Myc, Myc proto-oncogene protein & Transcription factor p64. In some embodiments, a Myc polypeptide comprises an amino acid sequence that is at least 40% to 100% identical, e.g., at least 40%, 45%. 50%, 55%, 60%, 65%, 70%, 75%, 80%, 85%, 86%, 87%, 88%, 90%, 91%, 92%, 94%, 95%, 96%, 97%, 98%, or any other percent from about 40% to about 100% identical to the sequence of NCBI Accession Numbers NP002458.2. In some embodiments, a Myc polypeptide comprises a polypeptide sequence of 40 amino acids or more in length that is at least 50% to 100% identical, e.g., at least 50%, 55%, 60%, 65%, 70%, 75%, 80%, 85%, 86%, 87%, 88%, 90%, 91%, 92%, 94%, 95%, 96%, 97%, 98%, or any other percent from about 50% to about 100% identical to the sequence of NCBI Accession Numbers NP002458.2. In some embodiments, a Myc polypeptide comprises a polypeptide sequence of 40 amino acids or more in length that is at least 50% to 100% identical, e.g., at least 50%, 55%, 60%, 65%, 70%, 75%, 80%, 85%, 86%, 87%, 88%, 90%, 91%, 92%, 94%, 95%, 96%, 97%, 98%, or any other percent from about 50% to about 100% identical to the sequence of NCBI Accession Numbers NP002458.2 wherein the Myc polypeptide promotes cell viability, cell immortality, cell growth and/or cell proliferation. Furthermore, the function of an onco-peptide as used herein refers to one or more of the promotion of cell viability, cell immortality, cell growth and/or cell proliferation. In several embodiments, disclosed herein, Myc is utilized as an illustrative example of an onco-peptide with onco-peptide function. It is to be understood that in those embodiments, disclosed herein, the Myc is optionally substituted with any suitable onco-peptide, analog, homolog, or fragment thereof that promotes cell viability, cell immortality, cell growth and/or cell proliferation.

"MYC" refers to a nucleic acid encoding a Myc peptide (e.g., a recombinant Myc peptide (e.g., a Myc fusion peptide as described herein)).

A MYC gene comprises a nucleotide sequence of at least 120 nucleotides that is at least 60% to 100% identical or homologous, e.g., at least 60, 65%, 70%, 75%, 80%, 85%, 86%, 87%, 88%, 90%, 91%, 92%, 94%, 95%, 96%, 97%, 98%, or any other percent from about 70% to about 100% identical to sequences of NCBI Accession Number NM_002467.

"Myc-ER" refers to a Myc peptide fused to a modified hormone binding domain of the estrogen receptor (ER). When exposed to 4-hydroxytamoxifen or other estrogen analogs, the Myc-ER polypeptide is triggered to translocate into the nucleus of the cell.

"Myc-ER" refers to a transgene encoding a Myc-ER polypeptide.

"Myc-GR" refers to a Myc peptide fused to a modified hormone binding domain of the glucocorticoid receptor (GR).

"MYC-GR" refers to a transgene encoding a Myc-GR polypeptide.

To determine the percent homology of two amino acid sequences or of two nucleic acids, the sequences can be aligned for optimal comparison purposes (e.g., gaps are introduced in the sequence of a first amino acid or nucleic acid sequence for optimal alignment with a second amino or nucleic acid sequence). The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position. The percent homology between the two sequences is a function of the number of identical positions shared by the sequences (i.e., % identity=# of identical positions/total # of positions (e.g., overlapping positions)×100). In some embodiments, the two sequences are the same length.

To determine percent homology between two sequences, the algorithm of Karlin and Altschul (1990) Proc. Natl. Acad. Sci. USA 87:2264-2268, modified as in Karlin and Altschul (1993) Proc. Natl. Acad. Sci. USA 90:5873-5877 is used. Such an algorithm is incorporated into the NBLAST and XBLAST programs of Altschul, et al. (1990) J. Mol. Biol. 215:403-410. BLAST nucleotide searches are performed with the NBLAST program, score=100, wordlength=12 to obtain nucleotide sequences homologous to a nucleic acid molecules described or disclose herein. BLAST protein searches are performed with the XBLAST program, score=50, wordlength=3. To obtain gapped alignments for comparison purposes, Gapped BLAST is utilized as described in Altschul et al. (1997) Nucleic Acids Res. 25:3389-3402. When utilizing BLAST and Gapped BLAST programs, the default parameters of the respective programs (e.g., XBLAST and NBLAST) are used. See the website of the National Center for Biotechnology Information for further details (on the World Wide Web at ncbi.nlm.nih.gov). Proteins suitable for use in the methods described herein also includes proteins having between 1 to 15 amino acid changes, e.g., 1, 2, 3, 4, 5, 6, 7, 8, 9, 10, 11, 12, 13, 14, or 15 amino acid substitutions, deletions, or additions, compared to the amino acid sequence of any protein described herein. In other embodiments, the altered amino acid sequence is at least 75% identical, e.g., 77%, 80%, 82%, 85%, 88%, 90%, 92%, 95%, 97%, 98%, 99%, or 100% identical to the amino acid sequence of any protein inhibitor described herein. Such sequence-variant proteins are suitable for the methods described herein as long as the altered amino acid sequence retains sufficient biological activity to be functional in the compositions and methods described herein. Where amino acid substitutions are made, the substitutions should be conservative amino acid substitutions. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff et al (1992), *Proc. Natl Acad. Sci. USA,* 89: 10915-10919). Accordingly, the BLOSUM62 substitution frequencies are used to define conservative amino acid substitutions that, in some embodiments, are introduced into the amino acid sequences described or disclosed herein. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

The term "expression" refers to one or more of the following events: (1) production of RNA from a DNA sequence (e.g., by transcription) within a cell; (2) processing of an RNA transcript (e.g., by splicing, editing, 5' cap formation, and/or 3' end formation) within a cell; (3) translation of RNA into a polypeptide or protein within a cell; (4) post-translational modification of a polypeptide or protein within a cell; (5) presentation of a polypeptide or protein on the cell surface; (6) secretion or release of a polypeptide or protein from a cell.

The term "over-expression", refers to a higher level of expression when compared to the endogenous level of expression of an identical polypeptide or protein within the same cell. In certain instances, "over-expression" refers to recombinant expression of a polypeptide. In some embodiments, a higher level of expression comprises 2% to 200% higher. In some embodiments, a higher level of expression comprises 2-fold to 1000-fold higher. In some embodiments, a higher level of expression comprises 2-fold to 1000-fold higher. In some embodiments, a higher level of expression comprises 2-fold to 10,000-fold higher. In some embodiments, a higher level of expression comprises a detectable level of expression when compared to a previous undetectable level of expression. In some embodiments, "over-expression" refers to any detectable level of expression of an exogenous polypeptide or protein.

The phrase "over-expression of MYC" refers to over-expression of a Myc peptide (e.g., a recombinant Myc peptide (e.g., a Myc fusion peptide as described herein)) or a Myc peptide (e.g., a recombinant Myc peptide (e.g., a Myc fusion peptide as described herein)) fused to another peptide. In some embodiments, "over-expression of MYC" refers to over-expression of MYC-ER. In some embodiments, "over-expression of MYC" refers to over-expression of MYC-GR. In some embodiments, "over-expression of MYC" refers to over-expression of a fragment of a Myc-polypeptide that contains the DNA binding domain of Myc. In some embodiments, "over-expression of MYC" refers to over-expression of a polypeptide that comprises the DNA binding domain of Myc.

The terms "antibody" and "antibodies" refer to monoclonal antibodies, polyclonal antibodies, bi-specific antibodies, multispecific antibodies, grafted antibodies, human antibodies, humanized antibodies, synthetic antibodies, chimeric antibodies, camelized antibodies, single-chain Fvs (scFv), single chain antibodies, Fab fragments, F(ab') fragments, disulfide-linked Fvs (sdFv), intrabodies, and anti-idiotypic (anti-Id) antibodies and antigen-binding fragments of any of the above. In particular, antibodies include immunoglobulin molecules and immunologically active fragments of immunoglobulin molecules, i.e., molecules that contain an antigen binding site. Immunoglobulin molecules are of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass. The terms "antibody" and immunoglobulin are used interchangeably in the broadest sense. The subunit structures and three-dimensional configurations of the different classes of immunoglobulins are well known in the art. In some embodiments, an antibody is part of a larger molecule, formed by covalent or non-covalent association of the antibody with one or more other proteins or peptides.

The term "derivative" in the context of a polypeptide or protein, e.g. an antibody, refers to a polypeptide or protein that comprises an amino acid sequence which has been altered by the introduction of amino acid residue substitutions, deletions or additions. The term "derivative" also refers to a polypeptide or protein which has been modified, i.e., by the covalent attachment of any type of molecule to the antibody. For example, in some embodiments, a polypeptide or protein is modified, e.g., by glycosylation, acetylation, pegylation, phosphorylation, amidation, derivatization by protecting/blocking groups, proteolytic cleavage, linkage to a cellular ligand or other protein, etc. In some embodiments, derivatives, polypeptides or proteins are produced by chemical modifications using suitable techniques, including, but not limited to specific chemical cleavage, acetylation, formylation, metabolic synthesis of tunicamycin, etc. In some embodiments, a derivative a polypeptide or protein possesses a similar or identical function as the polypeptide or protein from which it was derived.

The terms "full length antibody", "intact antibody" and "whole antibody" are used herein interchangeably, to refer to an antibody in its substantially intact form, and not antibody fragments as defined below. These terms particularly refer to an antibody with heavy chains contains Fc regions. In some embodiments, an antibody variant provided herein is a full length antibody. In some embodiments, the full length antibody is human, humanized, chimeric, and/or affinity matured.

An "affinity matured" antibody is one having one or more alteration in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by suitable procedures. See, for example, Marks et al., (1992) *Biotechnology* 10:779-783 that describes affinity maturation by variable heavy chain (VH) and variable light chain (VL) domain shuffling. Random mutagenesis of CDR and/or framework residues is described in: Barbas, et al. (1994) *Proc. Nat. Acad. Sci, USA* 91:3809-3813; Shier et al., (1995) *Gene* 169:147-155; Yelton et al., 1995, *J. Immunol.* 155:1994-2004; Jackson et al., 1995, *J. Immunol.* 154(7):3310-9; and Hawkins et al, (19920, *J. Mol. Biol.* 226:889-896, for example.

The terms "binding fragment", "antibody fragment" or "antigen binding fragment" are used herein, for purposes of the specification and claims, to mean a portion or fragment of an intact antibody molecule, preferably wherein the fragment retains antigen-binding function. Examples of antibody fragments include Fab, Fab', F(ab')$_2$, Fd, Fd' and Fv fragments, diabodies, linear antibodies (Zapata et al. (1995) *Protein Eng.* 10: 1057), single-chain antibody molecules, single-chain binding polypeptides, scFv, bivalent scFv, tetravalent scFv, and bispecific or multispecific antibodies formed from antibody fragments.

"Fab" fragments are typically produced by papain digestion of antibodies resulting in the production of two identical antigen-binding fragments, each with a single antigen-binding site and a residual "Fc" fragment. Pepsin treatment yields a F(ab')2 fragment that has two antigen-combining sites capable of cross-linking antigen. An "Fv" is the minimum antibody fragment that contains a complete antigen recognition and binding site. In a two-chain Fv species, this region consists of a dimer of one heavy- and one light-chain variable domain in tight, non-covalent association. In a single-chain Fv (scFv) species, one heavy- and one light-chain variable domain are covalently linked by a flexible peptide linker such that the light and heavy chains associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although usually at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy-chain $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also suitable. Methods for producing the various fragments from monoclonal Abs include, e.g., Plückthun, 1992, Immunol. Rev. 130:152-188.

The term "monoclonal antibody" refers to an antibody obtained from a population of substantially homogeneous antibodies, i.e., the individual antibodies comprising the population are identical except for possible naturally occurring mutations that are present in minor amounts. In some embodiments, monoclonal antibodies are made, for example, by the hybridoma method first described by Köhler and Milstein (1975) *Nature* 256:495, or are made by recombinant methods, e.g., as described in U.S. Pat. No. 4,816,567. In some embodiments, monoclonal antibodies are isolated from phage antibody libraries using the techniques described in Clackson et al., *Nature* 352:624-628 (1991), as well as in Marks et al., *J. Mol. Biol.* 222:581-597 (1991).

The antibodies herein include monoclonal, polyclonal, recombinant, chimeric, humanized, bi-specific, grafted, human, and fragments thereof including antibodies altered by any means to be less immunogenic in humans. Thus, for example, the monoclonal antibodies and fragments, etc., herein include "chimeric" antibodies and "humanized" antibodies. In general, chimeric antibodies include a portion of the heavy and/or light chain that is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, so long as they exhibit the desired biological activity (U.S. Pat. No. 4,816,567); Morrison et al. *Proc. Natl Acad. Sci.* 81:6851-6855 (1984). For example in some embodiments, a chimeric antibody contains variable regions derived from a mouse and constant regions derived from human in which the constant region contains sequences homologous to both human IgG2 and human IgG4. Numerous methods for preparing "chimeric" antibodies, etc., are known in the art. "Humanized" forms of non-human (e.g., murine) antibodies or fragments are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include, grafted antibodies or CDR grafted antibodies wherein part or all of the amino acid sequence of one or more complementarity determining regions (CDRs) derived from a non-human animal antibody is grafted to an appropriate position of a human antibody while maintaining the desired binding specificity and/or affinity of the original non-human antibody. In some embodiments, corresponding non-human residues replace Fv framework residues of the human immunoglobulin. In some embodiments, humanized antibodies comprise residues that are found neither in the recipient antibody nor in the imported CDR or framework sequences. These modifications are made to further refine and optimize antibody performance. In some embodiments, the humanized antibody comprises substantially all of at least one, and typically two, variable domains, in which all or substantially all of the CDR regions correspond to those of a non-human immunoglobulin and all or substantially all of the FR regions are those of a human immunoglobulin consensus sequence. For further details, see, e.g.: Jones et al., Nature 321: 522-525 (1986); Reichmann et al., Nature 332: 323-329 (1988) and Presta, Curr. Op. Struct. Biol. 2: 593-596 (1992). Numerous methods for "humanizing" antibodies, etc., are known in the art.

The term "vector" or "expression vector" is used herein to mean vectors used as suitable vehicles for introducing (or otherwise providing to) into and/or expressing a desired gene in a host cell. Examples of vectors include but are not limited to plasmids, phages, viruses and retroviruses. In some embodiments, suitable vectors comprise a selection marker. In some embodiments, suitable vectors comprise restriction sites to facilitate cloning of the desired gene and in some embodiments, suitable vectors comprise the ability to enter and/or replicate in eukaryotic or prokaryotic cells.

Numerous expression vector systems are optionally utilized in a method disclosed herein. For example, one class of vector utilizes DNA elements that are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. In some embodiments, cells that have integrated exogenous DNA into their chromosomes are selected by introducing (or otherwise providing to) one or more selection markers into the transfected host cells. In some embodiments, the selection markers provide for prototrophy to an auxotrophic host, biocide resistance (e.g., antibiotics) or resistance to heavy metals such as copper. In some embodiments, the selectable marker gene is either directly linked to the DNA sequences to be expressed, or is introduced into the same cell by cotransformation. In some embodiments, additional regulatory elements are incorporated in the vector for optimal transcription. Examples of regulatory elements include signal sequences, splice signals, as well as transcriptional promoters, enhancers, and termination signals.

In some embodiments, the nucleic acids described herein include a promoter comprising a tetracycline response element and a transgene that constitutively expresses either rtTA (reverse tetracycline transactivator) or tTA (tetracycline-controlled transactivator). The rtTA protein binds to a TRE and activates transcription only in the presence of tetracycline, doxycycline or an analogue thereof. The tTA protein, in the presence of tetracycline, doxycycline or an analogue thereof, binds to a TRE thereby inhibiting transcription. In the absence of tetracycline, doxycycline or an analogue thereof tTA allows transcription.

The term "epitope" refers to a fragment of a polypeptide or protein having antigenic or immunogenic activity in an organism, preferably in a mammal, and most preferably in a human. An epitope having immunogenic activity is a fragment of a polypeptide or protein that elicits an antibody response in an animal. An epitope having antigenic activity is a fragment of a polypeptide or protein to which an antibody immunospecifically binds as determined by any known method, for example by immunoassays. Antigenic epitopes need not necessarily be immunogenic.

The phrase "specifically binds" when referring to the interaction between an antibody or other binding molecule and a protein or polypeptide or epitope, typically refers to an antibody or other binding molecule that recognizes and detectably binds with high affinity to the target of interest. Preferably, under designated or physiological conditions, the specified antibodies or binding molecules bind to a particular polypeptide, protein or epitope yet does not bind in a significant or undesirable amount to other molecules present in a sample. In other words the specified antibody or binding molecule does not undesirably cross-react with non-target antigens and/or epitopes. A variety of immunoassay formats are used to select antibodies or other binding molecule that are immunoreactive with a particular polypeptide and have a desired specificity. For example, solid-phase ELISA immunoassays, BIAcore, flow cytometry and radioimmunoassays are used to select monoclonal antibodies having a desired immunoreactivity and specificity. See, Harlow, 1988, ANTIBODIES, A LABORATORY MANUAL, Cold Spring Harbor Publications, New York (hereinafter, "Harlow"), for a description of immunoassay formats and conditions that are used to determine or assess immunoreactivity and specificity.

"Selective binding", "selectivity", and the like refer the preference of an antibody to interact with one molecule as compared to another. Preferably, interactions between antibodies, particularly modulators, and proteins are both specific and selective. Note that in some embodiments, an antibody is designed to "specifically bind" and "selectively bind" two distinct, yet similar targets without binding to other undesirable targets.

The term "endogenous" in the context of a cellular protein refers to protein naturally occurring and/or expressed by the cell in the absence of recombinant manipulation; accordingly, the terms "endogenously expressed protein" or "endogenous protein" excludes cellular proteins expressed by means of recombinant technology.

The terms "polypeptide", peptide" and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins (i.e., antigens), wherein the amino acid residues are linked by covalent peptide bonds.

The term "onco-peptide" and "oncoprotein" are utilized interchangeably herein and refer to a polymer of amino acid residues, fragments or analogs thereof, that are encoded by oncogenes or proto-oncogenes. In certain instances, oncopeptides promote cell survival and/or cell proliferation.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, pro line, serine, threonine, tryptophan, tyro sine, and valine) and pyrolysine and selenocysteine. Amino acid analogs refers to agents that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions are achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Cassol et al. (1992); Rossolini et al., Mol. Cell. Probes 8:91-98 (1994)).

The terms "isolated" and "purified" refer to a material that is substantially or essentially removed from or concentrated in its natural environment. For example, an isolated nucleic acid is one that is separated from at least some of the nucleic acids that normally flank it or other nucleic acids or components (proteins, lipids, etc. . . . ) in a sample. In another example, a polypeptide is purified if it is substantially removed from or concentrated in its natural environment. Methods for purification and isolation of nucleic acids and proteins are documented methodologies. Embodiments, of "substantially" include at least 20%, at least 40%, at least 50%, at least 75%, at least 85%, at least 90%, at least 95%, or at least 99%.

The phrase "recombinant nucleic acid" refers to a nucleic acid that is engineered through the combination or insertion of one or more nucleic acids, thereby combining sequences that would not normally occur together in nature. In some embodiments, recombinant nucleic acids comprise promoters or enhances. In some embodiments, recombinant nucleic acids comprise restriction enzyme sites. In some embodiments, recombinant nucleic acids encode polypeptides. In some embodiments, recombinant nucleic acids comprise mutations.

The term "recombinant polypeptide" refers to a polypeptide that is produced from a recombinant nucleic acid. In some embodiments, the recombinant polypeptide is a Myc fusion peptide. In some embodiments, the recombinant polypeptide is a TAT-Myc fusion peptide as described herein.

The term "recombinant Myc polypeptide" comprises a Myc polypeptide that is produced from a recombinant nucleic acid. In some embodiments, the recombinant Myc polypeptide is a Myc fusion peptide. In some embodiments, the recombinant Myc polypeptide is a TAT-Myc fusion peptide as described herein.

The term "recombinant Myc activity" refers to the binding of a recombinant Myc polypeptide to DNA located in the nucleus of the cell wherein the recombinant Myc regulates the transcriptional activity of Myc responsive genes.

The term "transgene" refers to an exogenous gene introduced into the genome of an organism.

The term "transgenic animal" refers to an animal that carries a transgene.

The term "genetically altered" refers to an animal, bacteria, virus or cell comprising a recombinant nucleic acid.

The term "self antigen" refers to an antigen that originates from within an animal, tissue, or cell. In some embodiments, a self antigen comprises an endogenous antigen. In some embodiments, a self antigen comprises an endogenous antigen produced by an endogenous retrovirus. In some embodiments, self antigens comprise neo-self antigens, microbially or parasite encoded neo-self antigens, or other neo-self antigens expressed as a result of genetic alteration to an animal or cell. In some embodiments, a chimeric mouse expresses a neo-self antigen.

The term "auto antigen" refers to an antigen that comprises an epitope of a self antigen or an immunologically reactive epitope that mimics that of a self antigen. In some embodiments, the term auto antigen comprises antigens to which autoantibodies are produced. In some embodiments, an auto antigen comprises an endogenous antigen wherein the animal from which the endogenous antigen originated is or was once immunologically tolerant to the selected antigen.

The term "neo-self antigen" refers to an antigen that is introduced into an organism via use of a retrovirus. In some embodiments, a retrovirus is used to overexpress a protein in a stem cell and those cells are transplanted into an organism. In some embodiments, the protein is viewed by the chimaeric's animal immune system as a self antigen.

The term "Myc activity" refers to binding of a Myc peptide (e.g., a recombinant Myc peptide (e.g., a Myc fusion peptide as described herein)) to DNA in the nucleus of a cell wherein Myc regulates the transcriptional activity of Myc responsive genes. In some embodiments, Myc activity induces cell proliferation and/or antibody production.

The term "activation of Myc" and "Myc activation" refers to the induction of Myc activity. In some embodiments, activation of Myc is induced by over-expression of a Myc peptide (e.g., a recombinant Myc peptide (e.g., a Myc fusion peptide as described herein)). In some embodiments, activation of Myc is induced by transport of a Myc peptide (e.g., a recombinant Myc peptide (e.g., a Myc fusion peptide as described herein)) into the nucleus of a cell. In some embodiments, activation of Myc is induced by transport of a Myc peptide (e.g., a recombinant Myc peptide (e.g., a Myc fusion peptide as described herein)) into a cell.

The term "TRE" refers to a tetracycline response element.

The term "immortal" refers the ability of a cell to proliferate in culture over multiple generations with a minimal loss of viability of the overall population. In some embodiments, immortal cells are considered transformed cells. In some embodiments, immortal cells are considered malignant. In some embodiments, immortal B-cell are referred to as lymphomas. In the absence of genetic alteration, mutation, modification, or viral infection, native primary cells and primary B-cells are, in some embodiments, not immortal and will lose viability after a few passages in culture.

As used herein, "xenomouse" means a mouse that is genetically altered to express one or more non-native genes. In some embodiments, a xenomouse is genetically altered to produce human antibodies.

"Transporter peptide" and "peptide transduction domain" (PTD) are interchangeable. As used herein, the terms mean a peptide sequence that promotes peptide penetration into cells and tissues. In some embodiments, a transporter peptide is TAT. In some embodiments, a transporter peptide is TAT$_{[48-57]}$. In some embodiments, a transporter peptide is TAT$_{[57-48]}$. In some embodiments, the transporter peptide is HIV-Vpr, HSV-Vp22, antennapedia, the chariot system, or a combination thereof. For examples of transporter peptides, see U.S. application Ser. No. 11/583,970 (Pub. No. 2007-0116691), which is herein incorporated by reference for such disclosures.

As used herein, a "MYC sequence" is a MYC amino acid peptide sequence. In some embodiments, the MYC peptide is a complete MYC peptide sequence. In some embodiments, the MYC peptide is a partial MYC peptide sequence. In some embodiments, the MYC is c-MYC. In some embodiments, the MYC peptide sequence comprises:

```
                                            (SEQ ID NO. 1)
MDFFRVVENQQPPATMPLNVSFTNRNYDLDYDSVQPYFYCDEEENFYQQQ

QQSELQPPAPSEDIWKKFELLPTPPLSPSRRSGLCSPSYVAVTPFSLRGD

NDGGGGSFSTADQLEMVTELLGGDMVNQSFICDPDDETFIKNIIQDCMW

SGFSAAAKLVSEKLASYQAARKDSGSPNPARGHSVCSTSSLYLQDLSAAA

SECIDPSVVFPYPLNDSSSPKSCASQDSSAFSPSSDSLLSSTESSPQGSP

EPLVLHEETPPTTSSDSEEEQEDEEEIDVVSVEKRQAPGKRSESGSPSAG

GHSKPPHSPLVLKRCHVSTHQHNYAAPPSTRKDYPAAKRVKLDSVRVLRQ

ISNNRKCTSPRSSDTEENVKRRTHNVLERQRRNELKRSFFALRDQIPELE

NNEKAPKVVILKKATAYILSVQAEEQKLISEEDLLRKRREQLKHKLEQLR

KGELNSKLE.
```

Processes for Preparing Antibodies

In some embodiments, provided herein is a method of producing an antibody that specifically binds to an antigen, comprising: contacting a cell comprising a nucleic acid sequence (e.g., a transgenic sequence) encoding an onco-peptide (e.g., MYC) or an onco-peptide (e.g., recombinant onco-peptide; e.g., TAT-Myc) with a selected antigen. In some embodiments, the onco-peptide is a fusion peptide. In some embodiments, the onco-peptide is a fusion peptide comprising a PTD. In some embodiments, the onco-peptide is TAT-MYC. In some embodiments, the onco-peptide is Myc-ER. In some embodiments, the onco-peptide is Myc-GR.

In some embodiments, the onco-peptide is a peptide that promotes cell survival and/or proliferation. In certain embodiments, the cell is a mammalian cell. In some embodiments, the cell is a human cell. In some embodiments, the cell is a B-cell. In some embodiments, the cell is a hematopoietic cell. In some embodiments, the cell is a human B-cell. In some embodiments, the cell is a human hematopoietic cell. In some embodiments, the cell (e.g., a mammalian cell) expresses CD79 on its cell surface. In some embodiments, the cell (e.g., a mammalian cell) comprises an intact salvage pathway for purine biosynthesis and is tolerant and/or anergic to the selected antigen. In some embodiments, the cell (e.g., a mammalian cell) is a B-cell, a B-cell precursor or progenitor, or a hematopoietic stem cell. In certain embodiments, the antibody specifically binds to the selected antigen. In certain embodiments, the onco-peptide is a peptide that promotes cell survival and/or proliferation.

In certain embodiments, the cell (e.g., a mammalian cell) is contacted with the selected antigen by any suitable method. In specific embodiments, the cell (e.g., a mammalian cell) comprises a nucleic acid sequence (e.g., a transgenic sequence) that encodes the selected antigen and is, thereby, contacted with the selected antigen. In some embodiments, the selected antigen is a self-antigen.

In certain embodiments, wherein a B-cell precursor or progenitor or a hematopoietic stem cell are used, a method described herein further comprises allowing or inducing differentiation of the cell (e.g., a mammalian cell) to a B-cell.

In some embodiments, a MYC sequence (e.g., a transgenic sequence) further comprises a B-cell selective promoter or an inducible promoter. In some embodiments, a nucleic acid sequence (e.g., a transgenic sequence) encoding the selected antigen further comprises a B-cell selective promoter or an inducible promoter. In some embodiments, a B-cell selective promoter is, by way of non-limiting example, the Eµ promoter. In some embodiments, the inducible promoter comprises, by way of non-limiting example, one or more TREs. In certain embodiments, the cell (e.g., a mammalian cell) further comprises a nucleic acid sequence (e.g., a transgenic sequence) that encodes a nucleic acid sequence (e.g., a transgenic sequence) encoding a tTA peptide or an rtTA peptide. In some embodiments, the nucleic acid sequence (e.g., a transgenic sequence) encoding the tTA peptide or the rtTA peptide comprises a B-cell-selective promoter operably linked to the open reading frame encoding the tTA peptide or the rtTA peptide. In some embodiments, the nucleic acid sequence (e.g., transgenic nucleic acid sequence) encoding the tTA peptide or the rtTA peptide comprises the MMTV promoter operably linked to the open reading frame encoding the tTA peptide or the rtTA peptide. Furthermore, in some embodiments, wherein an inducible promoter comprises one or more TREs, a method described herein further comprises contacting the cell (e.g., a mammalian cell) with doxycycline, tetracycline, or an analog thereof.

In some embodiments, the onco-peptide is a fusion peptide that comprises a receptor that activates the onco-peptide activity (e.g., cell survival and/or proliferation) when bound with a ligand. In some embodiments, the receptor is an estrogen receptor (ER). In specific embodiments, the onco-peptide is a Myc-ER fusion peptide. In specific embodiments, the onco-peptide is a Myc-GR fusion peptide. In certain embodiments, a method described herein further comprises contacting a cell comprising a recombinant onco-peptide that is a fusion peptide comprising a receptor with a ligand that binds the receptor. In specific embodiments, a method described herein further comprises contacting the cell (e.g., a mammalian cell) comprising a Myc-ER fusion peptide with an estrogen receptor modulator (e.g., an ER agonist or antagonist). In specific embodiments, a method described herein further comprises contacting the cell (e.g., a mammalian cell) comprising a Myc-GR fusion peptide with a glucocorticoid receptor modulator (e.g., a GR agonist or antagonist).

In some embodiments, the onco-peptide is a fusion peptide that comprises a (a) a transporter peptide sequence (e.g., TAT); and (b) a MYC sequence (e.g., c-MYC). In some embodiments, the fusion peptide is a peptide of Formula (I):

transporter peptide sequence-MYC sequence.

In some embodiments, a fusion peptide disclosed herein comprises (a) a transporter peptide sequence; (b) a MYC sequence; and (c) one or more molecules that link the transporter peptide sequence and the MYC sequence (i.e., "X"). In some embodiments, the fusion peptide is a peptide of Formula (II):

transporter peptide sequence-X-MYC sequence, wherein -X- is molecule that links the transporter peptide sequence and the MYC sequence. In some embodiments, -X- is an amino acid. In some embodiments, -X- is at least one amino acid.

In certain embodiments, a method described herein further comprises inducing MYC expression, Myc activity, or a combination thereof, in the cell (e.g., a mammalian cell). In some embodiments, a method described herein further comprises proliferating or inducing proliferation of the cell (e.g., a mammalian cell). In certain embodiments, the cells (e.g., a mammalian cell) are proliferated at least until forming a lymphoma (e.g., a B-cell lymphoma). In some embodiments, the proliferating cells are lymphoma cells. In certain embodiments, the cells (e.g., a mammalian cell) do not require and/or are not fused, e.g., with a myeloma, prior to proliferation (e.g., in order to provide a cell population sufficient to produce a significant or therapeutic amount of the antibody in a reasonable period of time).

In some embodiments, the method further comprises recovering from the cell (e.g., a mammalian cell) the antibody that specifically binds the selected antigen. In some embodiments, the antibody produced is soluble and is not membrane bound.

In some embodiments, the cell (e.g., a mammalian cell) (e.g., a mammalian cell) is present in an organism (e.g., a mammal). In some embodiments, the organism is a xenomouse. In certain embodiments, the organism (e.g., a mammal) further comprises a nucleic acid sequence (e.g., a transgenic sequence) that encodes a transgenic onco-peptide sequence (e.g., MYC). In some embodiments, the organism (e.g., a mammal) further comprises a transgenic nucleic acid sequence encoding a tTA peptide or an rtTA peptide. In some embodiments, the nucleic acid sequence (e.g., transgenic nucleic acid sequence) encoding the tTA peptide or the rtTA peptide comprises a B-cell-selective promoter operably linked to the open reading frame encoding the tTA peptide or the rtTA peptide. In some embodiments, the nucleic acid sequence (e.g., transgenic nucleic acid sequence) encoding the tTA peptide or the rtTA peptide comprises the MMTV promoter operably linked to the open reading frame encoding the tTA peptide or the rtTA peptide.

In certain embodiments, contacting a cell comprising a Myc peptide (e.g., a recombinant Myc peptide (e.g., a Myc fusion peptide as described herein)) comprises introducing (or otherwise providing to) the selected antigen into the organism (e.g., a mammal) by any suitable manner. In some embodiments, the onco-peptide is a fusion peptide. In some embodiments, the onco-peptide is a fusion peptide comprising a PTD. In some embodiments, the onco-peptide is TAT-MYC. In some embodiments, the onco-peptide is Myc-ER. In some embodiments, the onco-peptide is Myc-GR. In some embodiments, the organism is a xenomouse. In certain embodiments, the organism (e.g., a mammal) further comprises a nucleic acid sequence (e.g., transgenic nucleic acid sequence) encoding the selected antigen. In some embodiments, the nucleic acid sequence (e.g., transgenic nucleic acid sequence) encoding the selected antigen comprises a B-cell-selective promoter operably linked to the open reading frame encoding the selected antigen.

In some embodiments, a method described herein further comprises providing doxycycline, tetracycline, or an analog thereof to the organism (e.g., a mammal) to suppress tTA-dependent expression of the Myc peptide. In some embodiments, a method described herein further comprises providing doxycycline, tetracycline, or an analog thereof to the organism (e.g., a mammal) for a period of time sufficient to suppress tTA-dependent expression of the transgenic MYC gene, and withdrawing the doxycycline, tetracycline, or analog thereof after the period of time to induce tTA-dependent expression of the transgenic MYC.

In some embodiments, a method described herein further comprises recovering from the organism (e.g., a mammal; e.g., a xenomouse) a cell (e.g., B-cells) that express the antibody that specifically binds the selected antigen. In certain embodiments, a method described herein further comprises recovering from the cells (e.g., mammalian cells) (e.g., B-cells) the antibody that specifically binds the selected antigen. In some embodiments, a method described herein further comprises recovering from the organism (e.g., a mammal) the antibody that specifically binds the selected antigen.

In some embodiments, provided herein is a method of producing an antibody that specifically binds to an antigen, comprising: contacting a cell with a selected antigen and an onco-peptide (e.g. Myc).

In some embodiments, the onco-peptide is a peptide that promotes cell survival and/or proliferation. In certain embodiments, the cell is a mammalian cell. In some embodiments, the cell is a human cell. In some embodiments, the cell is a B-cell. In some embodiments, the cell is a hematopoietic cell. In some embodiments, the cell is a human B-cell. In some embodiments, the cell is a human hematopoietic cell. In some embodiments, the cell (e.g., a mammalian cell) expresses CD79 on its cell surface. In some embodiments, the cell (e.g., a mammalian cell) comprises an intact salvage pathway for purine biosynthesis and is tolerant and or anergic to the selected antigen. In some embodiments, the cell (e.g., a mammalian cell) is a B-cell, a B-cell precursor or progenitor, or a hematopoietic stem cell. In certain embodiments, the antibody specifically binds to the selected antigen. In certain embodiments, the onco-peptide is a peptide that promotes cell survival and/or proliferation.

In certain embodiments, the cell (e.g., a mammalian cell) is contacted with the selected antigen by any suitable method. In specific embodiments, the cell (e.g., a mammalian cell) comprises a nucleic acid sequence (e.g., a transgenic sequence) that encodes the selected antigen and is, thereby, contacted with the selected antigen. In some embodiments, the selected antigen is a self-antigen.

In certain embodiments, wherein a B-cell precursor or progenitor or a hematopoietic stem cell are used, a method described herein further comprises allowing or inducing differentiation of the cell (e.g., a mammalian cell) to a B-cell.

In some embodiments, the onco-peptide is a fusion peptide that comprises a receptor that activates the onco-peptide activity (e.g., cell survival and/or proliferation) when bound with a ligand. In some embodiments, the receptor is an estrogen receptor (ER). In some embodiments, the receptor is a glucocorticoid receptor (GR). In specific embodiments, the onco-peptide is a Myc-ER fusion peptide. In some embodiments, the onco-peptide is a Myc-GR fusion peptide. In certain embodiments, a method described herein further comprises contacting a cell comprising a recombinant onco-peptide that is a fusion peptide comprising a receptor with a ligand that binds the receptor. In specific embodiments, a method described herein further comprises contacting the cell (e.g., a mammalian cell) comprising a Myc-ER fusion peptide with an estrogen receptor modulator (e.g., an ER agonist or antagonist). In specific embodiments, a method described herein further comprises contacting the cell (e.g., a mammalian cell) comprising a Myc-GR fusion peptide with an glucocorticoid receptor modulator (e.g., a GR agonist or antagonist).

In some embodiments, the onco-peptide is a fusion peptide that comprises a (a) a transporter peptide sequence (e.g., TAT); and (b) a MYC sequence (e.g., c-MYC). In some embodiments, the fusion peptide is a peptide of Formula (I):

transporter peptide sequence-MYC sequence.

In some embodiments, a fusion peptide disclosed herein comprises (a) a transporter peptide sequence; (b) a MYC sequence; and (c) one or more molecules that link the transporter peptide sequence and the MYC sequence (i.e., "X"). In some embodiments, the fusion peptide is a peptide of Formula (II):

transporter peptide sequence-X-MYC sequence, wherein -X- is molecule that links the transporter peptide sequence and the MYC sequence. In some embodiments, -X- is an amino acid. In some embodiments, -X- is at least one amino acid.

In some embodiments, the method further comprises recovering from the cell (e.g., a mammalian cell) the antibody that specifically binds the selected antigen. In some embodiments, the antibody produced is soluble and is not membrane bound.

In certain embodiments, contacting a cell comprising a Myc peptide (e.g., a recombinant Myc peptide, a TAT-Myc fusion peptide) comprises introducing (or otherwise providing to) the selected antigen into the organism (e.g., a mammal) by any suitable manner. In some embodiments, the Myc peptide is a fusion peptide. In some embodiments, the Myc peptide is a TAT-Myc peptide as described herein. In some embodiments, the organism is a xenomouse. In certain embodiments, the organism (e.g., a mammal) further comprises a nucleic acid sequence (e.g., transgenic nucleic acid sequence) encoding the selected antigen. In some embodiments, the nucleic acid sequence (e.g., transgenic nucleic acid sequence) encoding the selected antigen comprises a B-cell-selective promoter operably linked to the open reading frame encoding the selected antigen.

In some embodiments, a method described herein further comprises recovering from the organism (e.g., a mammal) a cell (e.g., B-cells) that express the antibody that specifically binds the selected antigen. In certain embodiments, a method described herein further comprises recovering from the cells (e.g., mammalian cells), B-cells the antibody that specifically binds the selected antigen. In some embodiments, a method described herein further comprises recovering from the organism (e.g., a mammal) the antibody that specifically binds the selected antigen.

In some embodiments, provided herein is a method for producing an antibody that specifically binds to an antigen, comprising: contacting a cell with a selected antigen, wherein the cell (e.g., a mammalian cell) over-expresses an onco-peptide (e.g., recombinant onco-peptide; e.g., Myc). In some embodiments, the Myc peptide is a fusion peptide. In some embodiments, the Myc peptide is a TAT-Myc peptide as described herein.

In some embodiments, the onco-peptide is a peptide that promotes cell survival and/or proliferation. In certain embodiments, the cell is a mammalian cell. In some embodiments, the cell is a human cell. In some embodiments, the cell is a B-cell. In some embodiments, the cell is a hematopoietic cell. In some embodiments, the cell is a human B-cell. In some embodiments, the cell is a human hematopoietic cell. In some embodiments, the cell (e.g., a mammalian cell) expresses CD79 on its cell surface. In some embodiments, the cell (e.g., a mammalian cell) comprising a nucleic acid sequence (e.g., a transgenic sequence) comprises an intact salvage pathway for purine biosynthesis. In some embodiments, the cell (e.g., a mammalian cell) comprising a nucleic acid sequence (e.g., a transgenic sequence) comprises an intact salvage pathway for purine biosynthesis and is tolerant and or anergic to the selected antigen. In some embodiments, the cell (e.g., a mammalian cell) is a B-cell, a B-cell progenitor or precursor, or a hematopoietic stem cell. In certain embodiments, the antibody specifically binds to the selected antigen. In certain embodiments, the onco-peptide is a peptide that promotes cell survival and/or proliferation.

In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In certain instances, the down-regulation of an Max-1 gene and/or polypeptide upregulates the expression of a MYC proto-oncogene and/or a polypeptide encoded by a MYC proto-oncogene. In some embodiments, the small molecule is an antagonist of Mxi-1. In certain instances, the down-regulation of an Mxi-1 gene and/or polypeptide upregulates the expression of a MYC proto-oncogene and/or a polypeptide encoded by a MYC proto-oncogene. In some embodiments, the small molecule is an antagonist of MAD. In certain instances, the down-regulation of a MAD-1 gene and/or polypeptide upregulates the expression of a MYC proto-oncogene and/or a polypeptide encoded by a MYC proto-oncogene. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof.

In certain embodiments, the cell (e.g., a mammalian cell) is contacted with the selected antigen by any suitable method. In specific embodiments, the cell (e.g., a mammalian cell) comprises a nucleic acid sequence (e.g., a transgenic sequence) that encodes a nucleic acid sequence (e.g., a transgenic sequence) that encodes the selected antigen. In some embodiments, the selected antigen is a self-antigen.

In certain embodiments, wherein a B-cell precursor or progenitor or a hematopoietic stem cell are used, a method described herein further comprises allowing or inducing differentiation of the cell (e.g., a mammalian cell) to a B-cell.

In some embodiments, a MYC sequence (e.g., a transgenic sequence) further comprises a B-cell selective promoter or an inducible promoter. In some embodiments, a nucleic acid sequence (e.g., a transgenic sequence) encoding the selected antigen further comprises a B-cell selective promoter or an inducible promoter. In some embodiments, a B-cell selective promoter is, by way of non-limiting example, the Eµ promoter. In some embodiments, the inducible promoter comprises, by way of non-limiting example, one or more TREs. In certain embodiments, the cell (e.g., a mammalian cell) further comprises a nucleic acid sequence (e.g., a transgenic sequence) that encodes a tTA peptide or an rtTA peptide. In some embodiments, the nucleic acid sequence (e.g., transgenic nucleic acid sequence) encoding the tTA peptide or the rtTA peptide comprises a B-cell-selective promoter operably linked to the open reading frame encoding the tTA peptide or the rtTA peptide. In some embodiments, the nucleic acid sequence (e.g., transgenic nucleic acid sequence) encoding the tTA peptide or the rtTA peptide comprises the MMTV promoter operably linked to the open reading frame encoding the tTA peptide or the rtTA peptide. Furthermore, in some embodiments, wherein an inducible promoter comprises one or more TREs, a method described herein further comprises contacting the cell (e.g., a mammalian cell) with doxycycline, tetracycline, or an analog thereof.

In some embodiments, the onco-peptide is a fusion peptide that comprises a receptor that activates the onco-peptide activity (e.g., cell survival and/or proliferation) when bound with a ligand. In some embodiments, the receptor is an estrogen receptor (ER). In specific embodiments, the onco-peptide is a Myc-ER fusion peptide. In some embodiments, the receptor is an clucocorticoid receptor (GR). In specific embodiments, the onco-peptide is a Myc-GR fusion peptide. In certain embodiments, a method described herein further comprises contacting a cell comprising a fusion peptide comprising a receptor with a ligand that specifically binds to the receptor. In specific embodiments, a method described herein further comprises contacting a cell comprising a Myc-ER peptide with an estrogen receptor modulator (e.g., an ER agonist or antagonist). In specific embodiments, a method described herein further comprises contacting a cell comprising a Myc-GR peptide with an glucocorticoid receptor modulator (e.g., a GR agonist or antagonist).

In some embodiments, the onco-peptide is a fusion peptide that comprises a (a) a transporter peptide sequence (e.g., TAT); and (b) a MYC sequence (e.g., c-MYC). In some embodiments, the fusion peptide is a peptide of Formula (I):

transporter peptide sequence-MYC sequence.

In some embodiments, a fusion peptide disclosed herein comprises (a) a transporter peptide sequence; (b) a MYC sequence; and (c) one or more molecules that link the transporter peptide sequence and the MYC sequence (i.e., "X"). In some embodiments, the fusion peptide is a peptide of Formula (II):

transporter peptide sequence-X-MYC sequence, wherein -X- is molecule that links the transporter peptide sequence and the MYC sequence. In some embodiments, -X- is an amino acid. In some embodiments, -X- is at least one amino acid.

In certain embodiments, a method described herein further comprises inducing MYC expression, Myc activity, or a combination thereof, in the cell (e.g., a mammalian cell). In some embodiments, a method described herein further comprises proliferating or inducing proliferation of the cell (e.g., a mammalian cell). In certain embodiments, the cells (e.g., mammalian cells) are proliferated at least until forming a lymphoma (e.g., a B-cell lymphoma). In some embodiments, the proliferating cells are lymphoma cells. In certain embodiments, the cells (e.g., mammalian cells) do not require and/or are not fused, e.g., with a myeloma, prior to proliferation (e.g., in order to provide a cell population sufficient to produce a significant or therapeutic amount of the antibody in a reasonable period of time).

In some embodiments, the method further comprises recovering the antibody that specifically binds the selected antigen. In some embodiments, the antibody produced is soluble and is not membrane bound. In some embodiments, the antibody produced is membrane bound. In some embodiments, the antibody produced is intracellular.

In some embodiments, the cell (e.g., a mammalian cell) is present in an organism (e.g., a mammal). In some embodiments, the organism is a xenomouse. In certain embodiments, the organism (e.g., a mammal) comprises a nucleic acid sequence (e.g., a transgenic sequence) that encodes an onco-peptide. In some embodiments, the organism (e.g., a mammal) further comprises a nucleic acid sequence (e.g., a transgenic sequence) that encodes a tTA peptide or an rtTA peptide. In some embodiments, the nucleic acid sequence (e.g., transgenic nucleic acid sequence) encoding the tTA peptide or the rtTA peptide comprises a B-cell-selective promoter operably linked to the open reading frame encoding the tTA peptide or the rtTA peptide. In some embodiments, the nucleic acid sequence (e.g., transgenic nucleic acid sequence) encoding the tTA peptide or the rtTA peptide comprises the MMTV promoter operably linked to the open reading frame encoding the tTA peptide or the rtTA peptide.

In certain embodiments, contacting the cell (e.g., a mammalian cell) comprising MYC (e.g., a transgenic MYC) comprises introducing (or otherwise providing to) the selected antigen into the organism (e.g., a mammal) by any suitable manner. In certain embodiments, the organism (e.g., a mammal) further comprises a nucleic acid sequence (e.g., a transgenic sequence) encoding the selected antigen. In some embodiments, the nucleic acid sequence (e.g., transgenic nucleic acid sequence) encoding the selected antigen comprises a B-cell-selective promoter operably linked to the open reading frame encoding the selected antigen.

In some embodiments, a method described herein further comprises providing doxycycline, tetracycline, or an analog thereof to the organism (e.g., a mammal) to suppress tTA-dependent expression of the nucleic acid sequence (e.g., transgenic nucleic acid sequence) encoding a Myc peptide (e.g., a recombinant Myc peptide (e.g., a Myc fusion peptide as described herein)). In some embodiments, the onco-peptide is a fusion peptide. In some embodiments, the onco-peptide is a fusion peptide comprising a PTD. In some embodiments, the onco-peptide is TAT-MYC. In some embodiments, the onco-peptide is Myc-ER. In some embodiments, the onco-peptide is Myc-GR. In some embodiments, a method described herein further comprises (a) providing doxycycline, tetracycline, or an analog thereof to the organism (e.g., a mammal) for a period of time sufficient to suppress tTA-dependent expression of the nucleic acid sequence (e.g., transgenic nucleic acid sequence) encoding the Myc peptide, and (b) withdrawing the doxycycline, tetracycline, or analog thereof after the period of time to induce tTA-dependent expression of the nucleic acid sequence (e.g., transgenic nucleic acid sequence) encoding the Myc peptide.

In some embodiments, a method described herein further comprises recovering from the organism (e.g., a mammal) a cell (e.g., B-cell) that express the antibody that specifically binds the selected antigen. In certain embodiments, a method described herein further comprises recovering from the cell (e.g., a mammalian cell) (e.g., B-cell) the antibody that specifically binds the selected antigen. In some embodiments, a method described herein further comprises recovering from the organism (e.g., a mammal) the antibody that specifically binds the selected antigen.

In specific embodiments, provided herein is a method of producing an antibody that specifically binds to an antigen, comprising: introducing (or otherwise providing to) a selected antigen into an organism (e.g., a mammal), wherein the organism (e.g., a mammal) comprises a nucleic acid sequence (e.g., a transgenic sequence) that encodes an onco-peptide (e.g., recombinant onco-peptide; e.g., Myc), and comprises an inducible promoter or a B-cell-selective promoter operably linked to the open reading frame of the encoded onco-peptide.

In some embodiments, the onco-peptide is a fusion peptide. In some embodiments, the onco-peptide is a fusion peptide comprising a PTD. In some embodiments, the onco-peptide is TAT-MYC. In some embodiments, the onco-peptide is Myc-ER. In some embodiments, the onco-peptide is Myc-GR.

In some embodiments, the organism is a xenomouse.

In some embodiments, provided herein is a method of producing an antibody that specifically binds to an antigen, comprising:

a. providing a cell (e.g., a B-cell) expressing an antibody that specifically binds an antigen, wherein the cell (e.g., a mammalian cell) comprises an onco-peptide (e.g., a recombinant onco-peptide; e.g., Myc) or a nucleic acid sequence (e.g., a transgenic sequence) encoding an onco-peptide (e.g., a recombinant onco-peptide; e.g., Myc); and b. inducing activity of the onco-peptide in the cell (e.g., a mammalian cell).

In some embodiments, the onco-peptide is a fusion peptide. In some embodiments, the onco-peptide is a fusion peptide comprising a PTD. In some embodiments, the onco-peptide is TAT-MYC. In some embodiments, the onco-peptide is Myc-ER. In some embodiments, the onco-peptide is Myc-GR.

In some embodiments, the cell (e.g., a mammalian cell) is prepared by contacting a cell with the selected antigen. In some embodiments, the selected antigen is a self-antigen. In certain embodiments, the antibody specifically binds to the selected antigen.

In some embodiments, the cell is a human cell. In certain embodiments, the cell (e.g., a mammalian cell) is a B-cell, a B-cell precursor or progenitor, or a hematopoietic stem cell. In some embodiments, the B-cell is an anergic B-cell. In some embodiments, the cell (e.g., a mammalian cell) expresses CD79 on its cell surface. In some embodiments, the B-cell is a mouse B-cell. In some embodiments, the cell (e.g., a mammalian cell; e.g., B-cell) is from an organism (e.g., a mammal; e.g., a xenomouse) that was administered (i.e., inoculated with, or immunized against) the selected antigen. In some embodiments, the organism is a xenomouse. In some embodiments, the organism (e.g., a mammal) comprises an onco-peptide (e.g., a recombinant onco-peptide; e.g., Myc) or a nucleic acid sequence (e.g., a transgenic sequence) encoding an onco-peptide (e.g., a recombinant onco-peptide; e.g., Myc). In some embodiments, the onco-peptide is a fusion peptide. In some embodiments, the onco-peptide is a fusion peptide comprising a PTD. In some embodiments, the onco-peptide is TAT-MYC. In some embodiments, the onco-peptide is Myc-ER. In some embodiments, the onco-peptide is Myc-GR. In some embodiments, the organism (e.g., a mammal) further comprises a nucleic acid sequence (e.g., a transgenic sequence) that encodes the selected antigen. In some embodiments, a MYC sequence (e.g., a transgenic sequence) further comprises a B-cell selective promoter or an inducible promoter. In some embodiments, a nucleic acid sequence (e.g., a transgenic sequence) encoding the selected antigen further comprises a B-cell selective promoter or an inducible promoter. In some embodiments, a B-cell selective promoter is, by way of non-limiting example, the Eμ promoter. In some embodiments, the inducible promoter comprises, by way of non-limiting example, one or more TREs.

In certain embodiments, wherein a B-cell precursor or progenitor or a hematopoietic stem cell are used, a method described herein further comprises allowing or inducing differentiation of the cell (e.g., a mammalian cell) into a B-cell.

In some embodiments, the method further comprises recovering the antibody. In certain embodiments, activity of the onco-peptide induces expansion of the cell (e.g., a mammalian cell) population.

In some embodiments, the cell (e.g., a mammalian cell) (e.g., B-cell) is present in an organism (e.g., a mammal) and inducing the activity of the onco-peptide (e.g., recombinant onco-peptide; e.g., Myc) in the cell (e.g., a mammalian cell) (e.g., B-cell) occurs in vivo. In some embodiments, the organism is a xenomouse. In some embodiments, the method further comprises introducing (or otherwise providing to) an onco-peptide (e.g., a recombinant onco-peptide; e.g., Myc) or the nucleic acid sequence (e.g., transgenic nucleic acid sequence) encoding an onco-peptide (e.g., a recombinant onco-peptide; e.g., Myc) into the cell (e.g., a mammalian cell). In some embodiments, the onco-peptide or the nucleic acid sequence (e.g., transgenic nucleic acid sequence) encoding the onco-peptide is introduced into the cell (e.g., a mammalian cell) ex vivo and then the cell (e.g., a mammalian cell) is introduced into an organism (e.g., a mammal). In some embodiments, the organism is a xenomouse. In specific embodiments, the process comprises introducing (or otherwise providing to) a onco-peptide (e.g., recombinant onco-peptide; e.g., Myc) into a cell (e.g., B-cell) ex vivo. In some embodiments, the onco-peptide (e.g., recombinant onco-peptide; e.g., Myc) comprises a protein transduction domain, e.g., HIV-1 Tat or Vpr (e.g., Tat-Myc or Vpr-Myc).

In some embodiments, inducing the activity of an onco-peptide includes inducing the expression of a nucleic acid sequence encoding the onco-peptide, inducing the activity of the onco-peptide, or a combination thereof. In certain instances, inducing activity of the onco-peptide includes inducing over-expression of the onco-peptide. In some embodiments, inducible expression or over-expression of the onco-peptide is achieved by activating an inducible promoter of a nucleic acid sequence (e.g., a transgenic sequence) that induces expression of an onco-peptide. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof.

In certain embodiments, the nucleic acid sequence (e.g., transgenic nucleic acid sequence) encoding an onco-peptide (e.g., recombinant onco-peptide; e.g., Myc) comprises a promoter, e.g., a B-cell selective promoter or an inducible promoter, operably linked to the open reading frame encoding the onco-peptide (e.g., recombinant onco-peptide; e.g., Myc). In some specific embodiments, the nucleic acid sequence (e.g., transgenic nucleic acid sequence) encoding an onco-peptide (e.g., recombinant onco-peptide; e.g., Myc) comprises a B-cell-selective promoter operably linked to an open reading frame. In certain specific embodiments, the nucleic acid sequence (e.g., transgenic nucleic acid sequence) encoding the onco-peptide comprises an inducible promoter operably linked to an open reading frame for the Myc peptide. In some embodiments, the inducible promoter comprises one or more TREs and the cell (e.g., a mammalian cell) further expresses a tTA peptide or an rtTA peptide. In some embodiments, the cell (e.g., a mammalian cell) expresses the tTA peptide. In some embodiments, the onco-peptide is a fusion peptide. In some embodiments, the onco-peptide is a fusion peptide comprising a PTD. In some embodiments, the onco-peptide is TAT-MYC. In some embodiments, the onco-peptide is Myc-ER. In some embodiments, the onco-peptide is Myc-GR.

In some embodiments, the onco-peptide is a fusion peptide that is inducibly activated. In specific embodiments, the onco-peptide is a fusion peptide comprising a receptor that activates the survival and/or proliferative characteristic of the onco-peptide when modulated (i.e., bound with a ligand, such, as an agonist or antagonist). In specific embodiments, the onco-peptide (e.g., a recombinant onco-peptide; e.g., Myc) is a fusion peptide comprising an estrogen receptor (e.g., Myc-ER). In some embodiments, inducing activity of the onco-peptide in the cell (e.g., a mammalian cell) comprises contacting the cell (e.g., a mammalian cell) with an ER ligand. In specific embodiments, the onco-peptide (e.g., a recombinant onco-peptide; e.g., Myc) is a fusion peptide comprising an glucocorticoid receptor (e.g., Myc-GR). In some embodiments, inducing activity of the onco-peptide in the cell (e.g., a mammalian cell) comprises contacting the cell (e.g., a mammalian cell) with a GR ligand.

In some embodiments, the onco-peptide is a fusion peptide that comprises a (a) a transporter peptide sequence (e.g., TAT); and (b) a MYC sequence (e.g., c-MYC). In some embodiments, the fusion peptide is a peptide of Formula (I):

transporter peptide sequence-MYC sequence.

In some embodiments, a fusion peptide disclosed herein comprises (a) a transporter peptide sequence; (b) a MYC sequence; and (c) one or more molecules that link the transporter peptide sequence and the MYC sequence (i.e., "X"). In some embodiments, the fusion peptide is a peptide of Formula (II):

transporter peptide sequence-X-MYC sequence, wherein -X- is molecule that links the transporter peptide sequence and the MYC sequence. In some embodiments, -X- is an amino acid. In some embodiments, -X- is at least one amino acid.

In some embodiments, the cell (e.g., a mammalian cell; e.g., a B-cell) comprising an onco-peptide (e.g., recombinant onco-peptide; e.g., Myc) or a nucleic acid sequence (e.g., a transgenic sequence) encoding an onco-peptide (e.g., a recombinant onco-peptide; e.g., Myc) is present in an organism (e.g., a mammal). In some embodiments, the Myc peptide is a fusion peptide. In some embodiments, the Myc peptide is a TAT-Myc peptide as described herein. In some embodiments, the organism is a xenomouse. In some embodiments, the organism is administered (i.e., immunized against, inoculated with) an antigen and allowed to mount an immune response to the selected antigen. In some embodiments, the organism is exposed to the selected antigen by any suitable manner. In some embodiments, the selected antigen is administered with an adjuvant. In some embodiments, the selected antigen is covalently linked to a carrier. Examples of carries include but are not limited to bovine serum albumin, keyhole limpet hemocyanin, ovalbumin and hyroglobulin.

In some embodiments, a cell or organism utilized in a method disclosed herein includes those that inducibly over-express an onco-peptide (e.g., recombinant onco-peptide; e.g., Myc) and are engineered to express an antigen. Such cells and organisms are prepared by any suitable method including, by way of non-limiting example, retroviral mediated transduction of bone marrow hematopoietic stem cells, production of transgenic organisms (or crossing the onco-peptide over-expressing organisms with an organism that expresses the selected antigen), or any other method for gene delivery into the cell (e.g., a mammalian cell) or organism. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof. In some embodiments, the cell (e.g., a mammalian cell) or organism is maintained under conditions in which an onco-peptide (e.g., recombinant onco-peptide; e.g., Myc) is not over-expressed until the production of antibodies is desired. In some embodiments, the cell (e.g., a mammalian cell) or organism is maintained under conditions in which the onco-peptide activity is not induced until the production of antibodies is desired. In some embodiments, the cell (e.g., a mammalian cell) or organism is maintained under conditions under which the onco-peptide is over-expressed in a cell (e.g., a mammalian cell; e.g., a B-cell) that produces antibodies that specifically binds to the selected antigen.

In some embodiments, B cells specific for a heterologous antigen, a self antigen, or an auto antigen are tolerant to the heterologous antigen, self antigen, or auto antigen. In some embodiments, induction of onco-peptide (e.g., recombinant onco-peptide; e.g., Myc) activity in tolerant B cells induces a break in tolerance to an antigen and induces production of antibodies that specifically binds to the selected antigen. In some embodiments, a tolerant B-cell is anergic to an antigen. In some embodiments, a tolerant B-cell is tolerant to an antigen that is immunologically similar to an auto antigen or self antigen. In some embodiments, a tolerant B-cell is tolerant to an antigen that is a heterologous antigen. In some embodiments, the heterologous antigen is homologous to an auto antigen or self antigen. In some embodiments, the selected antigen specific B-cells produced by over-expression of MYC are removed from the organism and are cloned to produce immortal antibody producing B-cells without the need for cell fusion to a myeloma partner. In some embodiments, the Myc peptide is a fusion peptide. In some embodiments, the Myc peptide is a TAT-Myc peptide as described herein.

In specific embodiments, provided herein is a method for producing an antibody that specifically binds to an antigen, comprising:
  a. providing a B-cell that is tolerant to an antigen; and
  b. inducing onco-peptide (e.g., recombinant onco-peptide; e.g., Myc) activity in a B-cell that is tolerant to the selected antigen.

In some embodiments, the onco-peptide is a fusion peptide. In some embodiments, the onco-peptide is a fusion peptide comprising a PTD. In some embodiments, the onco-peptide is TAT-MYC. In some embodiments, the onco-peptide is Myc-ER. In some embodiments, the onco-peptide is Myc-GR. In certain embodiments, induction of onco-peptide activity induces an expansion of the B-cell population. In some embodiments, the method further comprises recovering the antibody from a plurality of recombinant B-cells generated by the expansion of the B-cell.

In specific embodiments, provided herein is a method of producing an antibody that specifically binds to an antigen, comprising: administering to an immuno-deficient organism (e.g., a mammal) a plurality of hematopoietic stem cells (e.g., recombinant hematopoietic stem cells) that comprise a nucleic acid sequence (e.g., a transgenic sequence) encoding an onco-peptide (e.g., a recombinant onco-peptide; e.g., Myc); and contacting a selected antigen with the immuno-deficient organism (e.g., a mammal). In some embodiments, the onco-peptide is a fusion peptide. In some embodiments, the onco-peptide is a fusion peptide comprising a PTD. In some embodiments, the onco-peptide is TAT-MYC. In some embodiments, the onco-peptide is Myc-ER. In some embodiments, the onco-peptide is Myc-GR.

In some embodiments, the organism is a xenomouse.

In certain embodiments, the onco-peptide is a Myc peptide. In some embodiments, the onco-peptide is a fusion peptide. In some embodiments, the onco-peptide is a fusion peptide comprising a PTD. In some embodiments, the onco-peptide is TAT-MYC. In some embodiments, the onco-peptide is inducibly activated (e.g., inducibly expressed or the function is inducibly activated). In certain embodiments, the onco-peptide is a fusion peptide comprising a receptor, and the function of the onco-peptide is inducibly activated by modulating or binding the receptor (e.g., with a ligand, such as an agonist or antagonist). In specific embodiments, the onco-peptide is Myc-ER. In specific embodiments, the onco-peptide is Myc-GR. In further embodiments, the method further comprises inducing onco-peptide (e.g., recombinant onco-peptide; e.g., Myc) activity in the organism (e.g., a mammal). In some embodiments, the organism is a xenomouse. For example, in the case of Myc-ER, Myc activity is optionally induced by administering an estrogen receptor ligand to the immuno-deficient organism (e.g., a mammal); in the case of a MYC nucleic acid sequence with an inducible promoter comprising one or more TREs, Myc activity is induced by providing doxycycline, tetracycline, or an analog thereof to the immuno-deficient organism (e.g., a mammal); or in the case of Myc-GR, Myc activity is induced by administering a glucocorticoid receptor ligand to the immune-deficient organism.

In some embodiments, the hematopoietic stem cells further comprise a nucleic acid sequence (e.g., a transgenic sequence) encoding a polypeptide that inhibits apoptosis (e.g., Bcl-2, Bcl-x, Mcl-1).

In some embodiments, a method described herein further comprises inducing a plurality of the hematopoietic stem cells to differentiate into B-cells. In some embodiments, a method disclosed herein further comprises recovering a plurality of the B-cells that express an antibody that specifically binds to the selected antigen from the immuno-deficient organism (e.g., a mammal). In some embodiments, a method described herein further comprises recovering the antibody from the immuno-deficient organism (e.g., a mammal) or from a plurality of B-cells that express the antibody.

In some embodiments, the nucleic acid sequence (e.g., transgenic nucleic acid sequence) encoding an onco-peptide comprises an inducible promoter or a B-cell-selective promoter. In some embodiments, the nucleic acid sequence (e.g., transgenic nucleic acid sequence) encoding an onco-peptide comprises an inducible promoter comprising one or more TREs. In some embodiments, the hematopoietic stem cells express tTA or rtTA. In some embodiments, a method described herein further comprises providing doxycycline, tetracycline, or an analog thereof to the immuno-deficient organism (e.g., a mammal) to suppress the tTA-dependent transactivation, and withdrawing the doxycycline, tetracycline, or analog thereof to induce tTA-dependent transactivation. In some embodiments, the B-cell selective promoter is the Eµ promoter.

In some embodiments, an immuno-deficient organism (e.g., a mammal) is obtained by irradiating the organism (e.g., a mammal). In some embodiments, the immuno-deficient organism (e.g., a mammal) is a Rag-1ko, Rag-2, SCID, DNA-PK, Ku70, Ku80, XRCC4, or µMT mouse. In some embodiments, the organism is a xenomouse.

In certain embodiments, the selected antigen is administered to the organism by any suitable method. In some embodiments, the selected antigen is a self antigen. In some embodiments, the organism is an immuno-deficient mammal. In some embodiments, the organism is an immuno-deficient mouse. In some embodiments, the organism is an immune-deficient xenomouse. In some embodiments, the immuno-deficient organism (e.g., a mammal) expresses the selected antigen. In some embodiments, the immuno-deficient organism (e.g., a mammal) that expresses the selected antigen comprises an exogenous nucleic acid sequence that encodes the selected antigen. In some embodiments, the selected antigen is introduced by transfection with a nucleic acid expression vector or infection with a recombinant virus expression vector. In some embodiments, the recombinant virus expression vector is a recombinant lentivirus. In certain embodiments, the antibody specifically binds to the selected antigen. In some embodiments, the Myc peptide is a fusion peptide. In some embodiments, the Myc peptide is a TAT-Myc peptide as described herein.

In some embodiments, hematopoietic stem cells that over-express MYC are used to reconstitute the peripheral lymphoid compartments of immuno-deficient organisms. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof. In some embodiments, the immuno-deficient organisms are rendered immuno-deficient by lethal irradiation. In some embodiments, immuno-deficient organisms are lethally irradiated mice. In some embodiments, the immuno-deficient organism is any immuno-deficient or immuno-compromised mouse. In some embodiments, the immuno-deficient animal is a Rag-1 knock out, Rag-2, SCID, DNA-PK, Ku70, Ku80, XRCC4, or µMT mouse. The peripheral lymphoid compartment of an immuno-deficient animal is typically reconstituted in 8-12 weeks after transplantation of hematopoietic stem cells. In some embodiments, organisms that are reconstituted with hematopoietic stem cells that over-express MYC, are further genetically altered to express the selected antigen. In some embodiments, organisms that are reconstituted with hematopoietic stem cells that over-express MYC are administered (i.e., immunized with or inoculated against) the selected antigen.

In some embodiment B-cell populations (e.g., anergic B-cells, such as AN1/T3) are isolated from organisms reconstituted with hematopoietic stem cells and are used in any method described herein. In some embodiments, hematopoietic stem cells that over-express MYC reconstitute the peripheral hematopoietic compartment of immuno-deficient organisms, are exposed to the selected antigen and develop into antigen specific AN1/T3 cell populations. In some embodiments, induction of Myc activity in these cells generates immortal antigen specific B-cells.

The hematopoietic stem cells utilized herein are prepared by any suitable method. In some embodiments, hematopoietic stem cells are isolated from an organism that over-expresses Myc. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, the organism is a xenomouse. In some embodiments, hematopoietic stem cells are isolated from organisms that comprise antigen specific B-cell populations. In some embodiments, hematopoietic stem cells are isolated from organisms that comprise antigen binding B-cell populations. In some embodiments, hematopoietic stem cells are isolated from organisms that comprise antigen specific AN1/T3 cell populations. In some embodiments, hematopoietic stem cells are isolated from organisms that comprise antigen specific anergic B-cell populations. In some embodiments, hematopoietic stem cells are isolated from wild type organisms. In some embodiments, the organisms are mice (e.g., transgenic mice or genetically altered mice). In some embodiments, organisms are treated with 5FU, in order to enrich for long-term hematopoietic stem cells, and induce their proliferation in vivo. In some embodiments, the organisms (e.g., mice) are treated with from 0.01 to 100 mg/mouse of 5FU. In some embodiments, the organisms (e.g., mice) are treated with from 0.1 to 50 mg/mouse of 5FU. In some embodiments, the organisms (e.g., mice) are treated with from 1 to 10 mg/mouse of 5FU. In some embodiments, the organisms (e.g., mice) are treated with 5 mg/mouse of 5FU. In some embodiments, bone marrow cells containing 5FU enriched populations of hematopoietic stem cells are isolated, by any suitable method, from the femurs and tibia bones of organisms that over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, hematopoietic stem cells are isolated approximately 1-10 days after administration of 5FU. In some embodiments, hematopoietic stem cells are isolated approximately 5 days after administration of 5FU. In some embodiments, hematopoietic stem cells are cultured in vitro in a media comprising human IL-3, IL-6 and Stem Cell Factor (SCF). In certain embodiments, isolated hematopoietic stem cells over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, hematopoietic stem cells are genetically altered to over-express MYC in vitro by introducing (or otherwise providing to) a nucleic acid into the hematopoietic stem cells in which the nucleic acid directs the over-expression of MYC. In some embodiments, the over-expression of MYC is inducible. In some embodiments, the hematopoietic stem cells are genetically altered to over-express MYC by infecting the hematopoietic stem cells in vitro with a virus that directs the over-expression of MYC. In some embodiments, the virus is a lentivirus, retrovirus or adenovirus. In some embodiments, the hematopoietic stem cells are genetically altered to over-express MYC by transfection with a nucleic acid. In some embodiments, the hematopoietic stem cells are also genetically altered to express a reporter gene. In certain embodiments, reporter genes are utilized and allow selection or isolation of cells that are genetically altered to express Myc. In some embodiments, the reporter gene is GFP (green fluorescent protein). In some embodiments, hematopoietic stem cells are transduced with a virus that directs the over-expression of MYC and also GFP. In some embodiments, the hematopoietic stem cells are infected with a lentivirus that directs the over-expression of MYC and GFP. In some embodiments, provided herein are hematopoietic stem cells that over-express MYC, as described herein, and are used to generate immortal antibody producing B-cells.

In various embodiments, of any of the methods disclosed herein, polyclonal populations of antibodies that specifically binds to the selected antigen, as well as the cell (e.g., a mammalian cell) producing such antibodies, are isolated directly from the tissues (spleen, lymph nodes, blood, etc.) or serum of organisms. In some embodiments, monoclonal populations of antibody producing cells are isolated from organisms, and monoclonal antibodies are recovered from culture media.

In some embodiments, provided herein is any isolated B-cell prepared by a method described herein. In some embodiments, provided herein is a cell (e.g., a mammalian cell) that has been engineered to produce a recombinant form of any antibody prepared according any process disclosed herein. In certain embodiments, provided herein is a B-cell that expresses a human or humanized antibody, and an onco-peptide (e.g., recombinant onco-peptide; e.g., Myc), a nucleic acid sequence (e.g., a transgenic sequence) that encodes an onco-peptide (e.g., recombinant onco-peptide; e.g., Myc), and/or wherein the B-cell over-expresses Myc. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof. In certain embodiments, the onco-peptide is a fusion peptide comprising a transduction domain (e.g., Tat-Myc or Vpr-Myc), a receptor that activates function of the onco-peptide when modulated or bound (e.g., Myc-ER, Myc-GR), or a combination thereof (e.g., Tat-Myc-ER, Tat-Myc-GR, Vpr-Myc-ER, or Vpr-Myc-GR). In some embodiments, provided herein is an isolated antibody prepared according to the process of any of the methods disclosed herein.

Human Antibodies

In certain embodiments, a method disclosed herein is utilized to prepare human or humanized antibodies. In some embodiments, the cells (e.g., mammalian cells) or organisms of any of a method disclosed herein express human antibodies. In some embodiments, the organism is a xenomouse.

In some embodiments, provided herein is a method of producing a human or humanized antibody comprising: providing a cell (e.g., a mammalian cell) that expresses human antibodies and comprises a nucleic acid sequence (e.g., a transgenic sequence) that encodes a Myc peptide, or a Myc peptide; and contacting the cell (e.g., a mammalian cell) with a selected antigen. In some embodiments, the onco-peptide is a fusion peptide. In some embodiments, the onco-peptide is a fusion peptide comprising a PTD. In some embodiments, the onco-peptide is TAT-MYC. In some embodiments, the onco-peptide is Myc-ER. In some embodiments, the onco-peptide is Myc-GR.

In some embodiments, the cell (e.g., a mammalian cell) that expresses human antibodies and comprises a nucleic acid sequence (e.g., a transgenic sequence) that encodes the Myc peptide, or the Myc is a cell that expresses cell-surface CD79. In some embodiments, the cell (e.g., a mammalian cell) expresses CD79 and comprises an intact salvage pathway for purine biosynthesis. In some embodiments, the cell (e.g., a mammalian cell) expresses CD79, comprises an intact salvage pathway for purine biosynthesis and is tolerant and or anergic to the selected antigen. In some embodiments, the cell (e.g., a mammalian cell) that expresses human antibodies and comprises the nucleic acid sequence (e.g., a transgenic sequence) that encodes a Myc peptide or a Myc peptide is a B-cell, a B-cell progenitor or precursor, or a hematopoietic stem cell. In some embodiments, the B-cell over-expresses Myc. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof. In some embodiments, the cell (e.g., a mammalian cell) that expresses human antibodies and comprises the nucleic acid sequence that encodes a Myc peptide or the Myc peptide is present in an organism (e.g., a mammal), and wherein the method further comprises recovering the antibody producing cell from the organism (e.g., a mammal). In some embodiments, the Myc peptide is a fusion peptide. In some embodiments, the Myc peptide is a TAT-Myc peptide as described herein. In some embodiments, the organism is a xenomouse. In some embodiments, the organism (e.g., a mammal) is a mouse. In some embodiments, the organism (e.g., a mammal) is an MMTV-tTA/TRE-MYC mouse. In some embodiments, the organism (e.g., a mammal) is obtained by: (a) presenting an immuno-deficient organism (e.g., a mammal); and (b) administering to the organism (e.g., a mammal) a plurality of hematopoietic stem cells that over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof. In some embodiments, the hematopoietic stem cells are human stem cells, including by way of example primary human cord blood. In further embodiments, the human stem cells are transduced to produce conditionally-activated MYC, including by way of example only MYC-ER and Myc-GR. In further or alternative embodiments, the aforementioned human stem cells are also transduced with the cDNA of an antigen: in such embodiments, the human stem cells will produce both the selected antigen and the conditionally-activated MYC. In further or alternative embodiments, the resulting human stem cells are administered to an immuno-deficient organism (e.g., a mammal)—as one option, upon detection of B-cells in the periphery, the immuno-deficient organism (e.g., a mammal) is provided with the agent that induces conditional expression of MYC. Alternatively, the human stem cells that have been transduced to produce conditionally-activated Myc are provided directly to the immuno-deficient organism (e.g., a mammal); upon detection of the B-cells in the periphery, the resulting organism (e.g., a mammal) is provided with lymphoma cells (including lymphoma cells from the same species or genera as the immuno-deficient organism (e.g., a mammal)) that express the selected antigen(s) of interest; the resulting organism (e.g., a mammal) is then provided with the agent that conditionally-activates MYC.

In any of the embodiments, described herein, the immuno-deficient organism (e.g., a mammal) is obtained by irradiating the organism (e.g., a mammal). In some embodiments, the immuno-deficient organism (e.g., a mammal) is a Rag-1ko, Rag-2, SCID, DNA-PK, Ku70, Ku80, XRCC4, or µMT mouse. In some embodiments, the organism (e.g., a mammal) expresses the selected antigen. In some embodiments, a method described herein further comprises recovering the antibody produced by the antibody producing cell. In some embodiments, a method described herein further comprises subjecting the antibody producing cell to conditions that induce over-expression of MYC. In some embodiments, the nucleic acid sequence (e.g., a transgenic sequence) that encodes the Myc peptide comprises an inducible promoter or a B-cell-selective promoter. In some embodiments, prior to isolating the antibody producing cell from the organism (e.g., a mammal) the antibody producing cell is subjected to conditions that induce over-expression of MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof.

In some embodiments, subsequent to isolating the antibody producing cell from the organism (e.g., a mammal) the antibody producing cell is subjected to conditions that induce over-expression of MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof. In some embodiments, the organism (e.g., a mammal) is an MMTV-rtTA/TRE-MYC; MMTV-rtTA/TRE-MYC/Rag-1−/−; MMTV-tTA/TRE-MYC; or MMTV-tTA/TRE-MYC/Rag-1−/− mouse and the conditions that induce over-expression of MYC are exposure to doxycycline, tetracycline, or an analog thereof. In some embodiments, the Myc peptide is a Myc-ER fusion peptide. In some embodiments, a method described herein further comprises contacting the cell (e.g., a mammalian cell) with an estrogen receptor ligand. In some embodiments, the cell (e.g., a mammalian cell) is contacted with the selected antigen in the absence of an estrogen receptor ligand. In some embodiments, the Myc peptide is a Myc-GR fusion peptide. In some embodiments, a method described herein further comprises contacting the cell (e.g., a mammalian cell) with a glucocorticoid receptor ligand. In some embodiments, the cell (e.g., a mammalian cell) is contacted with the selected antigen in the absence of an glucocorticoid receptor ligand.

In some embodiments, provided herein is a method of producing an antibody comprising: (a) contacting a cell comprising Myc (e.g., recombinant Myc) with a selected antigen; (b) recovering the cell (e.g., a mammalian cell) comprising Myc (e.g., recombinant Myc) wherein the cell (e.g., a mammalian cell) is now an immortal cell; and (c) isolating the antibody from the immortal cell wherein the antibody binds specifically to the selected antigen. In some embodiments, the onco-peptide is a fusion peptide. In some embodiments, the onco-peptide is a fusion peptide comprising a PTD. In some embodiments, the onco-peptide is TAT-MYC. In some embodiments, the onco-peptide is Myc-ER. In some embodiments, the onco-peptide is Myc-GR. In some embodiments, the antibody is human or humanized. In some embodiments, the antibody is CDR engrafted. In some embodiments, the antibody is chimeric. In some embodiments, the antibody is a human IgG. In some embodiments, the antibody is or comprises one or more polypeptides derived from a human IgG1, IgG4, IgG2, IgD, IgA or IgM. In some embodiments, the cell (is a mammalian cell. In some embodiments, the cell (e.g., a mammalian cell) is a chicken B-cell. In some embodiments, the cell (e.g., a mammalian cell) is a mouse cell. In some embodiments, the cell (e.g., a mammalian cell) is present in an organism. In some embodiments, the organism is a xenomouse. In some embodiments, the cell (e.g., a mammalian cell) is an AN1/T3 cell. In some embodiments, the cell (e.g., a mammalian cell) is a HSC. In some embodiments, the cell (e.g., a mammalian cell) is an immature B-cell. In some embodiments, the cell (e.g., a mammalian cell) comprises a nucleic acid sequence (e.g., a transgenic sequence) encoding a Myc peptide (e.g., a recombinant Myc peptide (e.g., a Myc fusion peptide as described herein)). In some embodiments, the Myc peptide is a fusion peptide. In some embodiments, the Myc peptide is a TAT-Myc peptide as described herein. In some embodiments, the cell (e.g., a mammalian cell) comprises one or more nucleic acid sequences (e.g., transgenic sequences) that encode a human or humanized antibody. In some embodiments, the cell (e.g., a mammalian cell) comprises cell surface expression of CD79. In some embodiments, the cell (e.g., a mammalian cell) comprises a cell surface B-cell receptor. In some embodiments, the cell (e.g., a mammalian cell) binds specifically to the selected antigen. In some embodiments, the cell (e.g., a mammalian cell) is anergic or tolerant to the selected antigen. In some embodiments, the cell (e.g., a mammalian cell) is anergic or tolerant to the selected antigen prior to contacting antigen in the presence of Myc (e.g., recombinant Myc) activity. In some embodiments, the Myc peptide is a fusion peptide. In some embodiments, the Myc peptide is a TAT-Myc peptide as described herein. In some embodiments, the cell (e.g., a mammalian cell) is mortal (i.e., not immortalized) and/or non-malignant. In some embodiments, the cell (e.g., a mammalian cell) is mortal (i.e., not immortalized) and/or non-malignant prior to contacting antigen in the presence of Myc (e.g., recombinant Myc) activity. In some embodiments, the cell (e.g., a mammalian cell) comprises an intact, functional salvage pathway for purine biosynthesis. In some embodiment the cell (e.g., a mammalian cell) comprises a functional hypoxanthine-guanine phosphoribosyltransferase enzyme. In some embodiments, the immortal cell is malignant. In some embodiments, the immortal cell is a lymphoma. In some embodiments, the immortal cell expresses CD79. In some embodiments, the immortal cell comprises Myc (e.g., recombinant Myc) activity. In some embodiments, the immortal cell comprises an intact, functional salvage pathway for purine biosynthesis. In some embodiment the immortal cell comprises a functional hypoxanthine-guanine phosphoribosyltransferase enzyme. In some embodiments, the immortal cell comprises no more than one nucleus. In some embodiments, the immortal cell is not a hybridoma. In some embodiments, the immortal cell is not a myeloma. In some embodiments, the immortal cell comprises the same number of chromosomes as were present in the cell (e.g., a mammalian cell) Myc (e.g., recombinant Myc) activity prior to contacting the selected antigen. In some embodiments, the immortal cell comprises no more than 5 additional chromosomes than were present in the cell (e.g., a mammalian cell) Myc (e.g., recombinant Myc) activity prior to contacting the selected antigen. In some embodiments, the immortal cell comprises no more than 4 additional chromosomes than were present in the cell (e.g., a mammalian cell) Myc (e.g., recombinant Myc) activity prior to contacting the selected antigen. In some embodiments, the immortal cell comprises no more than 3 additional chromosomes than were present in the cell (e.g., a mammalian cell) Myc (e.g., recombinant Myc) activity prior to contacting the selected antigen. In some embodiments, the immortal cell comprises no more than 2 additional chromosomes than were present in the cell (e.g., a mammalian cell) Myc (e.g., recombinant Myc) activity prior to contacting the selected antigen. In some embodiments, the immortal cell comprises no more than 1 additional chromosome than was present in the cell (e.g., a mammalian cell) Myc (e.g., recombinant Myc) activity prior to contacting the selected antigen. In some embodiments, the immortal cell comprises no additional chromosomes than were present in the cell (e.g., a mammalian cell) Myc (e.g., recombinant Myc) activity prior to contacting the selected antigen. In some embodiments, Myc (e.g., recombinant Myc) activity is inducible. In some embodiments, Myc (e.g., recombinant Myc) activity is inducible and Myc (e.g., recombinant Myc) activity is not present in the cell (e.g., a mammalian cell) prior to contact with antigen. In some embodiments, the cell (e.g., a mammalian cell) over-expresses Myc. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof. In some embodiments, the selected antigen is an auto antigen, a self antigen or a tolerant antigen. In some embodiments, the selected antigen is an auto antigen or a self antigen that is native to the organism. In some embodiments, the selected antigen is homologous to an auto antigen, self antigen or tolerant antigen. In some embodiments, the selected antigen is from 60-100% homologous. In some embodiments, the selected antigen is 60, 65, 70, 75, 80, 85, 90 or 95% homologous to a self antigen, auto antigen or tolerant antigen. In some embodiments, the selected antigen is 91, 92, 93, 94, 95, 96, 97, 98 or 99% homologous to a self antigen, auto antigen or tolerant antigen. In some embodiments, the selected antigen binds to a BCR but fails to transduce a signal through the BCR in the absence of Myc (e.g., recombinant Myc) activity. In some embodiments, the selected antigen fails to induce an immune response when immunized into an organism in the absence of Myc (e.g., recombinant Myc) activity. In some embodiments, contacting a cell comprising Myc (e.g., recombinant Myc) activity with the selected antigen comprises over-expression of the selected antigen in an organism by a nucleic acid sequence (e.g., a transgenic sequence) encoding the selected antigen. In some embodiments, contacting a cell comprising Myc (e.g., recombinant Myc) activity with the selected antigen comprises over-expression of the selected antigen in the cell (e.g., a mammalian cell) by a nucleic acid sequence (e.g., a transgenic sequence) encoding the selected antigen. In some embodiments, contacting a cell comprising Myc (e.g., recombinant Myc) activity with the selected antigen comprises immunizing an organism with the selected antigen.

In some embodiments, a method described herein is used to produce immortal cell lines that produce human antibodies. In some embodiments, organisms are produced that are genetically altered to produce human antibodies and over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, the organisms are mice (e.g., a xenomouse). In some embodiment the organisms are produced by cross breeding an organism that is genetically altered to produce a human antibody with an organism that over-expresses Myc. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, the organism is genetically altered to produce a human antibody, a CDR engrafted antibody or a chimeric antibody. In some embodiments, a mouse strain that carries a transgenic BAC construct encoding the human immunoglobulin locus (IgH and IgL) is crossed with a mouse that that over-expresses Myc. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, the mouse that over-expresses Myc is an Eμ-MYC mouse or a MMTV-rtTA/TRE-MYC mouse. In some embodiments, the mouse that over-expresses Myc expresses Myc-ER. In some embodiments, the mouse that over-expresses Myc expresses Myc-GR. In some embodiments, organisms that are genetically altered to produce human antibodies and over-express MYC are exposed to an antigen. In some embodiments, organisms produced that are genetically altered to produce human antibodies and over-express MYC are immunized with an antigen. In some embodiments, organisms produced that are genetically altered to produce human antibodies and over-express MYC also express a self antigen, neo-self antigen, an auto antigen or an antigen. In some embodiments, hematopoietic stem cells are produced from the organisms described herein that are genetically altered to produce human antibodies and that over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, hematopoietic stem cells produced from any animal described herein are used to generate immortal antibody producing B-cells. In some embodiments, immortal antibody producing B-cells are produced by the method described herein using organisms that are genetically altered to produce human antibodies and that over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof.

In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, the antibodies produce by the methods described herein are humanized antibodies, CDR engrafted antibodies or chimeric antibodies.

In some embodiments, provided herein is a method of producing an antibody comprising: (a) contacting a cell comprising Myc (e.g., recombinant Myc) activity with a selected antigen, wherein the cell (e.g., a mammalian cell) is present in an organism (e.g., a mammal), (b) recovering the cell (e.g., a mammalian cell) wherein the cell (e.g., a mammalian cell) is now an immortal cell and (c) isolating the antibody from the immortal cell wherein the antibody binds specifically to the selected antigen. In some embodiments, Myc is a fusion peptide. In some embodiments, Myc is a fusion peptide comprising a PTD. In some embodiments, Myc is TAT-MYC. In some embodiments, Myc is Myc-ER. In some embodiments, Myc is Myc-GR. In some embodiments, the organism is a xenomouse.

In some embodiments, the organism (e.g., a mammal) is obtained by: (a) presenting an immuno-deficient organism (e.g., a mammal); and (b) administering to the organism (e.g., a mammal) a plurality of hematopoietic stem cells that over-express MYC. In some embodiments, MYC encodes a fusion peptide. In some embodiments, MYC encodes a fusion peptide comprising a PTD. In some embodiments, MYC encodes TAT-MYC. In some embodiments, MYC encodes Myc-ER. In some embodiments, MYC encodes Myc-GR. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, the cell (e.g., a mammalian cell) is derived from the plurality of hematopoietic stem cells that over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, the immuno-deficient organism (e.g., a mammal) is obtained by irradiating the organism (e.g., a mammal). In some embodiments, the immuno-deficient organism (e.g., a mammal) is a Rag-1ko, Rag-2, SCID, DNA-PK, Ku70, Ku80, XRCC4, or μMT mouse. In some embodiments, the organism (e.g., a mammal) expresses the selected antigen. In some embodiments, a method described herein further comprises recovering the antibody produced by the antibody producing cell. In some embodiments, a method described herein further comprises subjecting the antibody producing cell to conditions that induce over-expression of MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof. In some embodiments, the nucleic acid sequence (e.g., a transgenic sequence) that encodes the Myc peptide comprises an inducible promoter or a B-cell-selective promoter. In some embodiments, prior to isolating the antibody producing cell from the organism (e.g., a mammal) the antibody producing cell is subjected to conditions that induce over-expression of MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof.

In some embodiments, provided herein is a method of producing a human or humanized antibody comprising:
 a. providing an antibody producing human cell;
 b. isolating a human gene that encodes the antibody from the antibody producing human cell; and
 c. introducing (or otherwise providing to) the human gene that encodes the antibody into an cell (e.g., a mammalian cell) that comprises nucleic acid sequence (e.g., a transgenic sequence) that encodes an onco-peptide (e.g., recombinant onco-peptide; e.g., Myc).

In some embodiments, the human gene encodes human IgH and IgL, wherein the IgH and IgL together form an antibody that specifically binds the selected antigen. In some embodiments, the cell (e.g., a mammalian cell) is a B-cell. In some embodiments, a method described herein further comprises transplanting the cell (e.g., a mammalian cell) into a mouse. In some embodiments, the human gene isolated encodes a first antibody and a second antibody. In some embodiments, a method described herein further comprises recovering the antibody from the cell (e.g., a mammalian cell). In some embodiments, the nucleic acid sequence (e.g., a transgenic sequence) that encodes the Myc peptide comprises an inducible promoter or a B-cell-selective promoter. In some embodiments, the Myc peptide is a Myc-ER fusion peptide. In some embodiments, the Myc peptide is a Myc-GR fusion peptide. In some embodiments, the Myc peptide is a TAT-Myc fusion peptide disclosed herein.

In some embodiments, provided herein is a method of producing a human or humanized antibody comprising: (a) introducing (or otherwise providing to) at least one gene encoding a human immunoglobulin into a cell that over-expresses Myc; and (b) isolating the encoded human immunoglobulin.

In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof.

In some embodiments, peripheral blood B-cells are obtained from a human. In some embodiments, the human has a serum antibody titer to a certain antigen. The B-cells are obtained using standard approaches. In some embodiments, the B-cells are enriched or purified by any suitable method. In some embodiments, purified B-cells are panned on plastic plates coated with the selected antigen in order to enrich for those B-cells with a specificity of interest. In some embodiments, the selected antigen is conjugated to magnetic beads that are used to isolate the B-cells with the specificity of interest. In some embodiments, nucleic acids, that encode for the heavy and light chain of an antibody, are isolated from enriched populations of antigen specific B-cells. In some embodiments, nucleic acids are isolated from purified antigen specific B-cells. In some embodiments, nucleic acids encoding the heavy and light chain of an antibody are isolated by RT-PCR or PCR. In some embodiments, enriched populations of antigen specific B cells are single-cell sorted into terasaki plates for single cell RT-PCR. In some embodiments, nucleic acids encoding the variable regions for the heavy and light chain of an antibody are isolated.

In some embodiments, nucleic acids encoding human antibodies are transferred into vectors to enable the expression of the human antibodies in cells that over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, the vectors are plasmids or viral vectors. In some embodiments, nucleic acids encoding the variable regions of a human antibody are transferred into a vector cassette comprising the constant region of a human antibody. Using this process or any other suitable process, a variety of human antibodies with defined antigen specificity are produced of the desired class, subclass or isotype. In some embodiments, cDNA fragments encoding human variable regions are cloned into retroviral vectors that encode a human heavy and light chain constant region. In some embodiments, the resulting vectors encoding human antibodies are introduced, by any suitable method, into hematopoietic stem cells that over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. Immortalized B-cells are then produced by methods described herein. In some embodiments, hematopoietic stem cells are derived from MMTV-tTA/TRE-MYC/Rag-1 knock out mice, Eµ-MYC/Rag-1 knock out mice, or bone marrow from a Rag-1 knock out mouse that was transduced with a retrovirus directing the over-expression of MYC. In some embodiments, cells expressing human antibodies and Myc are used to reconstitute immuno-deficient organisms and are subject to the protocols described herein to produce antibody or immortal antibody producing B-cells. The resulting cell lines obtained from this approach encode human immunoglobulin sequences specific for the protein of interest. In some embodiments, this is an approach for the generation of cocktails of inhibitory antibodies for viral infections, tumors, bacteria and fungi, etc.

As disclosed herein, a number of methods are provided to produce antigen-specific non-human (e.g., mouse) antibodies from hematopoietic stem cells or B-cells that over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof. In some embodiments, provided herein, antigen specific non-human antibodies are humanized and the humanized antibodies are expressed in hematopoietic stem cells or B-cells that over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, nucleic acids encoding the selected antigen-specific mouse antibodies are isolated from any source by any suitable method. In some embodiments, the nucleic acids encoding the selected antigen-specific mouse antibodies are isolated from a hybridoma that expresses an antibody of interest. In some embodiments, the nucleic acids encoding the selected antigen-specific non-human (e.g., mouse) antibodies are isolated from any antibody producing cell described herein. In some embodiments, the nucleic acids encoding the selected antigen-specific mouse antibodies are isolated from hematopoietic stem cells that over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, the nucleic acids encoding the selected antigen-specific non-human (e.g., mouse) antibodies are isolated from immortalized B-cells that over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, isolated nucleic acids that encode antigen-specific antibodies are genetically altered to encode humanized, CDR engrafted, or chimeric antibodies. In some embodiments, PCR is used to amplify the rearranged VDJ joint sequence derived from the murine Ig heavy chain and VJ regions from the Ig light chain loci. In some embodiments, the PCR-amplified fragments are cloned into a retroviral plasmid that encodes a human Ig heavy chain and human Ig light chain. In some embodiments, the PCR-amplified fragments are cloned into any vector that directs the expression of the desired antibody. In some embodiments, the Ig heavy chain and light chain sequences are spaced by an IRES element, such that both cDNAs are expressed from the same viral vector. A number of different viral vectors are known in the art that enable the generation of different antibody isotypes, classes, and subclasses. In some embodiments, the sequences encoding the Fc regions are further modified to alter effector function, the ability to trigger autoimmune reactions or the ability to induce immune-complex deposition problems.

In some embodiments, the resulting vectors or retroviruses are introduced into hematopoietic stem cells that over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, hematopoietic stem cells that over-express MYC are obtained from an organism that inducibly expresses recombinant Myc (e.g., MMTV-tTA/TRE-MYC/Rag-1 knock out mice). In some embodiments, the hematopoietic stem cells described herein are transferred into a lethally irradiated animal, e.g., lethally irradiated C57/BL6 wild type mice. In some embodiments, the resulting mice generate immortal monoclonal antibody producing cells that are antigen specific with all of the added features of the humanized antibodies.

In some embodiments, nucleic acids encoding human antibodies are isolated from human B-cells obtained from either healthy donors, patients who suffer from antibody-mediated autoimmune diseases (e.g. Sjögren's syndrome, Hashimoto's thyroiditis, Systemic Lupus Erythematosus, Waldenström's macroglobulinemia, etc), or patients who suffer from Non-Hodgkin's lymphomas (e.g. Burkitt's lymphomas, Follicular Like Lymphomas, Diffuse Large B-cell lymphomas, MGUS and Multiple Myeloma). In certain embodiments, the nucleic acids encoding human antibodies are cloned, using any suitable manner, into retroviral vectors as described herein to produce retroviral libraries. In some embodiments, two different retroviral vectors are used to expedite the generation of the retroviral libraries. In some embodiments, the resulting vectors encoding human antibodies are introduced, using any suitable manner, into hematopoietic stem cells that over-express MYC. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In certain embodiments, such hematopoietic stem cells are then differentiated to produce immortalized B-cells (including conditionally immortalized) that express the selected antigen encoded by the nucleic acids cloned. In some embodiments, hematopoietic stem cells are derived from an organism that conditionally expresses Myc (e.g., MMTV-tTA/TRE-MYC/Rag-1 knock out mice), an organism that expresses recombinant Myc in a B-cell (e.g., Eµ-MYC/Rag-1 knock out mice), or bone marrow from an immuno-deficient animal (e.g., a Rag-1 knock out mouse) that was transduced with a retrovirus directing the over-expression of MYC. In some embodiments, cells expressing human antibodies and Myc are used to reconstitute immuno-deficient organisms and are subject to the protocols described herein to produce antibody or immortal antibody producing B-cells. In some embodiments, the retroviral libraries are used to transduce hematopoietic stem cells obtained from an organism that conditionally expresses Myc (e.g., MMTV-tTA/TRE-MYC/Rag-1 knock out mice) in order to generate bone marrow chimeric mice. In some embodiments, the bone marrow chimeric mice only make B-cells that express human antibodies and are maintained on a doxycycline containing diet until they are ready for immunization (in order to suppress MYC expression). In some embodiments, these mice are immunized in the absence of doxycycline to induce over-expression of MYC in their B-cells. In some embodiments, the reactive, antigen-specific B-cells are isolated and enriched by panning against an antigen. In some embodiments, reactive, antigen-specific B-cells are isolated and enriched by other selection methods known in the art. Examples of selections methods include but are not limited to panning, cell sorting and magnetic bead isolation techniques. In some embodiments, antigen-specific populations are grown in the presence of Myc (e.g., recombinant Myc) activity in order to produce immortal monoclonal cell lines that generate human antibodies. In some embodiments, antigen-specific populations are grown in the presence of Myc over-expression in order to produce immortal monoclonal cell lines that generate human antibodies. In some embodiments, the approach described above is used to specifically isolate human IgA antibodies to specific antigens. Human IgA antibodies are highly sought after for prophylaxis. In some embodiments, the Fc region of any antibody produced herein is easily exchanged or altered to produce different classes, subclasses, or isotypes or antibodies with modified effector functions.

Onco-Peptides

In certain embodiments, any onco-peptide is suitable for use herein. In some embodiments, the onco-peptide promotes cell viability, cell immortality, cell growth and/or cell proliferation. In specific embodiments, an onco-peptide is, by way of non-limiting example, a Myc peptide (e.g., a recombinant Myc peptide (e.g., a Myc fusion peptide as described herein)), a Notch-1 peptide (e.g., a recombinant peptide), an Akt peptide (e.g., a recombinant peptide), an hTERT peptide (e.g., a recombinant peptide), and the like. Further examples of onco-peptides (e.g., peptides encoded by a protooncogene or an oncogene) are set forth in U.S. 2007/0116691, which is hereby incorporated by reference for such disclosures. In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is Myc-ER. In some embodiments, the Myc peptide is Myc-GR.

While in certain embodiments, described herein, Myc is the onco-peptide utilized, it is to be understood that any onco-peptide that promotes cell viability, cell immortality, cell growth and/or cell proliferation is optionally substituted for the Myc peptide. In some embodiments, over-expression of an onco-peptide results in onco-peptide activity.

For example, Myc-over-expressing BCR$^{HEL}$ transgenic B-cells mount a vigorous response to soluble HEL (hen egg-white lysozyme) and engender a polyclonal autoimmune lymphoprolifeative disease prior to the onset of a malignancy (FIGS. 1-6) The over-expression of MYC in auto reactive B-cells renders the B-cells independent of T-cell help, through Myc's abilities to provide proliferative and survival signals. In some embodiments, the expanded population of Myc over-expressing, auto reactive B-cells develop into a B-cell lymphoma that remains dependent upon both continuous exposure to its cognate antigen and Myc (e.g., recombinant Myc) activity. In some embodiments, B-cells are harvested from, e.g., the lymph nodes, spleens and/or bone marrow of tumor-bearing organisms. In certain embodiments, such B-cells are used to establish many cell lines that expressed the BCR$^{HEL}$ nucleic acid sequence (e.g., a transgenic sequence) and secrete anti-HEL antibody, without requiring cell fusion of the primary cells to a fusion partner.

In some embodiments, the onco-peptide is a fusion peptide. In certain embodiments, fusion peptides include, e.g., a transduction domain and/or a receptor (e.g., Tat-Myc, Myc-ER, Myc-GR, Tat-Myc-ER, and Tat-Myc-GR).

In some embodiments, the onco-peptide is Bcl-2, Mcl-1, a Bcl-2 family member or a derivative thereof. In some embodiments, the onco-peptide is Ras, H-Ras, K-Ras, N-Ras, ERK, c-erbB2, RET or TRK or a derivative thereof. In some embodiments, provided herein is a method of producing an antibody specific for an antigen, comprising contacting a cell (e.g., a mammalian cell) comprising a nucleic acid sequence (e.g., a transgenic sequence) that encodes SV40 T-Ag with a selected antigen. In certain embodiments, an onco-peptide of a method disclosed herein is optionally substituted with a growth factor that promotes cell viability, cell immortality, cell growth and/or cell proliferation. In some embodiments, provided herein is a method of producing an antibody specific for an antigen, comprising contacting a cell (e.g., a mammalian cell) comprising a nucleic acid sequence (e.g., a transgenic sequence) that encodes a growth factor receptor polypeptide with a selected antigen. Examples of growth factors receptors include but are not limited to epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. In some embodiments, provided herein is a method of producing an antibody specific for an antigen, comprising contacting a cell (e.g., a mammalian cell) comprising a nucleic acid sequence (e.g., a transgenic sequence) that encodes a dominant negative tumor suppressor polypeptide with a selected antigen. In some embodiments, the dominant negative suppressor polypeptide is a dominant negative of p53.

In some embodiments, provided herein is a method of producing an antibody specific for an antigen, comprising introducing (or otherwise providing to) a selected antigen into an organism (e.g., a mammal), wherein the organism (e.g., a mammal) comprises a nucleic acid sequence (e.g., a transgenic sequence) that encodes Bcl-2, Mcl-1, a Bcl-2 family member, Ras, H-Ras, K-Ras, N-Ras, ERK, c-erbB2, RET or TRK, SV40 T-Ag, EGFr, PDGFr, erbB2, erbB4, VEGFr, TIE-2, IGFI receptor, cfms, BTK, ckit, cmet, an FGF receptor, a Trk receptor, an eph receptor, RET and/or a dominant negative of p53. In some embodiments, the method further comprises generating immortal antigen-specific B-cells from the organism (e.g., a mammal). In some embodiments, the organism is a xenomouse. In some embodiments, the method further comprises generating hematopoietic stem cells that are genetically altered to express at least one of the listed nucleic acid sequences (e.g., a transgenic sequence). In some embodiments, a method disclosed herein further comprises the preparation of human antibodies. In some embodiments, the method further comprises recovering the antibody specific for an antigen from a plurality of recombinant B-cells generated by the expansion of the B-cell. In some embodiments, a method disclosed herein further comprises generating antibody producing immortal, antigen-specific B-cells from an anergic B-cell that over-expresses at least one of the listed nucleic acid sequences (e.g., a transgenic sequence). In some embodiments, a method disclosed herein further comprises an antigen that is a self-antigen or an autoantigen. In some embodiments, a method disclosed herein further comprises contacting a B-cell with the selected antigen and over-expressing the nucleic acid sequence (e.g., a transgenic sequence). In some embodiments, a method disclosed herein comprises immunizing the organism (e.g., a mammal) with the selected antigen. In some embodiments, the organism (e.g., a mammal) further carries and expresses a nucleic acid sequence (e.g., a transgenic sequence) encoding the selected antigen. In some embodiments, a method disclosed herein further comprises a nucleic acid sequence (e.g., a transgenic sequence) encoding a Myc peptide (e.g., a recombinant Myc peptide (e.g., a Myc fusion peptide as described herein)). In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is Myc-ER. In some embodiments, the Myc peptide is Myc-GR.

In some embodiments, provided herein is a method of producing an antibody selective for an antigen, comprising (a) administering to an immunodeficient organism (e.g., a mammal) a plurality of hematopoietic stem cells that comprise a nucleic acid sequence (e.g., a transgenic sequence) encoding Bcl-2, Mcl-1, a Bcl-2 family member, Ras, H-Ras, K-Ras, N-Ras, ERK, c-erbB2, RET or TRK, SV40 T-Ag, EGFr, PDGFr, erbB2, erbB4, VEGFr, TIE-2, IGFI receptor, cfms, BTK, ckit, cmet, an FGF receptor, a Trk receptor, an eph receptor, RET and/or a dominant negative of p53; and (b) introducing (or otherwise providing to) a selected antigen into the immuno-deficient organism (e.g., a mammal). In some embodiments, the organism is a xenomouse. In some embodiments, the hematopoietic stem cells further comprise a nucleic acid sequence (e.g., a transgenic sequence) encoding a Myc peptide. In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is Myc-ER. In some embodiments, the Myc peptide is Myc-GR. In some embodiments, a method disclosed herein further comprises inducing a plurality of the hematopoietic stem cells to differentiate into B-cells. In some embodiments, a method described herein further comprises recovering a plurality of the B-cells that express the antibody selective for the selected antigen from the immuno-deficient organism (e.g., a mammal). In some embodiments, a method described herein further comprises recovering the antibody from the plurality of B-cells that express the antibody. In some embodiments, the nucleic acid sequence (e.g., a transgenic sequence) comprises an inducible promoter or a B-cell-selective promoter. In some embodiments, the nucleic acid sequence (e.g., a transgenic sequence) comprises an inducible promoter comprising one or more TREs. In some embodiments, the hematopoietic stem cells express tTA or rtTA. In some embodiments, a method described herein providing doxycycline, tetracycline, or an analog thereof to the immuno-deficient organism (e.g., a mammal) for a period of time sufficient to suppress the tTA-dependent transactivation, and withdrawing the doxycycline, tetracycline, or analog thereof after the period to induce tTA-dependent transactivation. In some embodiments, the nucleic acid sequence (e.g., a transgenic sequence) comprises a B-cell-selective promoter and the B-cell selective promoter is the Eµ promoter. In some embodiments, the organism or cell further comprises a nucleic acid sequence (e.g., a transgenic sequence) encoding a fusion peptide. In some embodiments, the selected antigen is a self-antigen or an auto antigen. In some embodiments, the immuno-deficient organism (e.g., a mammal) is obtained by irradiating the organism (e.g., a mammal). In some embodiments, the immuno-deficient organism (e.g., a mammal) is a Rag-1ko, Rag-2, SCID, DNA-PK, Ku70, Ku80, XRCC4, or µMT mouse. In some embodiments, the immuno-deficient organism (e.g., a mammal) expresses the selected antigen. In some embodiments, the immuno-deficient organism (e.g., a mammal) that expresses the selected antigen is transgenic for the selected antigen. In some embodiments, the selected antigen is introduced by transfection with a nucleic acid expression vector or infection with a recombinant virus expression vector. In some embodiments, the recombinant virus expression vector is a recombinant lentivirus.

In some embodiments, provided herein is a method of producing a human or humanized antibody comprising: (a) providing a cell (e.g., a mammalian cell) that expresses human antibodies and comprises nucleic acid sequence (e.g., a transgenic sequence) that encodes a recombinant Bcl-2, Mcl-1, a Bcl-2 family member, Ras, H-Ras, K-Ras, N-Ras, ERK, c-erbB2, RET or TRK, SV40 T-Ag, EGFR, PDGFr, erbB2, erbB4, VEGFR, TIE-2, IGFI receptor, cfms, BTK, ckit, cmet, an FGF receptor, a Trk receptor, an eph receptor, RET and/or a dominant negative p53 polypeptide; and (b) contacting the cell (e.g., a mammalian cell) with a selected antigen. In some embodiments, the cell (e.g., a mammalian cell) that expresses human antibodies and comprises nucleic acid sequence (e.g., a transgenic sequence) that encodes a recombinant Bcl-2, Mcl-1, a Bcl-2 family member, Ras, H-Ras, K-Ras, N-Ras, ERK, c-erbB2, RET or TRK, SV40 T-Ag, EGFR, PDGFr, erbB2, erbB4, VEGFR, TIE-2, IGFI receptor, cfms, BTK, ckit, cmet, an FGF receptor, a Trk receptor, an eph receptor, RET and/or a dominant negative p53 polypeptide is a B-cell. In some embodiments, the cell (e.g., a B-cell) inducibly over-expresses Myc. In some embodiments, the cell (e.g., a B-cell) inducibly over-expresses the recombinant Bcl-2, Mcl-1, a Bcl-2 family member, Ras, H-Ras, K-Ras, N-Ras, ERK, c-erbB2, RET or TRK, SV40 T-Ag, EGFr, PDGFr, erbB2, erbB4, VEGFr, TIE-2, IGFI receptor, cfms, BTK, ckit, cmet, an FGF receptor, a Trk receptor, an eph receptor, RET and/or dominant negative p53 polypeptide. In some embodiments, the cell (e.g., a mammalian cell) that expresses human antibodies and comprises nucleic acid sequence (e.g., a transgenic sequence) a that encodes Bcl-2, Mcl-1, a Bcl-2 family member, Ras, H-Ras, K-Ras, N-Ras, ERK, c-erbB2, RET or TRK, SV40 T-Ag, EGFr, PDGFr, erbB2, erbB4, VEGFr, TIE-2, IGFI receptor, cfms, BTK, ckit, cmet, an FGF receptor, a Trk receptor, an eph receptor, RET and/or dominant negative p53 polypeptide is present in an organism (e.g., a mammal), and wherein the method further comprises recovering the antibody producing cell from the organism (e.g., a mammal). In some embodiments, the organism is a xenomouse. In some embodiments, the organism (e.g., a mammal) is a mouse. In some embodiments, the organism (e.g., a mammal) utilized in a method described herein is obtained by: (a) presenting an immuno-deficient organism (e.g., a mammal); and (b) administering to the organism (e.g., a mammal) a plurality of hematopoietic stem cells that over-express Bcl-2, Mcl-1, a Bcl-2 family member, Ras, H-Ras, K-Ras, N-Ras, ERK, c-erbB2, RET or TRK, SV40 T-Ag, EGFr, PDGFr, erbB2, erbB4, VEGFr, TIE-2, IGFI receptor, cfms, BTK, ckit, cmet, an FGF receptor, a Trk receptor, an eph receptor, RET and/or a dominant negative p53 polypeptide. In some embodiments, the immuno-deficient organism (e.g., a mammal) is obtained by irradiating the organism (e.g., a mammal). In some embodiments, the immuno-deficient organism (e.g., a mammal) is a Rag-1ko, Rag-2, SCID, DNA-PK, Ku70, Ku80, XRCC4, or µMT mouse. In some embodiments, the organism (e.g., a mammal) expresses the selected antigen. In some embodiments, a method described herein further comprises recovering the antibody produced by the antibody producing cell or animal. In some embodiments, a method described herein further comprises subjecting the antibody producing cell to conditions that induce over-expression of Bcl-2, Mcl-1, a Bcl-2 family member, Ras, H-Ras, K-Ras, N-Ras, ERK, c-erbB2, RET or TRK, SV40 T-Ag, EGFr, PDGFr, erbB2, erbB4, VEGFr, TIE-2, IGFI receptor, cfms, BTK, ckit, cmet, an FGF receptor, a Trk receptor, an eph receptor, RET and/or a dominant negative p53 polypeptide.

In some embodiments, provided herein is a method of producing a human or humanized antibody comprising: (a) providing an antibody producing human cell; (b) isolating a human gene that encodes the antibody from the antibody producing human cell; and (c) introducing (or otherwise providing to) the human gene that encodes the antibody into an cell (e.g., a mammalian cell) that comprises nucleic acid sequence (e.g., a transgenic sequence) that encodes a Bcl-2, Mcl-1, a Bcl-2 family member, Ras, H-Ras, K-Ras, N-Ras, ERK, c-erbB2, RET or TRK, SV40 T-Ag, EGFr, PDGFr, erbB2, erbB4, VEGFr, TIE-2, IGFI receptor, cfms, BTK, ckit, cmet, an FGF receptor, a Trk receptor, an eph receptor, RET and/or a dominant negative p53 polypeptide. In some embodiments, the cell (e.g., a mammalian cell) over-expresses a Myc peptide (e.g., a recombinant Myc peptide (e.g., a Myc fusion peptide as described herein)). In some embodiments, the Myc peptide is a fusion peptide. In some embodiments, the Myc peptide is a TAT-Myc peptide as described herein. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof. In some embodiments, the human gene encodes human IgH and IgL, wherein the IgH and IgL together form an antibody that specifically binds the selected antigen. In some embodiments, the cell (e.g., a mammalian cell) is a B-cell. In some embodiments, a method described herein further comprises transplanting the cell (e.g., a mammalian cell) into a mouse. In some embodiments, the human gene isolated encodes a first antibody and a second antibody. In some embodiments, a method described herein further comprises recovering the antibody from the cell (e.g., a mammalian cell).

In some embodiments, provided herein is a method of producing a human or humanized antibody comprising: (a) introducing (or otherwise providing to) at least one gene encoding a human immunoglobulin into a cell that over-expresses a Bcl-2, Mcl-1, a Bcl-2 family member, Ras, H-Ras, K-Ras, N-Ras, ERK, c-erbB2, RET or TRK, SV40 T-Ag, EGFr, PDGFr, erbB2, erbB4, VEGFr, TIE-2, IGFI receptor, cfms, BTK, ckit, cmet, an FGF receptor, a Trk receptor, an eph receptor, RET and/or a dominant negative p53 polypeptide; and (b) isolating the encoded human immunoglobulin.

In some embodiments, provided herein is an isolated B-cell for producing a human or humanized antibody, wherein the B-cell over-expresses a Bcl-2, Mcl-1, a Bcl-2 family member, Ras, H-Ras, K-Ras, N-Ras, ERK, c-erbB2, RET or TRK, SV40 T-Ag, EGFr, PDGFr, erbB2, erbB4, VEGFr, TIE-2, IGFI receptor, cfms, BTK, ckit, cmet, an FGF receptor, a Trk receptor, an eph receptor, RET and/or a dominant negative p53 polypeptide. In some embodiments, the B-cell also over-expresses a Myc peptide (e.g., a recombinant Myc peptide (e.g., a Myc fusion peptide as described herein)). In some embodiments, the Myc peptide is a fusion peptide. In some embodiments, the Myc peptide is a TAT-Myc peptide as described herein. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, over-expression of MYC is induced by contacting the cell with a shRNA molecule for Max-1, Mxi-1, MAD, or a combination thereof.

Tolerance

Onco-peptide (e.g., recombinant onco-peptide; e.g., Myc) activity, in some embodiments, terminates (or reduces) B-cell tolerance to an antigen (e.g., a soluble antigen). Therefore, in some embodiments, of a method described herein, the cell (e.g., a mammalian cell) comprising a nucleic acid sequence (e.g., a transgenic sequence) encoding an onco-peptide is tolerant and/or anergic to the selected antigen.

In some embodiments, provided herein is a method of producing an antibody and/or cell that produces an antibody that specifically binds to an antigen, comprising: contacting a cell comprising a nucleic acid sequence (e.g., a transgenic sequence) that encodes an onco-peptide (e.g., recombinant onco-peptide; e.g., Myc) with a selected antigen, wherein in the absence of onco-peptide activity (expression and/or onco-peptide function), the cell (e.g., a mammalian cell) is tolerant and/or anergic to the selected antigen.

In some embodiments, the onco-peptide is a fusion peptide. In some embodiments, the onco-peptide comprises a PTD. In some embodiments, the onco-peptide is a TAT-Myc peptide as described herein. In some embodiments, the onco-peptide is Myc-ER. In some embodiments, the onco-peptide is Myc-GR.

In certain embodiments, the method further comprises recovering one or more B-cells that express the antibody that specifically binds to the selected antigen. In specific embodiments, the selected antigen is a self antigen.

In some embodiments, provided herein is a method of producing an antibody that specifically binds to an antigen comprising:
   a. inducing onco-peptide (e.g., recombinant onco-peptide; e.g., Myc) activity (expression and/or onco-peptide function) in a cell (e.g., B-cell) that expresses the selected antibody and comprises an onco-peptide that is inducibly activated (e.g., Myc-ER, Myc-GR) and/or a nucleic acid sequence (e.g., a transgenic sequence) that encodes an onco-peptide (e.g., TRE-Myyc, TRE-Myc-ER, or TRE-Myc-GR);
   b. recovering the antibody expressed from the organism cell (e.g., B-cell).

In some embodiments, the onco-peptide is a fusion peptide. In some embodiments, the onco-peptide comprises a PTD. In some embodiments, the onco-peptide is a TAT-Myc peptide as described herein. In some embodiments, the onco-peptide is Myc-ER. In some embodiments, the onco-peptide is Myc-GR.

In some embodiments, the organism is a xenomouse.

In some embodiments, in the absence of onco-peptide (activity (expression and/or onco-peptide function), the cell (e.g., a mammalian cell) is tolerant and/or anergic to the selected antigen. In some embodiments, the Myc peptide is a fusion peptide. In some embodiments, the Myc peptide is a TAT-Myc peptide as described herein. In certain embodiments, induction of onco-peptide activity induces proliferation of the cell (e.g., a mammalian cell). Thus, in certain embodiments, the antibody is recovered from a plurality of cells (e.g., B-cells) generated by the expansion of the cell. In specific embodiments, the selected antigen is a self antigen. In some embodiments, the process of recovering an antibody comprises recovering the nucleic acids that encode said antibody.

In some embodiments, provided herein is a method of producing an antibody that specifically binds to a self-antigen comprising:
   a. inducing onco-peptide (e.g., recombinant onco-peptide; e.g., Myc) activity (expression and/or onco-peptide function) in a cell (e.g., B-cell) that expresses the selected antibody and comprises a onco-peptide that is inducibly activated (e.g., Myc-ER, or Myc-GR) and/or a nucleic acid sequence (e.g., a transgenic sequence) that encodes an onco-peptide (e.g., TRE-Myc, TRE-Myc-GR, or TRE-Myc-ER);
b. recovering the antibody expressed from cell (e.g., B-cell).

In some embodiments, the onco-peptide is a fusion peptide. In some embodiments, the onco-peptide comprises a PTD. In some embodiments, the onco-peptide is a TAT-Myc peptide as described herein. In some embodiments, the onco-peptide is Myc-ER. In some embodiments, the onco-peptide is Myc-GR.

In some embodiments, provided herein is a method of producing an antibody that specifically binds to a self-antigen comprising:
a. contacting a cell that expresses the antibody with an onco-peptide (e.g., recombinant onco-peptide; e.g., Myc, TAT-Myc);
b. recovering the antibody expressed from cell (e.g., B-cell).

In some embodiments, the onco-peptide is a fusion peptide. In some embodiments, the onco-peptide comprises a PTD. In some embodiments, the onco-peptide is a TAT-Myc peptide as described herein. In some embodiments, the onco-peptide is Myc-ER. In some embodiments, the onco-peptide is Myc-GR.

In some embodiments, the method comprises: contacting a cell that expresses the antibody with a TAT-Myc fusion peptide disclosed herein; and recovering the antibody expressed from cell (e.g., B-cell).

In some embodiments, in the absence of onco-peptide activity (expression and/or onco-peptide function), the cell (e.g., a mammalian cell) is tolerant and/or anergic to the self antigen.

In some embodiments, the onco-peptide is a fusion peptide. In some embodiments, the onco-peptide comprises a PTD. In some embodiments, the onco-peptide is a TAT-Myc peptide as described herein. In some embodiments, the onco-peptide is Myc-ER. In some embodiments, the onco-peptide is Myc-GR.

In certain embodiments, induction of onco-peptide activity induces proliferation of the cell (e.g., a mammalian cell). Thus, in certain embodiments, the antibody is recovered from a plurality of cells (e.g., B-cells) generated by the expansion of the cell.

In some embodiments, provided herein is a method of producing an antibody selective for an antigen, comprising, (a) inducing Myc (e.g., recombinant Myc) activity in a tolerant B-cell that comprises a Myc peptide or a nucleic acid sequence (e.g., a transgenic sequence) encoding a Myc peptide; (b) expanding the B-cell after the induction; and (c) recovering the expressed antibody that is selective for the selected antigen from a plurality of recombinant B-cells generated by the expansion of the B-cell.

In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is Myc-ER. In some embodiments, the Myc peptide is Myc-GR.

In some embodiments, provided herein is a method of producing an antibody selective for an antigen, comprising, (a) inducing Myc (e.g., recombinant Myc) activity in a B-cell that expresses the antibody, and comprises a Myc peptide or a nucleic acid sequence (e.g., a transgenic sequence) encoding the Myc peptide; (b) expanding the B-cell after the induction; and (c) recovering the expressed antibody from a plurality of recombinant B-cells generated by the expansion of the B-cell.

In some embodiments, the onco-peptide is a fusion peptide. In some embodiments, the onco-peptide comprises a PTD. In some embodiments, the onco-peptide is a TAT-Myc peptide as described herein. In some embodiments, the onco-peptide is Myc-ER. In some embodiments, the onco-peptide is Myc-GR.

In certain embodiments, expansion of a cell (e.g., a mammalian cell or a B-cell) described in the methods herein is caused by the induction of the onco-peptide (e.g., recombinant onco-peptide; e.g., Myc) activity in the cell (e.g., B-cell).

For example, Myc over-expressing Ars.A1 mice break tolerance and develop activated antigen-specific B-cells. Ars.A1 mice express a transgenic B-cell receptor (BCR) specific for the selected antigen arsenate (Ars). In these mice the transgenic BCR specifically binds to arsenate, but exhibits low affinity cross-reactivity with DNA. Immature B cells from these organisms are anergic as a consequence of Ag recognition in the bone marrow. Eu-MYC mice express Myc almost exclusively in B-cells under the control of the immunoglobulin heavy chain gene enhancer. Mice derived from a cross between the Ars.A1 mouse and the Eμ-MYC strain develop a Burkitt's like lymphoma. The tumors are composed of mature, activated B-cells that express arsenate-specific IgM on their surface. Thus, as disclosed herein, in some embodiments, Myc (e.g., recombinant Myc) activity breaks tolerance for auto reactive B-cells in the context of a low-affinity, anti-DNA antibody. In some embodiments, Myc (e.g., recombinant Myc) activity breaks tolerance of B-cells that bind self antigen or auto antigens. In some embodiments, provided herein is a method of producing an antibody that specifically binds to an antigen, comprising, (a) inducing Myc (e.g., recombinant Myc) activity in a B-cell that binds the selected antigen, and comprises a nucleic acid sequence (e.g., a transgenic sequence) encoding the recombinant Myc peptide; (b) expanding the B-cell after the induction; and (c) recovering the expressed antibody from a plurality of recombinant B-cells generated by the expansion of the B-cell.

In some embodiments, the onco-peptide is a fusion peptide. In some embodiments, the onco-peptide comprises a PTD. In some embodiments, the onco-peptide is a TAT-Myc peptide as described herein. In some embodiments, the onco-peptide is Myc-ER. In some embodiments, the onco-peptide is Myc-GR.

In some embodiments, the nucleic acid sequence (e.g., a transgenic nucleic acid sequence) encoding the Myc peptide comprises a B-cell selective promoter.

In some embodiments, provided herein is a method of producing an antibody specific for an antigen, comprising contacting a cell comprising a nucleic acid sequence (e.g., a transgenic sequence) that encodes a Myc peptide with a selected antigen. In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is Myc-ER. In some embodiments, the Myc peptide is Myc-GR.

In some embodiments, the cell (e.g., a mammalian cell) is a B-cell or a cell that expresses a B cell receptor on its cell surface. In some embodiments, the cell (e.g., a mammalian cell) expresses CD79 on its cells surface. In some embodiments, the cell (e.g., a mammalian cell) is a mammalian cell. In some embodiments, the cell (e.g., a mammalian cell) is a B-cell with an intact salvage pathway for purine biosynthesis.

In some embodiments, the nucleic acid sequence (e.g., a transgenic sequence) that encodes a Myc peptide comprises a B-cell-selective promoter operably linked to an open reading frame of the encoded Myc peptide. In some embodiments, the B-cell selective promoter is the Eμ promoter. In some embodiments, the organism (e.g., a mammal) further comprises a nucleic acid sequence (e.g., a transgenic sequence) encoding the selected antigen.

In some embodiments, provided herein is a method of producing an antibody specific for an antigen, comprising (a) contacting a CD79 expressing cell with a selected antigen wherein the CD79 expressing cell comprises Myc, and (b) recovering a CD79 expressing cell that produces an antibody that specifically binds to the selected antigen.

In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is Myc-ER. In some embodiments, the Myc peptide is Myc-GR.

In some embodiments, the recovered CD79 expressing cell that produces an antibody that specifically binds to the selected antigen maintains the same number of chromosomes throughout the process. In some embodiments, the CD79 expressing cell that produces an antibody that specifically binds to the selected antigen produces soluble antibody. In some embodiments, the recovered CD79 expressing cell that produces an antibody that specifically binds to the selected antigen is expanded in vitro and the antibody that specifically binds to the selected antigen is isolated. In some embodiments, the isolated antibody is purified.

In some embodiments, an organism provided in a method disclosed herein is an organism with a B-cell specific expression of an onco-peptide and/or a temporally regulated over-expression of a polypeptide. In some embodiments, the organism is a xenomouse. In certain embodiments, a cell utilized in any process described herein is a cell from such an organism. For example, MMTV-tTA/TRE-MYC mice enable B-cell specific, temporally regulated over-expression of MYC following the withdrawal of doxycycline from the diet. At four months of age and after withdraw of doxycycline, mice derived from a cross between the Ars.A1 mouse and the MMTV-tTA/TRE-MYC mouse generate activated peripheral B-cells and anti-nuclear antibodies. These mice also accumulate immune complex deposits in their kidneys and develop B-cell lymphomas. Generation of immortal antibody producing cell lines from the tumors of these mice does not require cell fusion with a myeloma partner cell.

In some embodiments, any Myc over-expressing organism or cell is utilized in a method described herein. In some embodiments, the organism is a xenomouse. In some embodiments, organisms that over-express MYC predominantly in the B cell population, such as, for example, the Eμ-MYC mouse strain, are utilized.

In some embodiments, organisms or cells that over-express MYC in an inducible manner are utilized. In some embodiments, the organism is a xenomouse. In some embodiments, the Myc over-expression is regulated in a temporal manner and in some embodiments, Myc over-expression is suppressed until the production of the antibodies commences. In some embodiments, the invention comprises the use of the MMTV-tTA/TRE-MYC mouse strain. In MMTV-tTA/TRE-MYC mice, Myc over-expression is commenced by removing the doxycycline or tetracycline from the diet of the mice or mouse cells. In some embodiments, the MMTV-tTA/TRE-MYC mouse strain is administered doxycycline or tetracycline from birth until they are to be used to produce the antibody of interest, thereby minimizing the formation of spontaneous lymphoproliferative diseases.

In some embodiments, MMTV-rtTA/TRE-MYC mouse strains are utilized. In MMTV-rtTA/TRE-MYC mice, Myc over-expression is commenced by the addition of doxycycline or tetracycline to the diet of the mice.

In some embodiments, Myc-ER mice or mouse cells are utilized. In Myc-ER mice and mouse cells, Myc is activated by the addition of estrogen or an analogue of estrogen. In some embodiments, the analogue of estrogen is 4OHT. In some embodiments, alternative inducible gene expression/repression systems are utilized. In some embodiments, any animal that over-expresses Myc is used to produce immortalized antibody producing cells by methods described herein.

In some embodiments, Myc-GR mice or mouse cells are utilized. In Myc-GR mice and mouse cells, Myc is activated by the addition of glucocorticoid or an analogue of glucocorticoid. In some embodiments, alternative inducible gene expression/repression systems are utilized. In some embodiments, any animal that is genetically altered to over-express MYC is used to produce immortalized antibody producing cells by methods described herein.

In some embodiments, antigen responsive immortal B-cell lines are generated from anergic AN1/T3 cell populations found within an organism that over-expresses MYC. In some embodiments, MYC encodes a fusion peptide. In some embodiments, MYC encodes a fusion peptide comprising a PTD. In some embodiments, MYC encodes a TAT-Myc peptide as described herein. In some embodiments, MYC encodes Myc-ER. In some embodiments, MYC encodes Myc-GR.

In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof.

In some embodiments, these organisms express the selected antigen of interest. In some embodiments, the selected antigen is expressed by retroviral-mediated transduction of bone marrow derived hematopoietic stem cells (hematopoietic stem cells) with a recombinant retrovirus directing the expression of the selected antigen, using a standard transgenic approach, or any other method for gene delivery into organisms. In some embodiments, the organisms are exposed to the selected antigen by immunization. In some embodiments, the organisms genetically altered to express Myc are MMTV-tTA/TRE-MYC organisms that are maintained on doxycycline from conception. In some embodiments, the MMTV-tTA/TRE-MYC organisms are MMTV-tTA/TRE-MYC mice.

In some embodiments, lymphocytes comprising the AN1/T3 cell populations are isolated from the spleens of organisms genetically altered to express Myc and are further cultured in vitro. In some embodiments, the lymphocytes comprising the AN1/T3 populations are isolated from the blood, bone marrow, or lymph nodes. In some embodiments, lymphocytes comprising the AN1/T3 cell populations are cultured under conditions in which MYC is over-expressed. In some embodiments, lymphocytes comprising the AN1/T3 cell populations are cultured in the presence of antigen under conditions in which MYC is over-expressed. In some embodiments, lymphocytes comprising the AN1/T3 cell populations are cultured in the presence of antigen under conditions in which MYC is over-expressed. In some embodiments, lymphocytes comprising the AN1/T3 cell populations are cultured in the presence of antigen and Myc (e.g., recombinant Myc) activity. In some embodiments, lymphocytes comprising the AN1/T3 cell populations are cultured in the presence of doxycycline. In some embodiments, the doxycycline concentration is from about 0.01 nM to about 300 nM. In some embodiments, the doxycycline concentration is from about 1 nM to about 100 nM. In some embodiments, the doxycycline concentration is from 40 nM to 60 nM. In some embodiments, tetracycline, or an analogue of tetracycline, is used in place of doxycycline.

In some embodiments, antigen-specific B-cells are selected and isolated by various suitable methods. A multitude of cell selection and cell isolation suitable techniques are available including, but are not limited to flow cytometry, panning, magnetic beads, affinity columns, immunoprecipitation and various means of cell sorting.

In some embodiments, the cultured cells are re-exposed to antigen under condition in which a Myc peptide (e.g., a recombinant Myc peptide) is activated. In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is a Myc-ER peptide as described herein. In some embodiments, the Myc peptide is a Myc-GR peptide as described herein.

In some embodiments, the selected antigen-specific B-cells or cells that express an antigen-specific antibody are cloned and expanded without the need for cell fusion to a partner cell.

In some embodiments, provided herein is a method of producing an antibody specific for an antigen, comprising (a) providing an AN1/T3 B-cell wherein the AN1/T3 B-cell comprises a nucleic acid sequence (e.g., a transgenic sequence) encoding a Myc peptide, (b) contacting the AN1/T3 B-cell with an antigen wherein the AN1/T3 B-cell binds specifically to the selected antigen; and (c) inducing Myc (e.g., recombinant Myc) activity in the AN1/T3 B-cell.

In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is a Myc-ER peptide as described herein. In some embodiments, the Myc peptide is a Myc-GR peptide as described herein.

In some embodiments, a method described herein further comprises recovering the antibody that specifically binds to the selected antigen from a plurality of the AN1/T3 B-cells. In some embodiments, the AN1/T3 B-cell is present in an organism (e.g., a mammal) and inducing of Myc (e.g., recombinant Myc) activity in the AN1/T3 B-cell occurs in vivo. In some embodiments, the contacting the AN1/T3 B-cell with an antigen occurs in vitro or ex vivo.

In some embodiments, a method described herein further comprises introducing (or otherwise providing to) a Myc peptide or a nucleic acid sequence (e.g., a transgenic sequence) encoding the Myc peptide into the AN1/T3 B-cell ex vivo prior to the inducing step. In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is a Myc-ER peptide as described herein. In some embodiments, the Myc peptide is a Myc-GR peptide as described herein.

In some embodiments, a method described herein comprises introducing (or otherwise providing to) the Myc peptide into the AN1/T3 B-cell ex vivo. In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is a Myc-ER peptide as described herein. In some embodiments, the Myc peptide is a Myc-GR peptide as described herein.

In some embodiments, the AN1/T3 B-cell is an anergic B-cell prior to induction of Myc (e.g., recombinant Myc) activity. In some embodiments, the selected antigen is a self-antigen. In some embodiments, the nucleic acid sequence (e.g., a transgenic nucleic acid sequence) encoding the Myc peptide comprises a B-cell specific promoter operably linked to the open reading frame encoding the Myc peptide. In some embodiments, the nucleic acid sequence (e.g., a transgenic nucleic acid sequence) encoding the Myc peptide comprises an inducible promoter operably linked to the open reading frame for the Myc peptide. In some embodiments, the inducible promoter comprises one or more TREs and the recombinant AN1/T3 B-cell further expresses a tTA peptide or an rtTA peptide. In some embodiments, the recombinant AN1/T3 B-cell expresses the tTA peptide.

In some embodiments, the Myc peptide is a Myc-ER fusion peptide. In some embodiments, inducing Myc (e.g., recombinant Myc) activity comprises contacting the recombinant AN1/T3 B-cell with an ER ligand. In some embodiments, the Myc peptide is a Myc-GR fusion peptide. In some embodiments, inducing Myc (e.g., recombinant Myc) activity comprises contacting the recombinant AN1/T3 B-cell with a GR ligand. In some embodiments, the AN1/T3 B-cell is a mouse cell. In some embodiments, contacting the AN1/T3 B-cell with an antigen comprises immunizing an organism with the selected antigen.

In some embodiments, the immunized organism is an organism (e.g., a mammal) carrying the nucleic acid sequence (e.g., a transgenic nucleic acid sequence) encoding the Myc peptide. In some embodiments, the nucleic acid sequence (e.g., a transgenic sequence) is an inducible nucleic acid sequence (e.g., a transgenic sequence). In some embodiments, the inducible nucleic acid sequence (e.g., a transgenic sequence) comprises a promoter, and wherein the promoter comprises one or more TREs. In some embodiments, the organism (e.g., a mammal) further carries and expresses a tTA nucleic acid sequence (e.g., a transgenic sequence) or an rtTA nucleic acid sequence (e.g., a transgenic sequence). In some embodiments, the organism (e.g., a mammal) further carries and expresses a nucleic acid sequence (e.g., a transgenic sequence) encoding the selected antigen.

In some embodiments, provided herein is a method of producing an antibody specific for an antigen, comprising (a) providing an anergic or tolerant B-cell wherein the anergic or tolerant B-cell comprises a nucleic acid sequence (e.g., a transgenic sequence) encoding a Myc peptide, (b) contacting the anergic or tolerant B-cell with an antigen wherein the anergic or tolerant B-cell binds specifically to the selected antigen; and (c) inducing Myc (e.g., recombinant Myc) activity in the anergic or tolerant B-cell.

In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is a Myc-ER peptide as described herein. In some embodiments, the Myc peptide is a Myc-GR peptide as described herein.

In some embodiments, a method described herein further comprises recovering the antibody that specifically binds to the selected antigen from a plurality of the anergic or tolerant B-cells. In some embodiments, the anergic or tolerant B-cell is present in an organism (e.g., a mammal) and inducing of Myc (e.g., recombinant Myc) activity in the anergic or tolerant B-cell occurs in vivo. In some embodiments, the contacting the anergic or tolerant B-cell with an antigen occurs in vitro or ex vivo.

In some embodiments, a method described herein further comprises introducing (or otherwise providing to) a Myc peptide or a nucleic acid sequence (e.g., a transgenic sequence) encoding the Myc peptide into the anergic or tolerant B-cell ex vivo prior to the inducing step. In some embodiments, the Myc peptide is a fusion peptide. In some embodiments, the Myc peptide is a TAT-Myc peptide as described herein.

In some embodiments, a method described herein comprises introducing (or otherwise providing to) the Myc peptide into the anergic or tolerant B-cell ex vivo. In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is a Myc-ER peptide as described herein. In some embodiments, the Myc peptide is a Myc-GR peptide as described herein.

In some embodiments, the anergic or tolerant B-cell is anergic or tolerant to the selected antigen prior to induction of Myc (e.g., recombinant Myc) activity. In some embodiments, the selected antigen is a self-antigen.

In some embodiments, the nucleic acid sequence (e.g., a transgenic nucleic acid sequence) encoding the Myc peptide comprises a B-cell specific promoter operably linked to the open reading frame encoding the Myc peptide. In some embodiments, the nucleic acid sequence (e.g., a transgenic nucleic acid sequence) encoding the Myc peptide comprises an inducible promoter operably linked to the open reading frame for the Myc peptide. In some embodiments, the inducible promoter comprises one or more TREs and the anergic or tolerant B-cell further expresses a tTA peptide or an rtTA peptide. In some embodiments, the anergic or tolerant B-cell expresses the tTA peptide.

In some embodiments, the Myc peptide is a Myc-ER fusion peptide. In some embodiments, inducing Myc (e.g., recombinant Myc) activity comprises contacting the anergic or tolerant B-cell with an ER ligand. In some embodiments, the Myc peptide is a Myc-GR fusion peptide. In some embodiments, inducing Myc (e.g., recombinant Myc) activity comprises contacting the anergic or tolerant B-cell with a GR ligand.

In some embodiments, the anergic or tolerant B-cell is a mouse cell. In some embodiments, contacting the anergic or tolerant B-cell with an antigen comprises administering the selected antigen to an organism (i.e., immunizing or inoculating the organism). In some embodiments, the organism is a xenomouse. In some embodiments, the immunized animal is an organism (e.g., a mammal) carrying the nucleic acid sequence (e.g., a transgenic nucleic acid sequence) encoding the Myc peptide. In some embodiments, the nucleic acid sequence (e.g., a transgenic sequence) is an inducible nucleic acid sequence (e.g., a transgenic sequence). In some embodiments, the inducible nucleic acid sequence (e.g., a transgenic sequence) comprises a promoter, and wherein the promoter comprises one or more TREs. In some embodiments, the organism (e.g., a mammal) further carries and expresses a tTA nucleic acid sequence (e.g., a transgenic sequence) or an rtTA nucleic acid sequence (e.g., a transgenic sequence). In some embodiments, the organism (e.g., a mammal) further carries and expresses a nucleic acid sequence (e.g., a transgenic sequence) encoding the selected antigen.

In some embodiment, the transformation of AN1/T3 populations into B-cell lines that produce antigen specific antibodies of interest occurs in vivo. In some embodiments, a method described herein comprises the use of MMTV-tTA/TRE-Myc organisms. In some embodiments, a method described herein comprises the use of Eu-Myc, Myc-GR, or Myc-ER organisms. In some embodiments, any organism is used in which the organism over-expresses Myc. In some embodiments, over-expression of MYC is induced by contacting the cell with a small molecule, a biologic, a peptide, an antibody, or a combination thereof. In some embodiments, the small molecule is an antagonist of Max-1, Mxi-1, MAD, or a combination thereof. In some embodiments, the small molecule is an antagonist of Max-1. In some embodiments, the small molecule is an antagonist of Mxi-1. In some embodiments, the small molecule is an antagonist of MAD. In some embodiments, over-expression of MYC is induced by contacting the cell with a siRNA molecule for Max-1, Mxi-1, MAD, or a combination thereof. In some embodiments, a method described herein comprises the use of any organism in which Myc (e.g., recombinant Myc) activity is inducible. In some embodiments, a method described herein comprises the use of any mouse in which Myc (e.g., recombinant Myc) activity is present or is inducible. In some embodiments, the organisms that over-express MYC are mice. In some embodiments, the organism is a xenomouse. In some embodiments, the organisms are exposed to the selected antigen and the organisms are maintained under condition in which MYC is over-expressed. In some embodiments, a method described herein comprises organisms that express the selected antigen by means of an integrated nucleic acid sequence (e.g., a transgenic sequence). In some embodiments, tolerance to an antigen is broken by over-expression of MYC in vivo. In some embodiments, B-cell tolerance to an antigen is broken by Myc (e.g., recombinant Myc) activity in an AN1-T3 cell that binds the selected antigen. In some embodiments, tolerance is broken by inducing Myc (e.g., recombinant Myc) activity in an anergic B-cell in vivo. In some embodiments, over-expression of MYC in vivo results in the expansion of populations of B-cells, once anergic, that produce antibodies to the selected antigen. In some embodiments, MYC is over-expressed at 3 weeks of age or later to induce proliferation of antigen-specific B-cells. In some embodiments, MYC is over-expressed from 3-30 weeks of age. In some embodiments, MYC is over-expressed from 3-6, 3-12, or 3-24 weeks of age. In some embodiments, MYC is over-expressed at 6 weeks of age. In some embodiments, Myc is expressed at any point in the life cycle of the organism that provides for the generation of antigen-specific B-cells as described herein.

In some embodiments, MMTV-tTA/TRE-MYC mice exposed to antigen are maintained on a doxycycline containing diet since conception. These mice are later switched to normal mouse chow to induce the over-expression of MYC. In some embodiments, doxycycline is withdrawn from the diet at 3-30 weeks of age. In some embodiments, doxycycline is withdrawn from the diet from 3-6, 3-12, or 3-24 weeks of age. In some embodiments, doxycycline is withdrawn from the diet at 6 weeks of age. In some embodiments, doxycycline is withdrawn from the diet at any point in the life cycle of the organism that provides for the generation of antigen-specific B-cells as described herein. The organisms are examined daily for clinical signs associated with the development of B-cell lymphomas. In some embodiments, mice that develop B-cell lymphomas present with scruffy fur, externally evident lymphadenopathy, dehydration, sluggishness, hind limb paralysis—ascending, etc. Once tumors develop, leukocytes are isolated from the resulting tumors or from lymph nodes, spleen, bone marrow, or blood. In some embodiments, leukocytes are isolated prior to the development of tumors. In some embodiments, antigen-specific B-cells that over-express MYC are recovered from the isolated leukocytes. In some embodiments, the recovered antigen-specific B-cells are expanded in vitro. In some embodiments, antigen specific antibody to antigens if recovered from the selected antigen-specific B-cells that are genetically altered to express Myc. In some embodiments, monoclonal cell lines are generated from the recovered antigen-specific B-cells. In some embodiments, monoclonal antibodies are recovered from the selected antigen-specific B-cells. In some embodiments, the cells (e.g., mammalian cells) are stored frozen for future access to viable, primary antibody producing cells. In some embodiments, antibodies are isolated directly from organisms that present with B-cell lymphomas.

In some embodiments, provided herein is a method of producing an antibody specific for an antigen, comprising (a) providing an anergic or tolerant B-cell, wherein the anergic or tolerant B-cell comprises a nucleic acid sequence (e.g., a transgenic sequence) encoding a Myc peptide, (b) contacting the anergic or tolerant B-cell with an antigen in vivo wherein the anergic or tolerant B-cell binds specifically to the selected antigen; and (c) inducing Myc (e.g., recombinant Myc) activity in the anergic or tolerant B-cell.

In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is a Myc-ER peptide as described herein. In some embodiments, the Myc peptide is a Myc-GR peptide as described herein.

In some embodiments, the anergic or tolerant B-cells, upon exposure to antigen and Myc (e.g., recombinant Myc) activity, are transformed into immortal B-cells that produce an antibody that specifically binds to the selected antigen. In some embodiments, the anergic or tolerant B-cells, upon exposure to antigen and Myc (e.g., recombinant Myc) activity, are transformed into immortal B-cells that produce an antibody that specifically binds to the selected antigen and cell fusion is not required.

In some embodiments, a method described herein further comprises recovering the antibody that specifically binds to the selected antigen from a plurality of the immortal B-cells that produce an antibody that specifically binds to the selected antigen. In some embodiments, the anergic or tolerant B-cell is present in an organism (e.g., a mammal) and inducing of Myc (e.g., recombinant Myc) activity in the anergic or tolerant B-cell occurs in vivo.

In some embodiments, a method described herein further comprises introducing (or otherwise providing to) a Myc peptide or a nucleic acid sequence (e.g., a transgenic sequence) encoding the Myc peptide into the anergic or tolerant B-cell ex vivo prior to the inducing step. In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is a Myc-ER peptide as described herein. In some embodiments, the Myc peptide is a Myc-GR peptide as described herein.

In some embodiments, a method described herein comprises introducing (or otherwise providing to) the Myc peptide (e.g., a recombinant Myc peptide (e.g., a Myc fusion peptide as described herein)) into the anergic or tolerant B-cell ex vivo. In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is a Myc-ER peptide as described herein. In some embodiments, the Myc peptide is a Myc-GR peptide as described herein.

In some embodiments, the anergic or tolerant B-cell is anergic or tolerant to the selected antigen prior to induction of Myc (e.g., recombinant Myc) activity. In some embodiments, the selected antigen is a self-antigen. In some embodiments, the nucleic acid sequence (e.g., a transgenic nucleic acid sequence) encoding the Myc peptide comprises a B-cell specific promoter operably linked to the open reading frame encoding the Myc peptide. In some embodiments, the nucleic acid sequence (e.g., a transgenic nucleic acid sequence) encoding the Myc peptide comprises an inducible promoter operably linked to the open reading frame for the Myc peptide. In some embodiments, the inducible promoter comprises one or more TREs and the recombinant anergic or tolerant B-cell further expresses a tTA peptide or an rtTA peptide. In some embodiments, the recombinant anergic or tolerant B-cell expresses the tTA peptide.

In some embodiments, the Myc peptide is a Myc-ER fusion peptide. In some embodiments, inducing Myc (e.g., recombinant Myc) activity comprises contacting the recombinant anergic or tolerant B-cell with an ER ligand. In some embodiments, the Myc peptide is a Myc-GR fusion peptide. In some embodiments, inducing Myc (e.g., recombinant Myc) activity comprises contacting the recombinant anergic or tolerant B-cell with a GR ligand. In some embodiments, the anergic or tolerant B-cell is a mouse cell. In some embodiments, contacting the anergic or tolerant B-cell with an antigen comprises immunizing an organism with the selected antigen. In some embodiments, the organism is a xenomouse. In some embodiments, the immunized animal is an organism (e.g., a mammal) carrying the nucleic acid sequence (e.g., a transgenic nucleic acid sequence) encoding the Myc peptide. In some embodiments, the nucleic acid sequence (e.g., a transgenic sequence) is an inducible nucleic acid sequence (e.g., a transgenic sequence). In some embodiments, the inducible nucleic acid sequence (e.g., a transgenic sequence) comprises a promoter, and wherein the promoter comprises one or more TREs. In some embodiments, the organism (e.g., a mammal) further carries and expresses a tTA nucleic acid sequence (e.g., a transgenic sequence) or an rtTA nucleic acid sequence (e.g., a transgenic sequence). In some embodiments, the organism (e.g., a mammal) further carries and expresses a nucleic acid sequence (e.g., a transgenic sequence) encoding the selected antigen.

In some embodiments, provided herein is a method of producing an antibody specific for an antigen, comprising (a) providing a CD79 positive cell, wherein the CD79 positive cell comprises a nucleic acid sequence (e.g., a transgenic sequence) encoding a Myc peptide, (b) contacting the CD79 positive cell with an antigen wherein the CD79 positive cell binds specifically to the selected antigen; and (c) inducing Myc (e.g., recombinant Myc) activity in the CD79 positive cell.

In some embodiments, the CD79 positive cell, upon exposure to antigen and Myc (e.g., recombinant Myc) activity, is transformed into an immortal CD79 positive cell that produce antibody that specifically binds to the selected antigen. In some embodiments, the CD79 positive cells, upon exposure to antigen and Myc (e.g., recombinant Myc) activity, are transformed into immortal B-cells that produce antibody that specifically binds to the selected antigen and cell fusion is not required. In some embodiments, a method described herein further comprises recovering the antibody that specifically binds to the selected antigen from a plurality of the immortal CD79 positive cells that produce antibody that specifically binds to the selected antigen.

In some embodiments, the CD79 positive cell is present in an organism (e.g., a mammal) and induction of Myc (e.g., recombinant Myc) activity in the CD79 positive cell occurs in vivo. In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is a Myc-ER peptide as described herein. In some embodiments, the Myc peptide is a Myc-GR peptide as described herein.

In some embodiments, a method described herein further comprises introducing (or otherwise providing to) a Myc peptide or a nucleic acid sequence (e.g., a transgenic sequence) encoding the Myc peptide into the CD79 positive cell ex vivo prior to the inducing step. In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is a Myc-ER peptide as described herein. In some embodiments, the Myc peptide is a Myc-GR peptide as described herein.

In some embodiments, a method described herein comprises introducing (or otherwise providing to) the Myc peptide (e.g., a recombinant Myc peptide (e.g., a Myc fusion peptide as described herein)) into the CD79 positive cell ex vivo. In some embodiments, the Myc peptide is a fusion peptide. In some embodiments, the Myc peptide comprises a PTD. In some embodiments, the Myc peptide is a TAT-Myc peptide as described herein. In some embodiments, the Myc peptide is a Myc-ER peptide as described herein. In some embodiments, the Myc peptide is a Myc-GR peptide as described herein.

In some embodiments, the Myc peptide comprises a protein transduction domain. In some embodiments, the CD79 positive cell is anergic or tolerant to the selected antigen prior to induction of Myc (e.g., recombinant Myc) activity. In some embodiments, the selected antigen is a self-antigen. In some embodiments, the nucleic acid sequence (e.g., a transgenic nucleic acid sequence) encoding the Myc peptide comprises a B-cell specific promoter operably linked to the open reading frame encoding the Myc peptide. In some embodiments, the nucleic acid sequence (e.g., a transgenic nucleic acid sequence) encoding the Myc peptide comprises an inducible promoter operably linked to the open reading frame for the Myc peptide. In some embodiments, the inducible promoter comprises one or more TREs and the recombinant CD79 positive cell further expresses a tTA peptide or an rtTA peptide. In some embodiments, the recombinant CD79 positive cell expresses the tTA peptide.

In some embodiments, the Myc peptide is a Myc-ER fusion peptide. In some embodiments, inducing Myc (e.g., recombinant Myc) activity comprises contacting the recombinant CD79 positive cell with an ER ligand. In some embodiments, the Myc peptide is a Myc-GR fusion peptide. In some embodiments, inducing Myc (e.g., recombinant Myc) activity comprises contacting the recombinant CD79 positive cell with a GR ligand. In some embodiments, the CD79 positive cell is a mouse cell. In some embodiments, contacting the CD79 positive cell with an antigen comprises immunizing an organism with the selected antigen. In some embodiments, the organism is a xenomouse. In some embodiments, the immunized animal is an organism (e.g., a mammal) carrying the nucleic acid sequence (e.g., a transgenic nucleic acid sequence) encoding the Myc peptide. In some embodiments, the nucleic acid sequence (e.g., a transgenic sequence) is an inducible nucleic acid sequence (e.g., a transgenic sequence). In some embodiments, the inducible nucleic acid sequence (e.g., a transgenic sequence) comprises a promoter, and wherein the promoter comprises one or more TREs. In some embodiments, the organism (e.g., a mammal) further carries and expresses a tTA nucleic acid sequence (e.g., a transgenic sequence) or an rtTA nucleic acid sequence (e.g., a transgenic sequence). In some embodiments, the organism (e.g., a mammal) further carries and expresses a nucleic acid sequence (e.g., a transgenic sequence) encoding the selected antigen.

In some embodiments, immortal antibody producing cells are obtained from any animal capable of generating B-cells, including but not limited to humans, non-human primates, mice, rats, chickens, rabbits, pigs, cows or sheep.

In some embodiments, the antibody producing cells (e.g., animal B-cells) that are generated are immortal and/or malignant. Hybridomas that result from the cell (e.g., a mammalian cell) fusion of a B-cell and a myeloma partner are typically heterokaryons and comprise two or more separate nuclei. In some embodiments, antibody producing cells (e.g., B-cells) have one nucleus. Hybridomas that result from the cell (e.g., a mammalian cell) fusion of a B-cell and a myeloma partner contain an increased number of chromosomes that often equals the sum of the number of chromosomes present in each of the parent donor cells. Over time and over multiple cell passages, a hybridoma often loses some chromosomes but generally retains more chromosomes than were present in any one of the donor parent cells. In some embodiments, the antibody producing cells (e.g., B-cells), that are generated by any of the methods described herein, display the same number of chromosomes as were present before Myc was overexpressed. In some embodiments, the antibody producing cells that are generated by the methods described herein comprise no more than 5 additional chromosomes when compared to a time just prior to antibody production. In some embodiments, the antibody producing cells that are generated by the methods described herein comprise no more than 4 additional chromosomes when compared to a time just prior to antibody production. In some embodiments, the antibody producing cells that are generated by the methods described herein comprise no more than 3 additional chromosomes when compared to a time just prior to antibody production. In some embodiments, the antibody producing cells that are generated by the methods described herein comprise no more than 2 additional chromosomes when compared to a time just prior to antibody production. In some embodiments, the antibody producing cells that are generated by the methods described herein comprise no more than 1 additional chromosome when compared to a time just prior to antibody production. In some embodiments, the antibody producing cells that are generated by the methods described herein comprise no additional chromosomes when compared to a time just prior to antibody production.

In some embodiments, reactive splenic B-cells are cultured in the presence of an onco-peptide (e.g., Myc). In some embodiments, reactive splenic B-cells are cultured in the presence of a Myc peptide. In some embodiments, reactive splenic B-cells are cultured in the presence of a TAT-Myc fusion peptide disclosed herein. In some embodiments, culturing reactive splenic B-cells in the presence of a TAT-Myc fusion peptide facilitates the fusion of the B-cell and a myeloma fusion partner. In some embodiments, culturing reactive splenic B-cells in the presence of a TAT-Myc fusion peptide ameliorates the need for using reactive B-cells in S-phase when fusing a B-cell with a myeloma fusion partner.

TAT-MYC Fusion Peptide

Disclosed herein, in certain embodiments, is a fusion peptide comprising (a) a transporter peptide sequence; and (b) a MYC sequence. In some embodiments, the fusion peptide is a peptide of Formula (I):

transporter peptide sequence-MYC sequence.

In some embodiments, a fusion peptide disclosed herein comprises (a) a transporter peptide sequence; (b) a MYC sequence; and (c) one or more molecules that link the transporter peptide sequence and the MYC sequence. In some embodiments, the fusion peptide is a peptide of Formula (II):

transporter peptide sequence-X-MYC sequence, wherein -X- is molecule that links the transporter peptide sequence and the MYC sequence. In some embodiments, -X- is an amino acid. In some embodiments, -X- is at least one amino acid.

In some embodiments, a fusion peptide disclosed herein comprises (a) TAT, and (b) c-MYC. In some embodiments, a fusion peptide disclosed herein comprises (a) TAT$_{[48-57]}$, and (b) c-MYC. In some embodiments, a fusion peptide disclosed herein comprises (a) TAT$_{[57-48]}$, and (b) c-MYC.

In some embodiments, a fusion peptide disclosed herein comprises (a) TAT, (b) a linker amino acid, and (c) c-MYC. In some embodiments, a fusion peptide disclosed herein comprises (a) TAT$_{[48-57]}$, (b) a linker amino acid, and (c) c-MYC. In some embodiments, a fusion peptide disclosed herein comprises (a) TAT$_{[57-48]}$, (b) a linker amino acid, and (c) c-MYC.

In some embodiments, a fusion peptide disclosed herein further comprises at least one amino acid sequence that facilitates purification of the fusion protein. In some embodiments, a fusion peptide disclosed herein comprises a protein tag. In some embodiments, a fusion peptide disclosed herein comprises a polyhistidine tag. In some embodiments, a fusion peptide disclosed herein comprises an epitope tag. In some embodiments, a fusion peptide disclosed herein comprises at least one of a polyhistidine tag and an epitope tag. In some embodiments, a fusion peptide disclosed herein comprises at least one of a 6-histidine tag (SEQ ID NO. 2) and a V5 epitope tag.

In some embodiments, the histidine tag is a 6-histidine tag (SEQ ID NO. 2). In some embodiments, the histidine tag comprises the sequence HHHHHH (SEQ ID NO. 2). In some embodiments, a polyHis tag is added to a fusion protein disclosed herein by any suitable method. In some embodiments, a TAT-MYC peptide sequence is cloned into an expression vector encoding a polyHis-tag. In some embodiments, a polyHis tag is added by PCR (i.e., the PCR primers comprise a polyHis sequence).

In some embodiments, a fusion peptide disclosed herein further comprises at least one protein tag. In some embodiments, a fusion peptide disclosed herein comprises an epitope tag. In some embodiments, a fusion peptide disclosed herein further comprises a V5 epitope tag. In some embodiments, the V5 tag comprises the amino acids: GKPIPNPLLGLDST (SEQ ID NO. 3). In some embodiments, the V5 tag comprises the amino acids: IPNPLLGLD (SEQ ID NO. 4). In some embodiments, a V5 tag is added to a fusion protein disclosed herein by any suitable method. In some embodiments, a TAT-MYC peptide sequence is cloned into an expression vector encoding a V5 tag. In some embodiments, a V5 tag is added by PCR (i.e., the PCR primers comprise a V5 sequence).

In some embodiments, the amino acids are in the D formation. In some embodiments, the amino acids are in the L formation. In some embodiments, a first plurality of amino acids are in the D formation and a second plurality are in the L formation.

In some embodiments, the MYC Increasing Agent comprises:

```
                                                  (SEQ ID NO. 5)
MRKKRRQRRRMDFFRVVENQQPPATMPLNVSFTNRNYDLDYDSVQPYFYC

DEEENFYQQQQQSELQPPAPSEDIWKKFELLPTPPLSPSRRSGLCSPSYV

AVTPFSLRGDNDGGGGSFSTADQLEMVTELLGGDMVNQSFICDPDDETFI

KNIIIQDCMWSGFSAAAKLVSEKLASYQAARKDSGSPNPARGHSVCSTSS

LYLQDLSAAASECIDPSVVFPYPLNDSSSPKSCASQDSSAFSPSSDSLLS

STESSPQGSPEPLVLHEETPPTTSSDSEEEQEDEEEIDVVSVEKRQAPGK

RSESGSPSAGGHSKPPHSPLVLKRCHVSTHQHNYAAPPSTRKDYPAAKRV

KLDSVRVLRQISNNRKCTSPRSSDTEENVKRRTHNVLERQRRNELKRSFF

ALRDQIPELENNEKAPKVVILKKATAYILSVQAEEQKLISEEDLLRKRRE

QLKHKLEQLRKGELNSKLEGKPIPNPLLGLDSTRTGHHHHHH
```

Construction of a TAT-MYC Peptide

In some embodiments, a TAT-MYC fusion peptide disclosed herein is constructed by any suitable method. In some embodiments, a nucleotide sequence encoding a TAT-MYC fusion peptide is generated by PCR. In some embodiments, a forward primer for a human MYC sequence comprises an in frame N-terminal 9-amino-acid sequence of the TAT protein transduction domain (i.e., RKKRRQRRR; (SEQ ID NO. 6)). In some embodiments, a reverse primer for a human MYC sequence is designed to remove the stop codon. In some embodiments, the PCR product is cloned into any suitable expression vector (hereinafter, p-TAT-MYC). In some embodiments, the expression vector comprises a polyhistidine tag and a V5 tag.

Recombinant Polypeptides

Described herein are certain recombinant polypeptides. In certain instances, antibodies comprise light and a heavy polypeptide chains. In some embodiments, DNA sequences that encode the light and the heavy chains of the antibody are made, either simultaneously or separately, using reverse transcriptase and DNA polymerase in accordance with suitable methods. In some embodiments, PCR is initiated by consensus constant region primers or by more specific primers based on the published heavy and light chain DNA and amino acid sequences. As discussed above, in some embodiments, PCR is also used to isolate DNA clones encoding the antibody light and heavy chains. In some embodiments, the libraries are screened by consensus primers or larger homologous probes, such as mouse constant region probes.

In some embodiments, DNA, e.g., plasmid DNA, is isolated from the cell (e.g., a mammalian cell) by any suitable method, restriction mapped and sequenced in accordance with any suitable techniques set forth in detail, e.g., in the foregoing references relating to recombinant DNA techniques. In some embodiments, the DNA is synthetic at any point during the isolation process or subsequent analysis.

In some embodiments, following manipulation of the isolated genetic material to provide antibodies, or antigen-binding fragments, variants, or derivatives thereof, the polynucleotides encoding the antibodies are inserted in an expression vector for introduction into host cells which are therein used to produce the desired quantity of antibody.

In certain embodiments, recombinant expression of an antibody, or fragment, derivative or analog thereof, e.g., a heavy or light chain of an antibody that binds to a target molecule utilizes construction of an expression vector containing a nucleic acid that encodes the antibody. Once a polynucleotide encoding an antibody molecule or a heavy or light chain of an antibody, or portion thereof (preferably containing the heavy or light chain variable domain), is obtained, the vector for the production of the antibody molecule is in some embodiments, produced by recombinant DNA technology using any suitable techniques. Thus, processes for preparing a protein by expressing a polynucleotide containing an antibody encoding nucleotide sequence are described herein. In some embodiments, processes any suitable manner of construct expression vectors containing antibody coding sequences comprising appropriate transcriptional and translational control signals is utilized in the a method disclosed herein. These processes include, for example, in vitro recombinant DNA techniques, synthetic techniques, and in vivo genetic recombination. Thus, in some embodiments, provided herein are replicable vectors comprising a nucleotide sequence encoding an antibody molecule, or a heavy or light chain thereof, or a heavy or light chain variable domain, operably linked to a promoter. In some embodiments, vectors comprise the nucleotide sequence encoding the constant region of the antibody and the variable domain of the antibody is incorporated into the vector for expression of the entire heavy or light chain.

In some embodiments, the cloned variable region genes are inserted into an expression vector along with the heavy and light chain constant region genes synthesized as discussed above. In some embodiments, an expression vector that is capable of eliciting expression in eukaryotic cells is used. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In certain instances, screening large numbers of transformed cells for those that express suitably high levels of immunoglobulin heavy and light chains is accomplished by any suitable method, for example, by robotic systems.

In some embodiments, once the vector or DNA sequence encoding an antibody is prepared, the expression vector is introduced into an appropriate host cell as disclosed herein. Introduction of the plasmid into the host cell is accomplished by any suitable method. These include, but are not limited to, transfection (including electroporation), protoplast fusion, calcium phosphate precipitation, cell fusion with enveloped DNA, DEAE-dextran mediated transfection, microinjection, cationic lipid-mediated transfection, transduction, scrape loading, ballistic introduction and infection with intact virus. See, e.g., Ridgway (1988) "Mammalian Expression Vectors" in Vectors, ed. Rodriguez and Denhardt (Butterworths, Boston, Mass.), Chapter 24.2, pp. 470-472; Sambrook et al. (1989) *Molecular Cloning: A Laboratory Manual,* 2nd Ed., Cold Spring Harbor Laboratory Press, Cold Spring Harbor, N.Y. In certain instances, host cells harboring the expression construct are grown under conditions appropriate to the production of the light chains and heavy chains, and assayed for heavy and/or light chain protein synthesis. Exemplary assay techniques include ELISA, radioimmunoassay (RIA), or fluorescence-activated cell sorter analysis (FACS), immunohistochemistry and the like.

As disclosed herein, introducing (or otherwise providing to) nucleic acids and/or vectors into host organisms are achieved by any suitable method. Examples of such processes include but are not limited to gene gun techniques, naked DNA immunization, the development of transgenic or transchromosomal organisms, lentiviral mediated production of transgenic organisms, vaccinia viruses transduction and adenovirus.

As disclosed herein, introducing (or otherwise providing to) antigens into organisms or cells comprises any manner suitable. Some examples of such processes include but are not limited to the use of Tat fusion peptides, various immunization protocols, infection by virus, and introduction of whole cells expressing antigen.

In some embodiments, an expression vector is transferred to a host cell by any suitable method, and the transfected cells are then cultured by conventional techniques or techniques disclosed herein to produce an antibody for use in the methods described herein. Thus, provided in certain embodiments, herein are host cells that contain a polynucleotide encoding an antibody, or a heavy or light chain thereof, operably linked to a heterologous promoter. In some embodiments, for the expression of double-chained antibodies, vectors encoding both the heavy and light chains are used to express of the entire immunoglobulin molecule.

In some embodiments, a number of selection systems are used including, but not limited to, the herpes simplex virus thymidine kinase (Wigler et al. (1977) *Cell* 11:223), hypoxanthine-guanine phosphoribosyltransferase (Szybalska and Szybalski (1992) *Proc. Natl. Acad. Sci. USA* 48:202), and adenine phosphoribosyltransferase (Lowy et al. (1980) Cell 22:817) genes employed in tk-, hgprt- or aprt-cells, respectively. Also, in some embodiments, antimetabolite resistance is used as the basis of selection for the following genes: dhfr, which confers resistance to methotrexate (Wigler et al. (1980) *Natl. Acad. Sci. USA* 77:357; O'Hare et al. (1981) *Proc. Natl. Acad. Sci. USA* 78:1527); gpt, which confers resistance to mycophenolic acid (Mulligan and Berg (1981) *Proc. Natl Acad. Sci. USA* 78:2072); neo, which confers resistance to the aminoglycoside G-418 Clinical Pharmacy 12:488-505; Wu and Wu (1991) *Biotherapy* 3:87-95; Tolstoshev (1993) *Ann. Rev. Pharmacol. Toxicol.* 32:573-596; Mulligan (1993) *Science* 260:926-932; and Morgan and Anderson (1993) *Ann. Rev. Biochem.* 62:191-217 (1993); *TIB TECH* 11(5):155-215 (May, 1993); and hygro, which confers resistance to hygromycin (Santerre et al. (1984) *Gene* 30:147. In some embodiments, methods commonly known in the art of recombinant DNA technology which are used as described in Ausubel et al. (1993) *Current Protocols in Molecular Biology* (John Wiley & Sons, N.Y.); Kriegler (1990) "Gene Transfer and Expression" in A Laboratory Manual (Stockton Press, N.Y.); Dracopoli et al. (eds) (1994) *Current Protocols in Human Genetics* (John Wiley & Sons, N.Y.) Chapters 12 and 13; Colberre-Garapin et al. (1981) *J. Mol. Biol.* 150:1.

In some embodiments, the expression level of an antibody molecule is increased by vector amplification (for a review, see Bebbington and Hentschel (1987) "The Use of Vectors Based on Gene Amplification for the Expression of Cloned Genes in Mammalian Cells in DNA Cloning" (Academic Press, N.Y.) Vol. 3. When a marker in the vector system expressing antibody is amplifiable, an increase in the level of inhibitor present in the culture of the host cell will increase the number of copies of the marker gene. Since the amplified region is associated with the antibody gene, production of the antibody will also increase (Crouse et al. (1983) *Mol. Cell. Biol.* 3:257).

Harvesting Antibodies

In various embodiments, of any of the methods disclosed herein, antibodies that specifically binds to the selected antigen, as well as the cell (e.g., a mammalian cell) producing such antibodies, are isolated (i.e., harvested) directly from the tissues (spleen, lymph nodes, blood, etc.) or serum of an organism (e.g., mouse, rabbit). In some embodiments, the antibodies are isolated from splenic tissue. In some embodiments, the antibodies are harvested from lymph nodes. In some embodiments, the antibodies are harvested from blood. In some embodiments, the tissue is harvested by any suitable method.

In some embodiments, the antibodies are harvested in the presence of the selected antigen. In some embodiments, the antibodies are harvested in the presence of an onco-peptide (e.g., Myc, TAT-Myc). In some embodiments, the antibodies are harvested in the presence of an onco-peptide (e.g., Myc, TAT-Myc) and the selected antigen. In some embodiments, the antibodies are harvested in the presence of a Myc peptide. In some embodiments, the antibodies are harvested in the presence of a TAT-Myc fusion peptide disclosed herein.

In some embodiments, harvesting antibodies in the presence of the selected antigen, the selected antigen and an onco-peptide, the selected antigen and Myc, or the selected antigen and TAT-Myc reduces the concentration of tolerant and/or anergic cells. In some embodiments, harvesting antibodies in the presence of the selected antigen and TAT-Myc reduces the concentration of tolerant and/or anergic cells (e.g., B-cells).

Scale Up

In some embodiments, antibodies produced by a method disclosed herein are reengineered for large scale production. In some embodiments, antibodies produced by a method disclosed herein are reengineered for large scale production for clinical use or for use in a diagnostic assay, e.g., under GMP or cGMP guidelines. In some embodiments, a selected antibody is prepared by:
a. recovering a nucleic acid encoding the antibody from cell (e.g., a B-cell) that comprises a nucleic acid sequence (e.g., a transgenic sequence) encoding an onco-peptide (e.g., recombinant onco-peptide; e.g., Myc) and/or a recombinant onco-peptide (e.g., recombinant onco-peptide; e.g., Myc);
b. introducing (or otherwise providing to) the nucleic acid encoding the antibody into a cell that is suitable for large scale production of an antibody.

In some embodiments, cell that is genetically altered to express an onco-peptide and comprises a nucleic acid encoding the antibody is prepared according to any process described herein. In certain embodiments, the method further comprises selecting an antibody. In some embodiments, the antibody is a human antibody. In certain embodiments, cell expresses human antibodies. In certain embodiments, the method further comprises contacting cell (e.g., B-cell) that comprises a nucleic acid sequence (e.g., a transgenic sequence) encoding an onco-peptide (e.g., recombinant onco-peptide; e.g., Myc) with a selected antibody.

In some embodiments, the method further comprises culturing the cell (e.g., a mammalian cell) that is suitable for large scale production of an antibody under conditions suitable for production of the antibody. In certain embodiments, the method further comprises recovering a quantity of the antibody, e.g., at least 0.1 kg, at least 0.5 kg, at least 1 kg, at least 10 kg, or at least 100 kg.

Any suitable cell line for large scale production is used in such processes. Examples of cells or cell lines that are suitable for large scale production include, but are not limited to, Chinese hamster ovary CHO, NSO, BSC-1 cells, LLC-MK cells, CV-1, HeLa, HEK293, VERO, MDBK, MDCK, MDOK, CRFK, RAF, TCMK, LLC-PK, PK15, WI-38, MRC-5, T-FLY, BHK, BRL 3A, HepG2, HT1080 or derivatives thereof.

In some embodiments, nucleic acids encoding an antibody, produced by the methods described herein, are recovered from a B-cell that is genetically altered to express Myc and are reintroduced into a CHO cell or derivatives thereof (including dhfr—CHO cells used with a DHFR selectable marker), for the purpose of large scale production of the antibody. In some embodiments, nucleic acids encoding the antibody of interest are recovered from a B-cell that is genetically altered to express Myc and are reintroduced into a plant cell that is suitable for large scale production of an antibody. In some embodiments, nucleic acids encoding an antibody, produced by the methods described herein, are recovered from a B-cell that is genetically altered to express Myc and are reintroduced into a plant, part of a plant or a plant seed that is suitable for large scale production of an antibody. In some embodiments, nucleic acids encoding an antibody, produced by the methods described herein, are recovered from a B-cell that is genetically altered to express Myc and are reintroduced into cotton, potato, soybean, corn, maize, tobacco, soybean, alfalfa, or rice for the purpose of large scale production of the antibody. In some embodiments, nucleic acids encoding an antibody, produced by the methods described herein, are recovered from a B-cell that is genetically altered to express Myc and are reintroduced into a yeast for the purpose of large scale production of the antibody. Urlaub and Chasin, (1980) Proc. Natl. Acad. Sci. USA 77:4216-4220 and R. J. Kaufman and P. A. Sharp (1982) Mol. Biol. 159:601-621.

In vitro production allows scale-up to give large amounts of the desired polypeptides. Techniques for cell (e.g., a mammalian cell) cultivation under tissue culture conditions include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, in some embodiments, solutions of polypeptides are purified in any manner suitable. Examples of such methods include but are not limited to chromatography methods, for example gel filtration, ion-exchange chromatography, chromatography over DEAE-cellulose or (immuno-)affinity chromatography.

Once an antibody molecule is recombinantly expressed, in some embodiments, the antibody is purified by any suitable method for purification of an immunoglobulin molecule, for example, by chromatography (e.g., ion exchange, affinity, protein A affinity, protein G affinity, gel filtration and sizing column chromatography), centrifugation, differential solubility, or by any other standard technique for the purification of antibodies. In some embodiments, isolated antibodies include serum containing such antibodies, or antibodies that have been purified to varying degrees.

Antigens

In some embodiments, the methods disclosed herein are used to generate antibodies that bind and/or are specific to antigens. In some embodiments, the selected antigens are therapeutic targets. In some embodiments, the antibodies are generated to bind an antigen wherein the selected antigen is a TNF or TNF receptor family member or TNF like molecule. In some embodiments, the TNF or TNF receptor family member or TNF like molecule is selected from the list: TNF-alpha, lymphotoxin (LT), LT-alpha (also known as TNF-beta), LT-beta (found in complex heterotrimers with LT-alpha), OPGL, FasL, CD27L, CD30L, CD40L, 4-1BBL, DcR3, OX40, OX40L, TNF-gamma (International Publication No. WO 96/14328), TRAIL, AIM-II (International Publication No. WO 97/34911), APRIL (J. Exp. Med. 188(6):1185-1190), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-1BB, TR2 (International Publication No. WO 96/34095), DR3 (International Publication No. WO 97/35904), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, LIGHT, TRANCE, TACI, BAFFR, BCMA, NGFR, APRIL, CD154, CD70, CD153 including all soluble and membrane bound forms of these molecules. In some embodiments, the antibodies are generated to bind an antigen wherein the selected antigen is any cytokine or interleukin. In some embodiments, the cytokine or interleukin antigen is selected from the list: IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IFN-alpha, IFN-beta, IFN-gamma, MIF, GM-CSF, and G-CSF. In some embodiments, the antibodies are generated to bind an antigen wherein the selected antigen is chemokine or chemokine receptor. In some embodiments, the chemokine antigen is selected from the list: gamma-interferon inducible protein-10 (γIP-10), interleukin-8 (IL-8), platelet factor-4 (PF4), neutrophil activating protein (NAP-2), GRO-α, GRO-β, GRO-γ, neutrophil-activating peptide (ENA-78), granulocyte chemoattractant protein-2 (GCP-2), and stromal cell-derived factor-1 (SDF-1, or pre-B cell stimulatory factor (PBSF)); and/or a β(CC) chemokine selected from the group consisting of: RANTES (regulated on activation, normal T expressed and secreted), macrophage inflammatory protein-1 alpha (MIP-1α), macrophage inflammatory protein-1 beta (MIP-1β), monocyte chemotactic protein-1 (MCP-1), monocyte chemotactic protein-2 (MCP-2), monocyte chemotactic protein-3 (MCP-3), monocyte chemotactic protein-4 (MCP-4) macrophage inflammatory protein-1 gamma (MIP-1γ), macrophage inflammatory protein-3 alpha (MIP-3α), macrophage inflammatory protein-3 beta (MIP-3β), macrophage inflammatory protein-4 (MIP-4/DC-CK-1/PARC), eotaxin, Exodus, and I-309; and/or the γ(C) chemokine, and lymphotactin. In some embodiment the selected antigen is a chemokine receptor. In some embodiments, the chemokine ligand is selected from the list comprising CCL1, CCL2, CCL3, CCL4, CCL5, CCL6, CCL7, CCL8, CCL9, CCL10, CCL11, CCL12, CCL13, CCL2, CCL14, CCL15, CCL16, CCL17, CCL18, CCL19, CCL20, CCL21, CCL22, CCL23, CCL24, CCL25, CCL26, CCL27 and CCL28. In some embodiments, the selected antigen is a chemokine receptor selected from the list: CXCR1, CXCR2, CXCR3, CXCR4, CXCR5, CXCR6, CXCR7, CCR1, CCR2, CCR3, CCR4, CCR5, CCR6, CCR7, CCR8, CCR9, CCR10, and CCR11. In some embodiments, the selected antigen is a fibroblast growth factor. In some embodiments, the fibroblast growth factor is selected from the list: FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15. In some embodiments, the selected antigen is a cell-surface protein. In some embodiments, the cell (e.g., a mammalian cell)-surface protein is a human leukocyte differentiation antigen. In some embodiments, the human leukocyte differentiation antigen is selected from the list: CD1, CD2, CD3, CD4, CD8, CD10, CD20, CD100, CD280, CD281, CD282, CD283, CD284, and CD289. In some embodiments, the human leukocyte differentiation antigen is selected from the list comprising CD1 though CD300. In some embodiments, the selected antigen is an intracellular cancer biomarker. In some embodiments, the selected antigen is encoded by HIV. In some embodiments, the selected antigen is a polypeptide comprising all or a portion of an HIV encoded polypeptide selected from the list: Gag, pol, protease (prot), reverse transcriptase, integrase, RNAseH, Tat, Rev, Nef, Vpr, Vpu, Vif and Env (e.g., gp120, gp140, gp41 and gp160). In some embodiments, the selected antigen is an antigen derived from a species of Orthomyxoviridae. In some embodiments, the selected antigen derived from Othomyxoviridae is derived from a strain of influenza A selected from, by way of non-limiting example, H1N1, H2N2, H3N2, H5N1, H7N7, H1N2H9N2, H7N2, H7N3, and H10N7. In some embodiments, the selected antigen is a hemagglutinin glycoprotein derived from Othomyxoviridae. In some embodiments, the selected antigen is a neuraminidase derived from Othomyxoviridae. In some embodiments, the selected antigen is derived from a coronavirus. In some embodiments, the selected antigen is derived from a SARS coronavirus.

In some embodiments, the methods disclosed herein are used to generate antibodies that bind and/or are specific to selected self antigens. In some embodiment, the self antigens originate from within an organism, tissue, or cell. In some embodiments, a self antigen comprises an endogenous antigen. In some embodiments, a self antigen comprises an endogenous antigen produced by an endogenous retrovirus. In some embodiments, self antigens comprise neo-self antigens, microbially or parasite encoded neo-self antigens, or other neo-self antigens expressed as a result of genetic alteration to an organism or cell. In some embodiments, a chimeric mouse expresses a neo-self antigen. In some embodiments, the methods disclosed herein are used to generate antibodies that bind and/or are specific to selected self antigens that antagonize a disease process. In some embodiments, the disease process is an autoimmune disorder. In some embodiments, the methods disclosed herein are used to generate antibodies that bind and/or are specific to selected auto antigens or immunologically reactive epitopes that mimic that of a self antigen or autoantigen.

In some embodiments, the methods disclosed herein are used to generate antibodies that bind and/or are specific to antigens and antagonize a disease processes. In some embodiments, the selected antigens are antibodies that contribute to the pathogenesis of a disorder or disease process.

In some embodiments, utilizing the techniques disclosed herein, monoclonal antibodies displaying a multitude of specificities are generated that neutralize entire clades of HIV variants. In some embodiments, this is accomplished by targeting an obligatory structural component of the HIV viral envelope proteins. In some embodiments, this is accomplished by targeting a host co-receptor protein.

In some embodiments, the selected antigen is an autoimmune antigen. In some embodiments, the autoimmune antigen is selected from the list: thyroglobulin, thyroid peroxidase, cytoplasmic TSH receptor, intrinsic factor, beta-adrenergic receptor, acetyl choline receptor, myelin basic protein, amyloid beta, amyloid precursor protein, collagen, sodium-iodide symporter, histone polypeptides and nucleic acids.

The technologies disclosed herein provide new strategies for the rapid development of diagnostic and therapeutic antibodies for the detection and treatment of emerging infectious diseases and chronic illnesses such as cancer and autoimmunity. In some embodiments, the antibodies produced by the methods disclosed herein are used for detecting or quantitating various serum proteins for diagnostic purposes. In some embodiments, the antibodies produced by the methods disclosed herein are used for detecting or quantitating various markers for diagnostic purposes. In some embodiments, the markers are cell surface markers. In some embodiments, the markers are cancer or tumor markers.

In some embodiments, the antibodies produced by the methods disclosed herein are used for therapeutic treatments. In some embodiments, the antibodies produced by the methods disclosed herein are reagents used for diagnostic and/or research purposes.

In some embodiments, antibodies capable of selectively binding to a wide range of antigens are produced by a method described herein. Any antigen capable of inducing an immune response when introduced to an organism is suitable for use in a method described herein. In some embodiments, antigens that are normally subjected to self tolerance mechanisms, such as auto antigens, are used in a method described herein. In some embodiments, the selected antigens fail to induce antibodies utilizing standard immunization protocols.

In some embodiments, a method described herein utilizes any organism suitable for antibody production, including a cell or tissue thereof. In some embodiments, organisms suitable for antibody production include any animal of the Vertebrate class, Mammalia (i.e., mammals), including, and without limitation, primates, rodents, livestock and domestic pets. In certain instances, in the production of an antibody, a suitable experimental animal, such as, for example, but not limited to, a rabbit, a sheep, a hamster, a guinea pig, a mouse, a rat, or a chicken, is administered (i.e., immunized with, inoculated against) an antigen against which an antibody is desired.

Pharmaceutical Compositions and Methods of Administration

In certain embodiments, provided herein, are pharmaceutical compositions comprising an antibody and one or more physiologically acceptable carriers. Physiologically acceptable carriers include excipients and auxiliaries which facilitate processing of the active agents into preparations which are used pharmaceutically. In certain instances, proper formulation is dependent upon the route of administration chosen. A summary of pharmaceutical compositions is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

Provided herein are pharmaceutical compositions that include an antibody and a pharmaceutically acceptable diluent(s), excipient(s), or carrier(s). In addition, an antibody is optionally administered as pharmaceutical compositions in which they are mixed with other active ingredients, as in combination therapy. In some embodiments, the pharmaceutical compositions includes other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

A pharmaceutical composition refers to a mixture of an antibody with other chemical components, such as carriers, stabilizers, diluents, dispersing agents, suspending agents, thickening agents, and/or excipients. The pharmaceutical composition facilitates administration of an antibody to an organism. In practicing the methods of treatment or use provided herein, therapeutically effective amounts of an antibody are administered in a pharmaceutical composition to an organism (e.g., a mammal) having a condition, disease, or disorder to be treated. Preferably, the organism (e.g., a mammal) is a human. A therapeutically effective amount varies depending on the severity and stage of the condition, the age and relative health of the subject, the potency of the antibody used and other factors. Antibodies are optionally used singly or in combination with one or more therapeutic agents as components of mixtures.

The pharmaceutical formulations described herein are optionally administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Methods of Dosing and Treatment Regimens

An antibody is optionally used in the preparation of medicaments for the prophylactic and/or therapeutic treatment of inflammatory conditions or conditions that would benefit, at least in part, from amelioration. In addition, a method for treating any of the diseases or conditions described herein in a subject in need of such treatment, involves administration of pharmaceutical compositions containing an antibody as described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

Furthermore, in some embodiments, provided herein is a method of treating a disorder mediated by an antigen by administering a therapeutically effective antibody that binds or specifically binds to the selected antigen to an individual in need thereof. Exemplary antigens are set forth herein and include, by way of non-limiting example, viral antigens (e.g., HIV antigens, influenza antigens, SARS antigens), autoantigens, tumor antigens, various pathogen related antigens and the like. Likewise, disorders mediated by the selected antigen include any disorder so mediated, including, by way of non-limiting example, viral infections and syndromes caused thereby (e.g., HIV, influenza, and SARS), as well as pathogenic and parasitic infections and syndromes caused thereby.

In certain instances wherein the patient's condition does not improve, upon the doctor's discretion the administration of an antibody is optionally administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of an antibody is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms.

In some embodiments, the pharmaceutical composition described herein is in unit dosage forms suitable for single administration of precise dosages. In unit dosage form, the formulation is divided into unit doses containing appropriate quantities of an antibody. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

The daily dosages appropriate for an antibody are from about 0.01 to 2.5 mg/kg per body weight. An indicated daily dosage in the larger organism (e.g., a mammal), including, but not limited to, humans, is in the range from about 0.5 mg to about 100 mg, conveniently administered in divided doses, including, but not limited to, up to four times a day or in extended release form. Suitable unit dosage forms for oral administration include from about 1 to 50 mg active ingredient. The foregoing ranges are merely suggestive, as the number of variables in regard to an individual treatment regime is large, and considerable excursions from these recommended values are not uncommon. Such dosages are optionally altered depending on a number of variables, not limited to the activity of the antibody used, the disease or condition to be treated, the mode of administration, the requirements of the individual subject, the severity of the disease or condition being treated, and the judgment of the practitioner.

Toxicity and therapeutic efficacy of such therapeutic regimens are optionally determined in cell cultures or experimental organisms, including, but not limited to, the determination of the LD50 (the dose lethal to 50% of the population) and the ED50 (the dose therapeutically effective in 50% of the population). The dose ratio between the toxic and therapeutic effects is the therapeutic index, which is expressed as the ratio between LD50 and ED50. An antibody exhibiting high therapeutic indices is preferred. The data obtained from cell culture assays and animal studies are optionally used in formulating a range of dosage for use in human. The dosage of such an antibody lies preferably within a range of circulating concentrations that include the ED50 with minimal toxicity. The dosage optionally varies within this range depending upon the dosage form employed and the route of administration utilized.

Combination Treatments

Antibody compositions described herein are also optionally used in combination with other therapeutic reagents that are selected for their therapeutic value for the condition to be treated. In general, the compositions described herein and, in embodiments, where combinational therapy is employed, other agents do not have to be administered in the same pharmaceutical composition, and, because of different physical and chemical characteristics, are optionally administered by different routes. The initial administration is optionally made according to established protocols, and then, based upon the observed effects, the dosage, modes of administration and times of administration subsequently modified.

In certain instances, it is appropriate to administer an antibody composition as described herein in combination with another therapeutic agent. By way of example only, if one of the side effects experienced by a patient upon receiving an antibody composition as described herein is nausea, then it is appropriate to administer an anti-nausea agent in combination with the initial therapeutic agent. Or, by way of example only, the therapeutic effectiveness of an antibody are enhanced by administration of an adjuvant (i.e., by itself the adjuvant has minimal therapeutic benefit, but in combination with another therapeutic agent, the overall therapeutic benefit to the patient is enhanced). Or, by way of example only, the benefit experienced by a patient is increased by administering an antibody with another therapeutic agent (which also includes a therapeutic regimen) that also has therapeutic benefit. In any case, regardless of the disease, disorder or condition being treated, the overall benefit experienced by the patient is either simply additive of the two therapeutic agents or the patient experiences a synergistic benefit.

Therapeutically-effective dosages vary when the drugs are used in treatment combinations. Methods for experimentally determining therapeutically-effective dosages of drugs and other agents for use in combination treatment regimens are documented methodologies. One example of such a method is the use of metronomic dosing, i.e., providing more frequent, lower doses in order to minimize toxic side effects. Combination treatment further includes periodic treatments that start and stop at various times to assist with the clinical management of the patient.

In any case, the multiple therapeutic agents (one of which is an antibody as described herein) are administered in any order, or even simultaneously. If simultaneously, the multiple therapeutic agents are optionally provided in a single, unified form, or in multiple forms (by way of example only, either as a single pill or as two separate pills). In some embodiments, one of the therapeutic agents is given in multiple doses, or both are given as multiple doses. If not simultaneous, the timing between the multiple doses optionally varies from more than zero weeks to less than four weeks. In addition, the combination methods, compositions and formulations are not to be limited to the use of only two agents; the use of multiple therapeutic combinations is also envisioned.

It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also be administered sequentially, with either therapeutic agent being administered by a regimen calling for two-step administration. The two-step administration regimen optionally calls for sequential administration of the active agents or spaced-apart administration of the separate active agents. The time period between the multiple administration steps ranges from, a few minutes to several hours, depending upon the properties of each pharmaceutical agent, such as potency, solubility, bioavailability, plasma half-life and kinetic profile of the pharmaceutical agent. Circadian variation of the target molecule concentrations are optionally used to determine the optimal dose interval.

In addition, an antibody is optionally used in combination with procedures that provide additional or synergistic benefit to the patient. By way of example only, patients are expected to find therapeutic and/or prophylactic benefit in the methods described herein, wherein pharmaceutical compositions of an antibody and/or combinations with other therapeutics are combined with genetic testing to determine whether that individual is a carrier of a mutant gene that is correlated with certain diseases or conditions.

An antibody and the additional therapy(ies) are optionally administered before, during or after the occurrence of a disease or condition, and the timing of administering the composition containing an antibody varies in some embodiments. Thus, for example, an antibody is used as a prophylactic and is administered continuously to subjects with a propensity to develop conditions or diseases in order to prevent the occurrence of the disease or condition. An antibody and compositions are optionally administered to a subject during or as soon as possible after the onset of the symptoms. The administration of the agents are optionally initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration is optionally via any route practical, such as, for example, an intravenous injection, a bolus injection, infusion over 5 minutes to about 5 hours, a pill, a capsule, transdermal patch, buccal delivery, and the like, or combination thereof. An antibody is preferably administered as soon as is practicable after the onset of a disease or condition is detected or suspected, and for a length of time necessary for the treatment of the disease, such as, for example, from about 1 month to about 3 months. The length of treatment optionally varies for each subject, and the length is then determined using the known criteria. For example, an antibody or a formulation containing an antibody are administered for at least 2 weeks, preferably about 1 month to about 5 years, and more preferably from about 1 month to about 3 years.

While certain embodiments, of the present invention have been shown and described herein, it will be apparent to those skilled in the art that such embodiments, are provided by way of example only. Numerous variations, changes, and substitutions will now occur to those skilled in the art without departing from the invention. It should be understood that in some embodiments, of the invention various alternatives to the embodiments, described herein are employed in practicing the invention.

EXAMPLES

Example 1

The following example demonstrates the production of B-cell lines derived from MMTV-tTA/TRE-MYC mice.

MMTV-tTA/TRE-MYC mice are maintained on doxycycline for eight weeks after birth and then are switched to a normal diet. The mice develop an externally evident lymphadenopathy and splenomegaly, and present with a number of the clinical signs that are consistently seen associated with lymphoid neoplasia (scruffy fur, hunched posture, labored breathing, anemia, organomegaly, etc.). The mice are euthanized and their lymph nodes and spleens are collected for analysis. Single cell suspensions are generated from some of the lymph nodes and a portion of the spleen. Those cells are used for flow cytometric analyses. The initial characterization of the tumors demonstrated the high prevalence of activated B-cells. Some of the same cells are used to seed cultures to generate B-cell lines. These cells are cultured in lymphocyte media (RPMI 1640, 10% Fetal Calf Serum, penicillin/streptomycin, L-glutamine, HEPES, non-essential amino acids, sodium pyruvate and 2-β-mercaptoethanol). Approximately 14-21 days later, some of the wells began to exhibit clonal outgrowth of cell lines. The cells are carefully expanded until they were adapted to growth in large flasks. A portion of the cells are cryopreserved in 10% DMSO.

Two cell lines were initially picked, designated TBLK6 and TBLK7. These cell lines exhibited different surface expression levels of CD138. The levels of immunoglobulin secretion into the tissue culture medium is measured after seeding. Both cell lines spontaneously secreted immunoglobulin into the growth medium. The levels of secretion are increased by the addition of IL-4 and IL-6 into the initial innoculum. Immunoglobulins secreted by both TBLK6 and TBLK7 are shown to be IgM. In some embodiments, single cells are cloned from both cell lines in order to generate true monoclonal populations. A number of MMTV-tTA/TRE-MYC bigenic mice are generated that, in some embodiments, are used for isolating the AN1/T3 population by cell sorting.

Example 2

The following example demonstrates that antibodies produced in Myc-over-expressing mice function in vivo.

A model of lethal viral infection is used. Porcine Rabies Virus (PRV) is a member of the alpha-herpes viruses that has been previously shown to be lethal in mice following intravenous administration. Two variants of PRV are constructed. In one instance, one of the sequences for a gene called US-9 was fused to GFP. This construct allowed for tracking of the virus and virally infected cells in a different setting. US-9 protein expression is confirmed and US-9 retained its function as the fusion protein. The virus is fully pathogenic in spite of its additional genetic cargo. A variant of PRV that encodes the open reading frame for HEL is also generated. This viral variant is shown to express HEL by Western blot analysis of infected cells.

GFP-expressing virus or the HEL-expressing virus innocula are incubated with HEL-specific antibodies diluted 1:500 for one hour, on ice. The mixtures are then injected intravenously into groups of four mice. The mice are then monitored for four days following administration of the virus and antibody mixtures.

Figure 7:
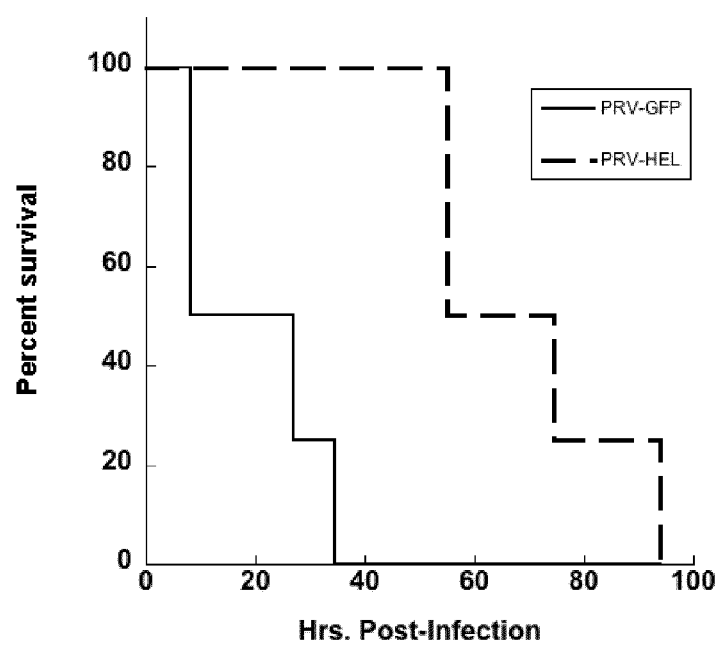
FIG. 7. Protection of mice with novel HEL-specific antibodies from lethal challenge of PRV variants that express HEL. Cohorts of mice were infected by intravenous administration of two different vari undifferentiated and differentiated white blood cell populations including tissue specific and specialized varieties.
Figure 8:
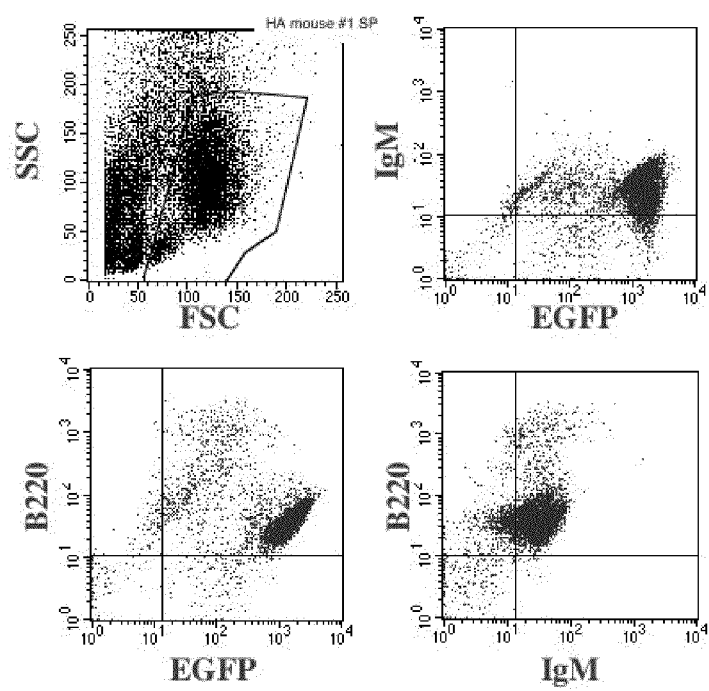
Figure 9:
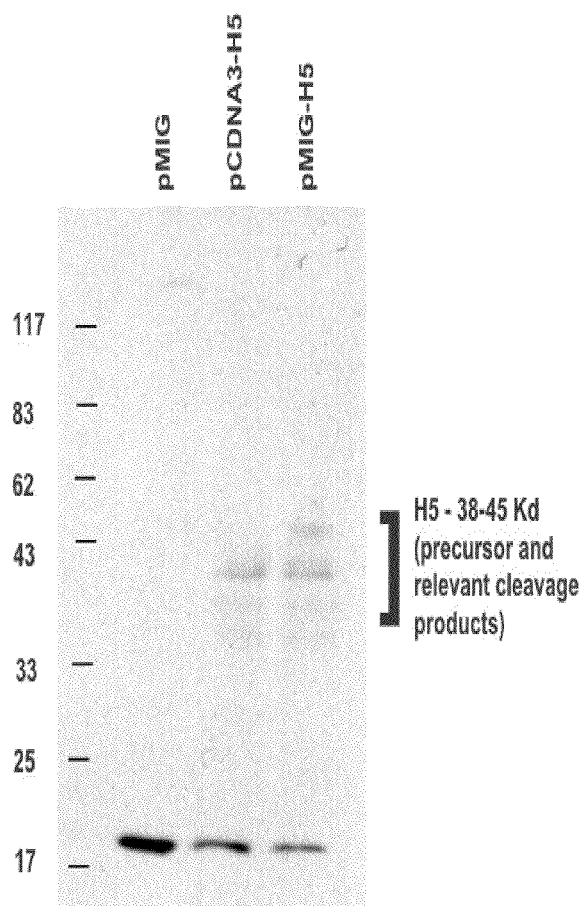

As shown in FIG. 7, the GFP-expressing virus is not affected by the presence of HEL-specific antibodies. The kinetics of mortality in that group is comparable with our previous experience with wild type PRV strains. In contrast, the kinetics of mortality in mice that received the HEL-expressing virus is significantly delayed and that group of mice lived for almost twice as long as the mice injected with the GFP-expressing virus. The viruses used for these experiments only expressed the US-9 fusion protein transiently. After entry into cells, they produce wild type PRV.

Example 3

In this example, Myc-ER is used for the conditional immortalization of long term hematopoietic stem cells. A group of bone marrow chimeric mice are generated using 5FU enriched bone marrow derived stem cells, as follows. For bone marrow derived hematopoietic stem cells, 5 mg/mouse of 5-fluorouracil (5FU) is administered intravenously, in order to enrich for long-term hematopoietic stem cells, and induce HSC proliferation in vivo. The bone marrow cells are collected from the femurs and tibia bones 5 days later. The red blood cells are lysed, using a hypotonic lysis buffer. The remaining cells are washed twice in media and plated at a concentration of $2\times10^6$ cells/ml, in a 24 well plate, in DMEM media supplemented with 15% heat inactivated fetal calf serum, penicillin/streptomycin, L-glutamine, Non-essential amino acids, recombinant human IL-3, IL-6 and Stem Cell Factor (SCF). The cells are cultured for 24 hours prior to the first spin infection, and are subject to the infection procedure 3 times, every 24 hours. A day after the last spin infection, the cells are analyzed by flow cytometry. Lentivirally transduced bone marrow derived hematopoietic stem cells are reconstituted to lethally irradiated mice, and are checked for GFP expression in lymphoid organs 12 weeks later. In this instance, hematopoietic stem cells are allowed to reconstitute a normal peripheral lymphoid compartment for 8-12 weeks after bone marrow transplantation. The splenic, GFP+ AN-1/T3 cells are isolated from those mice and are used for in vitro immortalization protocols, as described above. The key difference is that instead of withdrawing doxycycline from the system, 10 nM 4-hydroxytamoxifen (4OHT) is added to the medium. In some embodiments, sorted, GFP+AN-1/T3 cells are adoptively transferred into cohorts of wild type recipient mice that are treated once weekly with 1 mg/mouse of 4OHT, intraperitoneally. The mice are monitored daily for the appearance of clinical signs associated with the development of B-cell lymphomas. The resulting tumors are collected and used for generating B-cell lines as described herein, using 4OHT instead of doxycycline as the regulator of Myc function.

Example 4

In this example, Myc-ER and Bcl-2 are used for the conditional immortalization of long term hematopoietic stem cells. A group of bone marrow chimeric mice are generated using 5FU enriched bone marrow derived stem cells, as follows. For bone marrow derived hematopoietic stem cells, 5 mg/mouse of 5-fluorouracil (5FU) is administered intravenously, in order to enrich for long-term hematopoietic stem cells, and induce HSC proliferation in vivo. The bone marrow cells are collected from the femurs and tibia bones 5 days later. The red blood cells are lysed, using a hypotonic lysis buffer. The remaining cells are washed twice in media and plated at a concentration of $2\times10^6$ cells/ml, in a 24 well plate, in DMEM media supplemented with 15% heat inactivated fetal calf serum, penicillin/streptomycin, L-glutamine, Non-essential amino acids, recombinant human IL-3, IL-6 and Stem Cell Factor (SCF). The cells are cultured for 24 hours prior to the first spin infection with a GFP expressing lentivirus encoding the expression of Myc-ER and Bcl-2. The cells are subject to the infection procedure 3 times, every 24 hours. A day after the last spin infection, the cells are analyzed by flow cytometry. Lentivirally transduced bone marrow derived hematopoietic stem cells are reconstituted to lethally irradiated mice. In this instance, hematopoietic stem cells are allowed to reconstitute a normal peripheral lymphoid compartment for 8-12 weeks after bone marrow transplantation. The splenic, GFP+ AN-1/T3 cells are isolated from those mice and are used for in vitro immortalization protocols, as described above. 4OHT is added to the medium to induce Myc activation. In some embodiments, sorted, GFP+ AN-1/T3 cells are adoptively transferred into cohorts of wild type recipient mice that are treated once weekly with 1 mg/mouse of 4OHT, intraperitoneally. The mice are monitored daily for the appearance of clinical signs associated with the development of B-cell lymphomas. The resulting tumors are collected and used for generating B-cell lines as described herein, using 4OHT instead of doxycycline as the regulator of Myc function.

Example 5

In order to test the notion of harnessing the MMTV-tTA/TRE-MYC mice to generate novel antibodies to antigens of interest through the introduction into the system as neo-self antigens, a retroviral bone marrow chimeric mice was used. A variant of pMIG that encodes the cDNA for H5 hemagglutinin from a highly pathogenic avian influenza virus, A/Ty/Ont/7732/66 (H5N9) was first generated. HSCs enriched from the bone marrows of mice that had been treated with 5-fluorouracil 5 days prior to collection, were then obtained as previously described. The donor cells were obtained from TRE-MYC mice. The cells were transduced with one retrovirus that encodes the tetracycline transactivator protein (tTA) as well as pMIG-H5. The transduced bone marrow HSCs were used to reconstitute lethally irradiated mice. The bone marrow chimeric mice were maintained on SEPTRA and observed daily for externally evident clinical signs of hematological malignancies (scruffy fur, labored breathing, externally evident lymphadenopathy or splenomegaly, hunched posture, dehydration, and hind limb paralysis). A cohort of 5 mice presented with clinical signs of hematological malignancies in a 7-day period, starting 6 weeks after transplantation. The lymph nodes and spleens were collected from euthanized mice and used to generate single cell suspensions. The remaining cells were either cultured to begin to generate cell lines, or cryopreserved for subsequent analysis. A small fraction of the cells were stained for cell surface markers and analyzed by flow cytometry (FIG. 8). FIG. 8 shows the surface profile of the cells isolated from the bone marrow chimeric mice that had developed a hematological malignancy. These are uniformly B220+/IgM+, suggesting that the mice had developed a B-cell leukemia/lymphoma composed of mature B-cells. These cells were placed in culture and clonally expanded populations were passed starting 8 days after initial seeding. This is a significantly faster timeline than what is normally achieved with current approaches to monoclonal antibody production. In addition, the accelerated time frame by which this novel approach has allowed us to generate novel antibodies to hemagglutinin should render this approach as a rapid response platform for the development of novel neutralizing antibodies to new and emerging infectious diseases and other biological threats.

The serum from these mice was collected to test for the presence of antibodies to H5. Immunoblot analysis with the serum from these mice showed specific reactivity to the HA1 subunit of the H5 HA (FIG. 9). Cell lysates were obtained from 293FT cells that had been transiently transfected with two different expression plasmids encoding H5 (pCDNA3-H5 and pMIG-H5). The blots were probed with sera obtained from leukemic mice. The banding pattern that developed was consistent with H5 and the cleavage products that develop during the normal maturation and processing of HA in a cell. The mature HA is composed of two subunits the HA1 and the HA2. The HA1 subunit (~40 kDa) forms the globular head of the molecule and is responsible for binding to the host cell sialic acid receptors on surface glycoproteins and glycolipids.

The HA2 (~20 kDa) subunit is responsible for fusion of the viral envelope with the endosomal membranes of the host cell during entry. A protease cleavage site separates these two subunits and cleavage by host protease is required for entry into the host cell. The vast majority of virus neutralizing epitopes are found in the HA1 subunit 22 and inhibit virus-receptor interaction.

Figure 10:
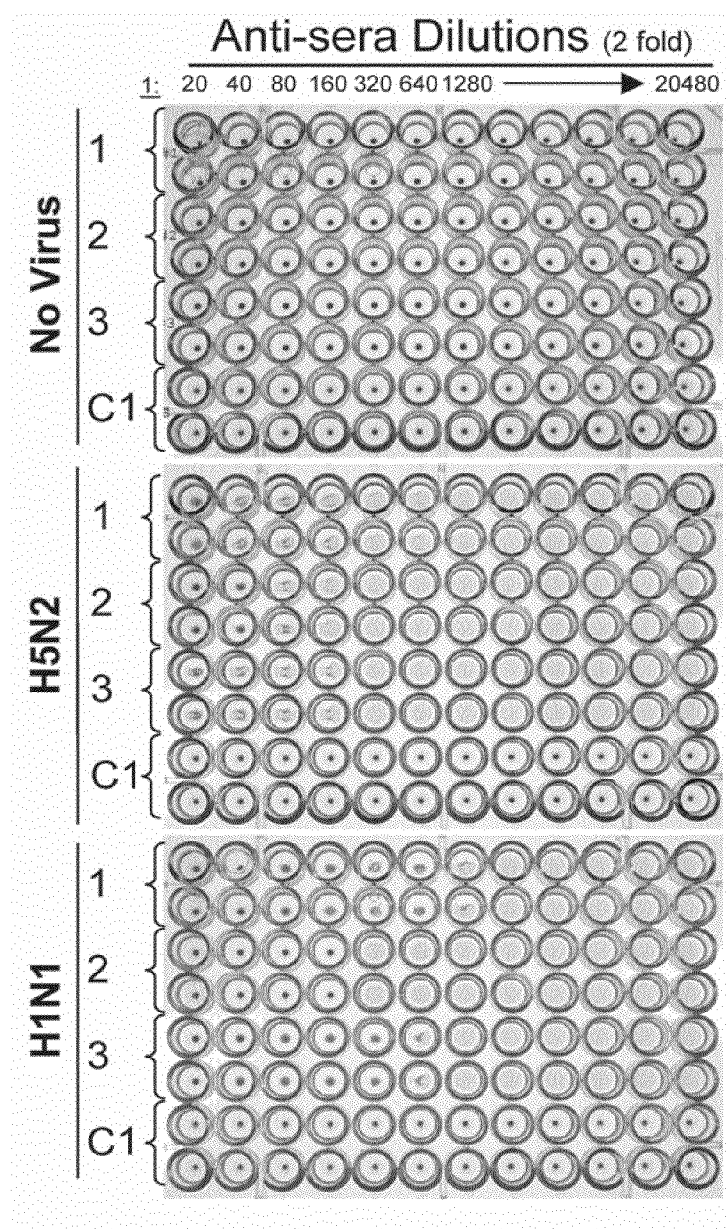
Figure 11:
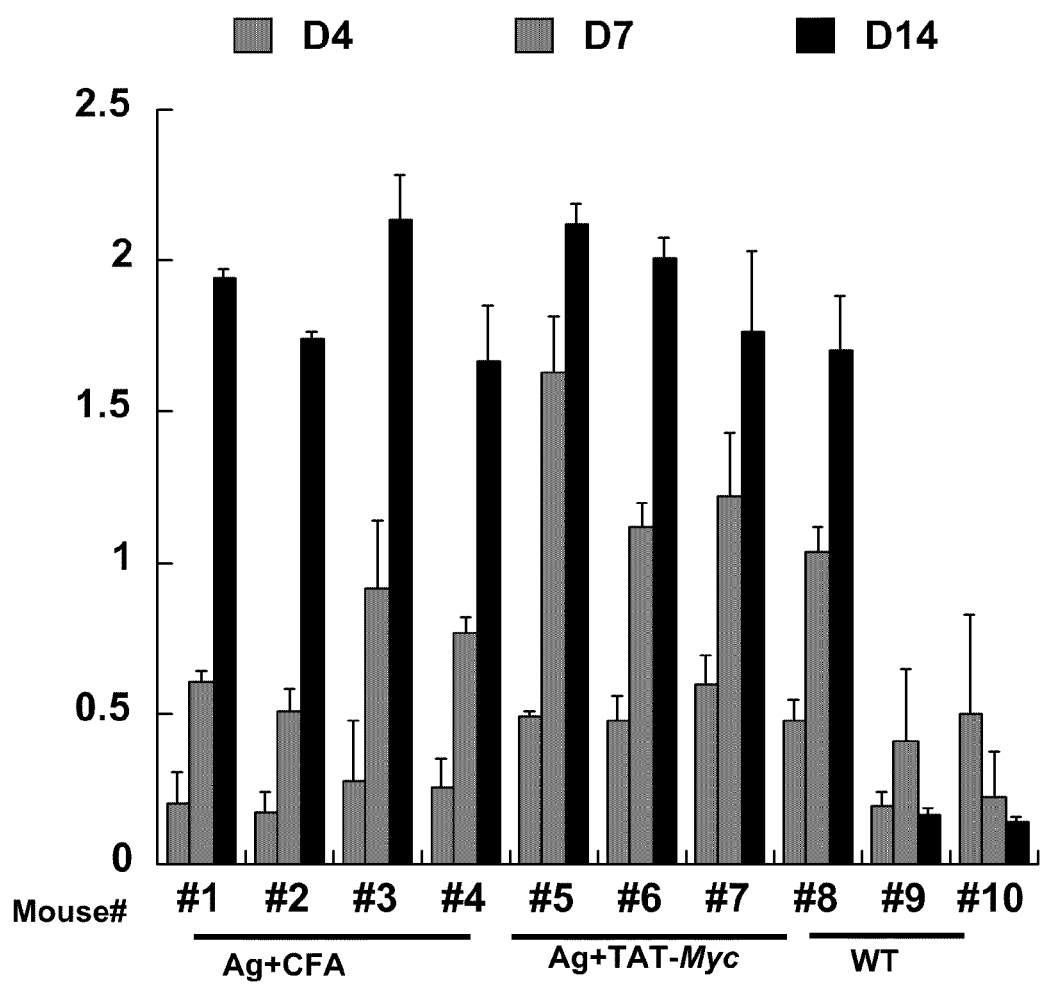
Figure 12:
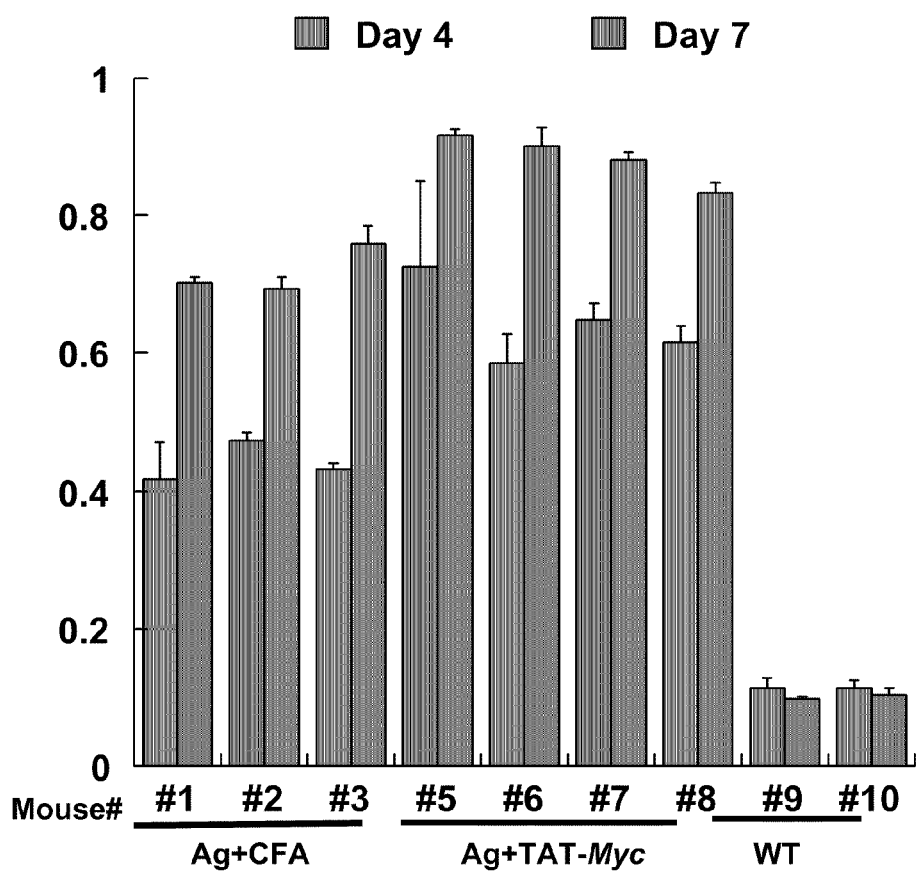
Figure 13:
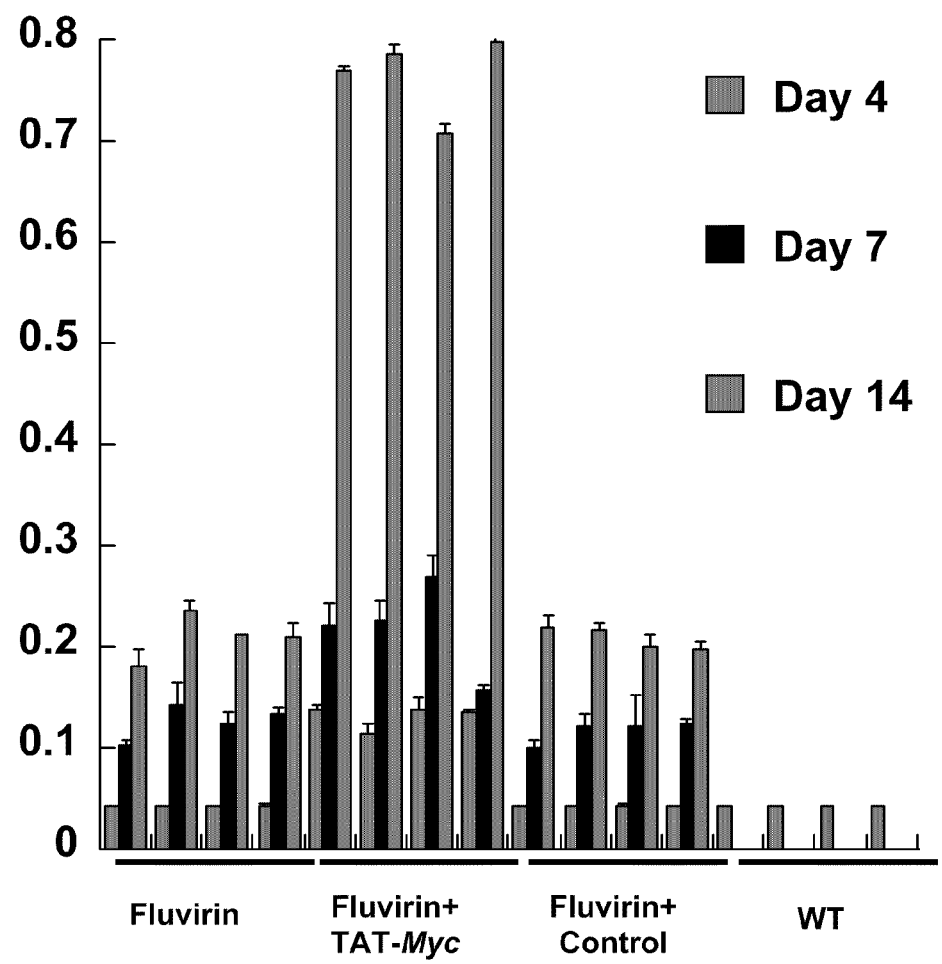

Heamagglutination inhibition analysis of mouse serum obtained from retroviral chimeric mice was performed to test the ability of the sera to block virus-receptor interaction with a variety influenza A isolates including H5N2, H1N1, H7N2, H3N2, and H6N8 subtypes (FIG. 10).

Example 6

Mice (n=20) are divided into two groups. The first group (n=10) are immunized with HEL mixed with Freund's adjuvant. The second group (n=10) are immunized with HEL mixed with Tat-Myc.

Both groups receive a booster shot of the HEL antigen mixed with Incomplete Freund's Adjuvant.

Sera is collected from each mouse at days 4, 7, 14, 21 and 28. Reactivity to HEL protein is assayed by ELISA.

On day 35, spleens are harvested from each mouse. The spleens are processed into single cell suspension. Red blood cells (RBCs) are removed with lysis buffer. Lymphocytes are divided into two samples. The first sample is incubated with Tat-Myc and HEL antigen. The second sample is incubated with TAT-MYC.

Example 7

Mice (n=20) are divided into two groups. The first group (n=10) are immunized with Fluvirin (2007-2008) mixed with Freund's adjuvant. The second group (n=10) are immunized with Fluvirin (2007-2008) mixed with Tat-Myc.

Both groups receive a booster shot of the Fluvirin (2007-2008) mixed with Incomplete Freund's Adjuvant (IFA).

Sera is collected from each mouse at days 4, 7, 14, 21 and 28. Reactivity to Fluvirin (2007-2008) is assayed by ELISA.

On day 35, spleens are harvested from each mouse. The spleens are processed into single cell suspension. Red blood cells (RBCs) are removed with lysis buffer. Lymphocytes are divided into two samples. The first sample is incubated with Tat-Myc and Fluvirin (2007-2008). The second sample is incubated with TAT-MYC.

It should be understood that various alternatives to the embodiments, of the invention described herein may be employed in practicing the invention. It is intended that the following claims define the scope of the invention and that methods and structures within the scope of these claims and their equivalents be covered thereby.

SEQUENCE LISTING

```
<160> NUMBER OF SEQ ID NOS: 6

<210> SEQ ID NO 1
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190
```

-continued

Leu Gln Asp Leu Ser Ala Ala Ala Ser Glu Cys Ile Asp Pro Ser Val
        195                 200                 205

Val Phe Pro Tyr Pro Leu Asn Asp Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Lys Gly Glu Leu Asn Ser Lys Leu Glu
    450                 455

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
1               5

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Lys Pro Ile Pro Asn Pro Leu Leu Gly Leu Asp Ser Thr
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 4

Ile Pro Asn Pro Leu Leu Gly Leu Asp
1               5

<210> SEQ ID NO 5
<211> LENGTH: 492
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 5

Met Arg Lys Lys Arg Gln Arg Arg Met Asp Phe Phe Arg Val
1               5                   10                  15

Val Glu Asn Gln Gln Pro Pro Ala Thr Met Pro Leu Asn Val Ser Phe
            20                  25                  30

Thr Asn Arg Asn Tyr Asp Leu Asp Tyr Asp Ser Val Gln Pro Tyr Phe
        35                  40                  45

Tyr Cys Asp Glu Glu Asn Phe Tyr Gln Gln Gln Gln Gln Ser Glu
    50                  55                  60

Leu Gln Pro Pro Ala Pro Ser Glu Asp Ile Trp Lys Lys Phe Glu Leu
65                  70                  75                  80

Leu Pro Thr Pro Pro Leu Ser Pro Ser Arg Arg Ser Gly Leu Cys Ser
                85                  90                  95

Pro Ser Tyr Val Ala Val Thr Pro Phe Ser Leu Arg Gly Asp Asn Asp
            100                 105                 110

Gly Gly Gly Gly Ser Phe Ser Thr Ala Asp Gln Leu Glu Met Val Thr
        115                 120                 125

Glu Leu Leu Gly Gly Asp Met Val Asn Gln Ser Phe Ile Cys Asp Pro
130                 135                 140

Asp Asp Glu Thr Phe Ile Lys Asn Ile Ile Gln Asp Cys Met Trp
145                 150                 155                 160

Ser Gly Phe Ser Ala Ala Ala Lys Leu Val Ser Glu Lys Leu Ala Ser
                165                 170                 175

Tyr Gln Ala Ala Arg Lys Asp Ser Gly Ser Pro Asn Pro Ala Arg Gly
            180                 185                 190

His Ser Val Cys Ser Thr Ser Ser Leu Tyr Leu Gln Asp Leu Ser Ala
        195                 200                 205

Ala Ala Ser Glu Cys Ile Asp Pro Ser Val Val Phe Pro Tyr Pro Leu
    210                 215                 220

Asn Asp Ser Ser Ser Pro Lys Ser Cys Ala Ser Gln Asp Ser Ser Ala
225                 230                 235                 240

Phe Ser Pro Ser Ser Asp Ser Leu Leu Ser Ser Thr Glu Ser Ser Pro
                245                 250                 255

Gln Gly Ser Pro Glu Pro Leu Val Leu His Glu Glu Thr Pro Pro Thr
            260                 265                 270

```
Thr Ser Ser Asp Ser Glu Glu Glu Gln Glu Asp Glu Glu Glu Ile Asp
        275                 280                 285

Val Val Ser Val Glu Lys Arg Gln Ala Pro Gly Lys Arg Ser Glu Ser
290                 295                 300

Gly Ser Pro Ser Ala Gly Gly His Ser Lys Pro Pro His Ser Pro Leu
305                 310                 315                 320

Val Leu Lys Arg Cys His Val Ser Thr His Gln His Asn Tyr Ala Ala
                325                 330                 335

Pro Pro Ser Thr Arg Lys Asp Tyr Pro Ala Ala Lys Arg Val Lys Leu
                340                 345                 350

Asp Ser Val Arg Val Leu Arg Gln Ile Ser Asn Asn Arg Lys Cys Thr
                355                 360                 365

Ser Pro Arg Ser Ser Asp Thr Glu Glu Asn Val Lys Arg Arg Thr His
370                 375                 380

Asn Val Leu Glu Arg Gln Arg Arg Asn Glu Leu Lys Arg Ser Phe Phe
385                 390                 395                 400

Ala Leu Arg Asp Gln Ile Pro Glu Leu Glu Asn Asn Glu Lys Ala Pro
                405                 410                 415

Lys Val Val Ile Leu Lys Lys Ala Thr Ala Tyr Ile Leu Ser Val Gln
                420                 425                 430

Ala Glu Glu Gln Lys Leu Ile Ser Glu Glu Asp Leu Leu Arg Lys Arg
                435                 440                 445

Arg Glu Gln Leu Lys His Lys Leu Glu Gln Leu Arg Lys Gly Glu Leu
        450                 455                 460

Asn Ser Lys Leu Glu Gly Lys Pro Ile Pro Asn Pro Leu Leu Gly Leu
465                 470                 475                 480

Asp Ser Thr Arg Thr Gly His His His His His His
                485                 490

<210> SEQ ID NO 6
<211> LENGTH: 9
<212> TYPE: PRT
<213> ORGANISM: Human immunodeficiency virus

<400> SEQUENCE: 6

Arg Lys Lys Arg Arg Gln Arg Arg Arg
1               5
```

What is claimed is:

1. A method for generating a B-cell that expresses antibodies specific for a selected antigen comprising:
  contacting an antibody expressing B-cell with (i) the selected antigen and (ii) an exogenous fusion peptide, wherein the fusion peptide comprises (a) a peptide transduction domain, and (b) Myc, under conditions wherein the presence of the fusion peptide and the selected antigen promotes proliferation and survival of the B-cell that expresses antibodies specific for the selected antigen.

2. The method of claim 1, wherein the B-cell is an anergic B cell.

3. The method of claim 2, wherein B-cell anergy is broken by contacting the anergic B-cell with the fusion peptide.

4. The method of claim 1, wherein the fusion peptide comprises the sequence (SEQ ID NO. 5)
MRKKRRQRRRMDFFRVVENQQPPATMPLNVSFTNRNYDLDYDSVQPYFYCDEEENFYQQQQ

QSELQPPAPSEDIWKKFELLPTPPLSPSRRSGLCSPSYVAVTPFSLRGDNDGGGGSFSTADQLE

MVTELLGGDMVNQSFICDPDDETFIKNIIIQDCMWSGFSAAAKLVSEKLASYQAARKDSGSPN

PARGHSVCSTSSLYLQDLSAAASECIDPSVVFPYPLNDSSSPKSCASQDSSAFSPSSDSLLSSTES

SPQGSPEPLVLHEETPPTTSSDSEEEQEDEEEIDVVSVEKRQAPGKRSESGSPSAGGHSKPPHSP

LVLKRCHVSTHQHNYAAPPSTRKDYPAAKRVKLDSVRVLRQISNNRKCTSPRSSDTEENVKR

-continued

```
RTHNVLERQRRNELKRSFFALRDQIPELENNEKAPKVVILKKATAYILSVQAEEQKLISEEDLL

RKRREQLKHKLEQLRKGELNSKLEGKPIPNPLLGLDSTRTGHHHHHH,
and
``` variants thereof in which the portion of the fusion peptide corresponding to Myc retains at least 90% amino acid sequence identity, and wherein the amino acid sequence substitutions are conservative, and the variants retain Myc biological activity comprising promoting proliferation and survival of B-cells.

5. The method of claim 1, wherein contacting the B-cell that expresses antibodies with the fusion peptide occurs ex vivo.

6. The method of claim 1, wherein contacting the antibody expressing B-cell with the fusion peptide occurs in an animal selected from the group consisting of primate, rodent, livestock, and domestic pet.

7. The method of claim 6, wherein the animal expresses the selected antigen.

8. The method of claim 7, wherein the selected antigen is expressed in hematopoietic stem cells, or cells differentiated from the hematopoietic stem cells, wherein the cells were transduced with a nucleic acid encoding the selected antigen ex vivo.

9. The method of claim 6, wherein the animal is exposed to the selected antigen by immunization.

10. The method of claim 6, wherein the animal is a mouse.

11. The method of claim 1, wherein the selected antigen is a self-antigen.

12. The method of claim 1, wherein the selected antigen is from a virus, bacterium, parasite, or fungus.

13. The method of claim 1, wherein the peptide transduction domain is a peptide transduction domain of TAT.

14. The method of claim 6, wherein the animal is selected from the group consisting of a rabbit, a sheep, a hamster, a guinea pig, a mouse, a rat, and a chicken.

15. The method of claim 1, further comprising recovering the B-cell that expresses antibodies to the selected antigen.

16. The method of claim 1, further comprising recovering the antibodies specific for the selected antigen.

17. The method of claim 1, wherein the selected antigen is from a neoplastic cell.

18. The method of claim 1, wherein the antibody is a human antibody.

19. The method of claim 1, wherein the antibody is a mouse antibody.

20. The method of claim 1, wherein the B-cell is a human B-cell.

21. The method of claim 1, wherein the B-cell is a mouse B-cell.

22. A method for culturing a B-cell that expresses antibodies specific for a selected antigen ex vivo comprising: contacting the B-cell that expresses antibodies with (i) a selected antigen and (ii) an exogenous fusion peptide, wherein the fusion peptide comprises (a) peptide transduction domain, and (b) Myc, under conditions wherein the presence of the fusion peptide and the selected antigen promotes proliferation and survival of the B-cell that expresses antibodies specific for the selected antigen ex vivo.

23. The method of claim 22, further comprising recovering the antibodies specific for the selected antigen.

* * * * *